(12) United States Patent
Dunn et al.

(10) Patent No.: US 12,606,618 B2
(45) Date of Patent: Apr. 21, 2026

(54) ANTAGONIST ANTI-NPR1 ANTIBODIES AND METHODS OF USE THEREOF

(71) Applicant: REGENERON PHARMACEUTICALS, INC., Tarrytown, NY (US)

(72) Inventors: Michael E. Dunn, Montvale, NJ (US); Lori C. Morton, Chappaqua, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 657 days.

(21) Appl. No.: 18/062,450

(22) Filed: Dec. 6, 2022

(65) Prior Publication Data

US 2023/0250170 A1     Aug. 10, 2023

Related U.S. Application Data

(60) Provisional application No. 63/310,078, filed on Feb. 14, 2022, provisional application No. 63/286,476, filed on Dec. 6, 2021.

(51) Int. Cl.
| | |
|---|---|
| *C07K 16/28* | (2006.01) |
| *A61P 9/00* | (2006.01) |
| *C12N 15/63* | (2006.01) |

(52) U.S. Cl.
CPC .............. *C07K 16/28* (2013.01); *A61P 9/00* (2018.01); *C12N 15/63* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,596,541 | B2 | 7/2003 | Murphy et al. |
| 7,138,501 | B2 * | 11/2006 | Ruben ................ C07K 16/2875 |
| | | | 530/391.1 |
| 7,582,298 | B2 | 9/2009 | Stevens et al. |
| 8,246,995 | B2 | 8/2012 | Dai et al. |
| 8,257,740 | B1 | 9/2012 | Sung et al. |
| 9,090,695 | B2 | 7/2015 | Waterman et al. |
| 11,306,148 | B2 | 4/2022 | Dunn |
| 11,396,551 | B2 * | 7/2022 | Srivatsa Srinivasan ..................... |
| | | | C07K 14/7051 |
| 11,820,826 | B2 | 11/2023 | Dunn |
| 12,060,411 | B2 * | 8/2024 | Nussenzweig ......... A61K 45/06 |
| 12,065,489 | B2 * | 8/2024 | Conklin ........... A61K 47/68031 |
| 2004/0101920 | A1 | 5/2004 | Radziejewski et al. |
| 2010/0310561 | A1 | 12/2010 | Canada et al. |
| 2010/0331527 | A1 | 12/2010 | Davis et al. |
| 2011/0195454 | A1 | 8/2011 | McWhirter et al. |
| 2012/0114659 | A1 | 5/2012 | Waterman et al. |
| 2012/0270923 | A1 | 10/2012 | Mohapatra et al. |
| 2014/0031234 | A1 | 1/2014 | Despres |
| 2014/0243504 | A1 | 8/2014 | Davis et al. |
| 2014/0343120 | A1 | 11/2014 | Mohapatra |
| 2016/0168251 | A1 | 6/2016 | Waterman et al. |
| 2016/0199487 | A1 | 7/2016 | Gu et al. |
| 2017/0355756 | A1 | 12/2017 | Julien |
| 2020/0123263 | A1 | 4/2020 | Dunn |
| 2022/0195058 | A1 | 6/2022 | Dunn |
| 2022/0204634 | A1 | 6/2022 | Dunn |
| 2024/0327539 | A1 | 10/2024 | Dunn |
| 2025/0333524 | A1 | 10/2025 | Dunn |

FOREIGN PATENT DOCUMENTS

| | | | | |
|---|---|---|---|---|
| JP | 2017-099389 | A | 6/2017 | |
| WO | 91/17271 | | 11/1991 | |
| WO | 92/01047 | | 1/1992 | |
| WO | 2004/011618 | | 2/2004 | |
| WO | 05/103081 | | 11/2005 | |
| WO | 2008/068048 | | 6/2008 | |
| WO | 2010/065293 | | 6/2010 | |
| WO | WO-2015085055 | A2 * | 6/2015 | ......... A01K 67/0276 |
| WO | 2016/131943 | | 8/2016 | |
| WO | 2017/209553 | | 12/2017 | |
| WO | 2018/075792 | | 4/2018 | |
| WO | 2019/090039 | | 5/2019 | |
| WO | 2020/086406 | | 4/2020 | |
| WO | 2020/131935 | | 6/2020 | |
| WO | 2020/250159 | | 12/2020 | |
| WO | 2022/130182 | | 6/2022 | |
| WO | 2022/133239 | | 6/2022 | |

OTHER PUBLICATIONS

Padlan, Advances in Protein Chemistry, 1996, 49:57-133.*
Corada, Blood, 2001; 97:1679-84.*
Tzartos et al., Methods in Molecular Biology, 1996, 66:55-66.*
Kulkarni-Kale et al. Nucleic Acid Research, 2005, 33:W168-W171.*
Almagro, Frontiers in Immunology, 2018, 8: 1751.*
Sela-Culang, Frontiers in Immunology ,2013, 4: 302.*
Chiu et al., Antibodies, 2019, 8(55):1-80.*
Ni, The Protein Journal (2024) 43: 683-696.*
Wijesuriya et al., Protein Expression and Purification, 2018, 149:75-83.*

(Continued)

*Primary Examiner* — Julie Wu

(74) *Attorney, Agent, or Firm* — Merchant & Gould P.C.

(57) ABSTRACT

The present disclosure provides monoclonal antibodies that bind to the natriuretic peptide receptor 1 (NPR1) protein, and methods of use thereof. In various embodiments of the disclosure, the antibodies are fully human antagonist antibodies that bind to NPR1. In some embodiments, the antibodies of the disclosure are useful for blocking NPR1 signaling and/or activity, thus providing a means of treating or preventing a disease, disorder, or condition associated with NPR1, including hypotension, in humans.

31 Claims, 15 Drawing Sheets

Specification includes a Sequence Listing.

(56) References Cited

OTHER PUBLICATIONS

Janeway, Immuno Biology The immune system in Health and Disease, 4 edition, 1999, pp. 195-209.*

Berglund et al, Protein Science, 2008, 17:606-613.*

Benjamini, Eli, et al., "1991 Immunology: A Short Course", 2nd Edition, Wiley-Liss, Inc. New York, NY, USA, 1991, p. 40.

Bostrom, Jenny et al: "Improving antibody binding affinity and specificity for therapeutic development", Methods Mol Biol. 2009;525:353-76, xiii. Doi: 10.1007/978-1-59745-554-1_19.

Cruz, Dinna, "Midodrine: a selective [alpha]—adrenergic agonist for orthostatic hypotension and dialysis hypotension", Expert Opin Pharmacother, vol. 1, No. 4, May 1, 2000, pp. 835-840.

Blech, Michaela et al., "Structure of a Therapeutic Full-Length Anti-NPRA IgG4 Antibody: Dissecting Conformational Diversity", Biophys J. May 7, 2019; 116(9): 1637-1649, Published online Apr. 5, 2019. doi: 10.1016/j.bpj.2019.03.036.

Ferrara, Fortunato, et al., "Recombinant renewable polyclonal antibodies", Jan./Feb. 2015 mAbs. 7(1): 32-41.

Garbers, David L. et al., "Membrane guanylyl cyclase receptors: an update", Trends in Endocrinology and Metabolism, vol. 17, No. 6, pp. 251-258.

Garbers, David L., "The guanylyl cyclase receptors", Zygote 8 (Supplement) 2000, Cambridge Univ. Press, FDSUMI Symposium Proc., pp. S24-S25.

Gonzales, Noreen R., et al., "Minimizing the Immunogenicity of Antibodies for Clinical Application", Tumour Biol. Jan.-Feb. 2005;26(1):31-43. doi: 10.1159/000084184.

Kuhn, Michaela, (2003), "Structure, Regulation, and Function of Mammalian Membrane Guanylyl Cyclase Receptors, With a Focus on Guanylyl Cyclase-A", Circ. Res. 93: 700-709.

Kunik, Vered et al., "Structural consensus among antibodies defines the antigen binding site", PLoS Comput Biol. 2012;8(2):e1002388. doi: 10.1371/journal.pcbi.1002388. Epub Feb. 23, 2012.

Kussie, Paul H. et al, "A Single Engineered Amino Acid Substitution Changes Antibody Fine Specificity", Journal of Immunology, 1994, 152: 146-152.

Lowe, D. G. et al., "Human natriuretic peptide receptor-A guanylyl cyclase. Hormone cross-linking and antibody reactivity distinguish receptor glycoforms", The Journal of Biological Chemistry, Oct. 25, 1992, vol. 267, No. 30, pp. 21691-21697.

Luscher, Thomas, et al., "From 'essential' hypertension to intensive blood pressure lowering: the pros and cons of lower target values", European Heart Journal, vol. 38, No. 44, Nov. 21, 2017, pp. 3258-3271.

Misono, Kunio S., (2011), Minireview, "Structure, signaling mechanism and regulation of the natriuretic peptide receptor guanylate cyclase", FEBS Journal 278: 1818-1829.

Mohapatra, Shyam S., (2007), "Role of natriuretic peptide signaling in modulating asthma and inflammation", Can. J. Physiol. Pharmacol. 85: 754-759.

Morris, Glenn E., "Epitope Mapping of Protein Antigens by Competition ELISA", The Protein Protocols Handbook, Totowa, NJ, Humana Press, (Jan. 1, 1996), pp. 595-600, doi:10.1007/978-1-60327-259-9_96, ISBN 978-1-60-327259-9, DOI: http://dx.doi.org/10.1007/978-1-60327-259-9_96.

Oliver, Paula M. et al., "Natriuretic peptide receptor 1 expression influences blood pressures of mice in a dose-dependent manner", Proc. Natl. Acad. Sci. USA, vol. 95, pp. 2547-2551, Mar. 1998.

Pandey, Kailash N., (2011), "The functional genomics of guanylyl cyclase/natriuretic peptide receptor-A: Perspectives and paradigms", Minireview, the FEBS Journal 278: 1792-1807.

Pandey, Kailash N., (2011), "Guanylyl cyclase / atrial natriuretic peptide receptor-A: role in the pathophysiology of cardiovascular regulation", Can. J. Physiol. Pharmacol. 89: 557-573.

Panka, et al: "Variable region framework differences result in decreased or increased affinity of variant anti-digoxin antibodies", Proc Natl Acad Sci USA, May 1988;85(9):3080-4. doi: 10.1073/pnas.85.9.3080.

Potter, Lincoln R. et al., (2006), "Natriuretic Peptides, Their Receptors, and Cyclic Guanosine Monophosphate-Dependent Signaling Functions", Endocrine Reviews 27(1): 47-72.

Potter, Lincoln R., "Guanylyl Cyclase-linked natriuretic Peptide Receptors: Structure and Regulation", The Journal of Biological Chemistry, vol. 276, No. 9, Issue of Mar. 2, 2001, pp. 6057-6060.

Potter, Lincoln R., "Regulation and Therapeutic Targeting of Peptide-Activated Receptor Guanylyl Cyclases", Pharmacology & Therapeutics 130 (2011) 71-82.

Regeneron Pharmaceuticals: "A Study to Evaluate the Safety, Tolerability, Pharmacokinetics, and Pharmacodynamics of REGN9035 in Healthy Adult Volunteers and Mildly Hypertensive Participants—NCT05291546", Clinical Trials.gov, Mar. 22, 2022, XP055907382, Retrieved from the Internet: URL:https://clinicaltrials.gov/ct2/show/NCTO5291546?term=regn5381&draw=2&rank=2, [retrieved on Mar. 30, 2022], 10 pgs.

Regeneron Pharmaceuticals: "Study to Assess the Safety, Tolerability, and Pharmacokinetics of REGN5381 (an NPR1 Agonist) in Adult Humans—NCT04506645", Clinical trials.gov, Aug. 10, 2020, XP055905554, Retrieved from the Internet: URL:https://clinicaltrials.gov/ct2/show/NCT04506645, [retrieved on Mar. 25, 2022], 20 pgs.

Rudikoff et al., "Single amino acid substitution altering antigen-binding specificity", Proc. Nat. Acad. Sci. USA vol. 79, pp. 1979-1983, Mar. 1982. DOI: 10.1073/pnas.79.6.1979.

Saito, Yoshihiko et al., (2011), "Roles of guanylyl cyclase-A signaling in the cardiovascular system", Can. J. Physiol. Pharmacol. 89: 551-556.

Wark, KL et al., "Latest technologies for the enhancement of antibody affinity", Advanced Drug Delivery Reviews, Elsevier, vol. 58, No. 5-6, doi:10.1016/J.ADDR.2006.01.025, ISSN 0169-409X, (Aug. 7, 2006), pp. 657-670.

Zhao, Zhilong, et al., (2013), "ANP-NPRA Signaling Pathway—A Potential Therapeutic Target for the Treatment of Malignancy", Critical Reviews in Eukaryotic Gene Expression, 23(2): 93-101.

Koenig et al., "Mutational landscape of antibody variable domains reveals a switch modulating the interdomain conformational dynamics and antigen binding", PNAS, Jan. 24, 2017, 114 (4); E486-E495, first published Jan. 5, 2017.

Edwards et al., "The remarkable flexibility of the human antibody repertoire; isolation of over one thousand different antibodies to a single protein", BLyS. J Mol Biol Nov. 14, 2003;334 (1):103-18.

Centers for Disease Control and Prevention, "High Blood Pressure Symptoms and Causes", last reviewed May 18, 2021, accessed online on Mar. 23, 2024 at: https://www.cdc.gov/bloodpressure/about.htm, 6 pages.

U.S. Appl. No. 18/485,241 (Unpublished), entitled "Anti-NPR1 Antibodies and Uses Thereof", filed Oct. 11, 2023, 114 pgs.

Dondelinger, Mathieu, et al: "Understanding the Significance and Implications ofAntibody Numbering and Antigen-Binding Surface/Residue Definition", Frontiers in Immunology, Oct. 16, 2018;9:Article 2278, 15 pages.

Kitano, Katsuhiko, et al., "Production and characterization of monoclonal antibodies against human natriuretic peptide receptor-A or -B", Immunology Letters, vol. 47, No. 3, Sep. 1, 1995, pp. 215-222.

Solinski, Hans Jurgen, et al., "Inhibition of natriuretic peptide receptor 1 reduces itch in mice", Sci Trans! Med, vol. 11, No. 10, Jul. 10, 2019, 15 pages.

Inbal Sela-Culang et al., "The Structural Basis of Antibody-Antigen Recognition", Frontiers in Immunology, Oct. 8, 2013, vol. 4, Article 302, http://dx.doi.org/10.3389/fimmu.2013.00302, 13 pages.

Caton, Andrew et al., "Influenza virus hemagglutinin-specific antibodies Isolated from a combinatorial expression library are closely related to the immune response of the donor", Proc. Natl. Acad. Sci., USA, 87:6450-6454, No. 16, Aug. 1990.

Chen et al., "Enhancement and destruction of antibody function by somatic mutation; unequal occurrence is controlled by V gene combinatorial associations", EMBO J, Jun. 15, 1995; 14(12):2784-94.

Verbrugge, Frederik et al., "Altered Hemodynamics and End-Organ Damage in Heart Failure", Sep. 8, 2000, Circulation 142(10):998-1012.

(56) References Cited

OTHER PUBLICATIONS

Wu, H., et al: "Humanization of a Murine Monoclonal Antibody by SimultaneousOptimization of Framework and CDR Residues". J. Mol. Biol. (1999) 294, 151-162.

Kymes, Steven et al., "Real-world droxidopa or midodrine treatment persistence in patients with neurogenic orthostatic hypotension or orthostatic hypotension", Autonomic Neuroscience: Basic and Clinical 225 (2020); 102659, 5 pages.

Branden, Carl et al., "Introduction to Protein Structure", 2nd edition, Shanghai science and Technology Press, Jan. 31, 2007, (cited Chinese document and corresponding p. 306 in the English version of the document), 9 pages combined.

Republica de Colombia, Ministry of Social Protection, Instituto Nacional de Vigilancia de Medicamentos y Alimentos (INVIMA), Resolution 2023026320 (a commercial authorization issued by the sanitary Colombian authority (INVIMA)) for droxidopa, published Jun. 15, 2023, including English translation of summarizing section, 5 pages.

* cited by examiner

FIGURE 5

ANTAGONIST ANTI-NPR1 ANTIBODIES AND METHODS OF USE THEREOF

CROSS-REFERENCE TO RELATED APPLICATIONS

This application claims priority to U.S. Provisional Patent Application Nos. 63/286,476, filed Dec. 6, 2021, and 63/310,078, filed Feb. 14, 2022, the entire content of each of which is incorporated by reference herein.

REFERENCE TO A SEQUENCE LISTING XML

This application contains a Sequence Listing which has been submitted electronically in XML format. The Sequence Listing XML is incorporated herein by reference. Said XML file, created on Nov. 24, 2022, is named 40848_0112USU1_SL.xml and is 82,654 bytes in size.

FIELD OF THE DISCLOSURE

The present disclosure is related to antagonist antibodies and antigen-binding fragments of antibodies that specifically bind to natriuretic peptide receptor 1 (NPR1), and therapeutic and diagnostic methods of using those antibodies.

BACKGROUND OF THE DISCLOSURE

Natriuretic peptide receptor 1 (NPR1; also known as NPR-A) is a membrane-bound guanylate cyclase that mediates the intracellular conversion of guanosine triphosphate to cyclic guanosine monophosphate (cGMP) (Martinez-Rumayor, et al., 2008 Am J Cardio/101 (3a): 3-8). NPR1 is broadly expressed, including in the kidney, lungs, adrenal, vasculature, brain, liver, endothelial and adipose tissues and at lower levels in the heart. It is activated by binding to atrial natriuretic peptide (ANP) or brain natriuretic peptide (BNP). NPR1 activation and signaling stimulate many physiologic responses involving many tissues. The ANP-NPR1 system has been well studied for its role in vasorelaxation, natriuresis, diuresis, endothelial permeability and in non-cardiovascular functions like lipolysis and immune cell functions (Potter, 2011 Pharmacol. Ther. 130:71-82). NPR1 agonism results in alterations of systemic blood pressure (BP) through cGMP-mediated effects on intravascular volume, vasorelaxation, natriuresis, and diuresis.

Monoclonal antibodies to NPR1 were first described by Kitano, et al., in 1995 (Immunol. Lett. 47:215-22). Activating or agonist anti-NPR1 antibodies are disclosed in, for example, US Patent/Publication Nos. 9090695, 20160168251, and 20200123263, and in WO2010065293.

Hypotension, or low blood pressure, can be a relatively benign, asymptomatic condition, but it can become of concern, when the pumping pressure is not sufficient to perfuse key organs with oxygenated blood (Sharma, et al., updated 2021 Hypotension, available from www.ncbi.nlm.nih.gov/books/NBK499961/). Complications of untreated hypotension with poor cardiac output are severe and can even lead to death.

Disorders characterized by hypotension have a high unmet medical need for safe, long-acting therapies. Relatively few drugs increase blood pressure and intravascular volume. Most existing drugs have limitations, for example, oral agents have a short duration of action, necessitating multiple doses/day, and intravenous vasopressors require infusion in an ICU with frequent monitoring due to a narrow therapeutic index.

BRIEF SUMMARY OF THE DISCLOSURE

In one aspect, the present disclosure provides antagonist antibodies and antigen-binding fragments thereof that specifically bind the natriuretic peptide receptor 1 (NPR1) protein. In one embodiment, an isolated antibody or antigen-binding fragment thereof that binds specifically to natriuretic peptide receptor 1 (NPR1) protein is provided, wherein the antibody or antigen-binding fragment thereof binds to NPR1 and blocks NPR1. In a further embodiment, blocking NPR1 comprises inhibiting and/or blocking NPR1's signaling and/or activity. In certain embodiments, the anti-NPR1 antibodies are fully human antibodies that bind to NPR1 with high affinity and block NPR1. The antibodies of the present disclosure are useful, inter alia, for blocking or reducing NPR1 signaling and/or the hypotensive activity of NPR1 protein. In certain embodiments, the antibodies are useful in preventing, treating, or ameliorating at least one symptom or indication of a NPR1-associated disease or disorder, including hypotension, in a subject. In certain embodiments, the antibodies may be administered prophylactically or therapeutically to a subject having or at risk of having a NPR1-associated disease or disorder. In specific embodiments, the antibodies are used to increase systemic blood pressure in a subject suffering from low blood pressure. Such antibodies can be used as therapy for a disorder or condition associated with hypotension when administered to a subject in need thereof.

The antagonist antibodies disclosed herein bind to NPR1 with high affinity and have improved pharmacokinetic properties (as compared to standard-of-care drugs). A single dose of an antibody of the present disclosure led to sustained increase in blood pressure. Indeed, the antibodies disclosed herein are efficacious in increasing the blood pressure and maintaining the increased pressure for as long as 28 days when administered as a single dose. Such antibodies can be used to provide superior efficacy, along with less frequent dosing, in a subject with a NPR1-associated disease or disorder (e.g., hypotension).

The antibodies of the disclosure can be full-length (for example, an IgG1 or IgG4 antibody) or may comprise only an antigen-binding portion (for example, a Fab, F(ab') 2 or scFv fragment), and may be modified to affect functionality, e.g., to increase persistence in the host or to eliminate residual effector functions (Reddy, et al., 2000, J. Immunol. 164:1925-1933). In certain embodiments, the antibodies may be bispecific.

In a first aspect, the present disclosure provides isolated recombinant monoclonal antagonist antibodies or antigen-binding fragments thereof that bind specifically to NPR1.

In some embodiments, the antibodies are fully human monoclonal antibodies.

Exemplary anti-NPR1 antibodies of the present disclosure are listed in Tables 1 and 2 herein. Table 1 sets forth the amino acid sequence identifiers of the heavy chain variable regions (HCVRs), light chain variable regions (LCVRs), heavy chain complementarity determining regions (HCDRs) (HCDR1, HCDR2 and HCDR3), and light chain complementarity determining regions (LCDRs) (LCDR1, LCDR2 and LCDR3) of exemplary antibodies. Table 2 sets forth the nucleic acid sequence identifiers of the HCVRs, LCVRs, HCDR1, HCDR2 HCDR3, LCDR1, LCDR2 and LCDR3 of the exemplary antibodies.

The present disclosure provides antibodies, or antigen-binding fragments thereof, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present disclosure also provides antibodies, or antigen-binding fragments thereof, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present disclosure also provides antibodies, or antigen-binding fragments thereof, comprising a heavy chain variability region (HCVR) having an amino acid sequence selected from the group consisting of SEQ ID NOs: 2, 22, 38, and 55.

The present disclosure also provides antibodies, or antigen-binding fragments thereof, comprising a light chain variability region (LCVR) having an amino acid sequence selected from the group consisting of SEQ ID NOs: 10, 30, 46, and 63.

The present disclosure also provides antibodies, or antigen-binding fragments thereof, comprising three complementarity determining regions (CDRs) contained within a heavy chain variable region (HCVR) selected from the group consisting of SEQ ID NOs: 2, 22, 38, and 55; and three CDRs contained within a light chain variable region (LCVR) selected from the group consisting of SEQ ID NOs: 10, 30, 46, and 63.

The present disclosure also provides antibodies, or antigen-binding fragments thereof, comprising an HCVR and an LCVR amino acid sequence pair comprising any of the HCVR amino acid sequences listed in Table 1 paired with any of the LCVR amino acid sequences listed in Table 1. According to certain embodiments, the present disclosure provides antibodies, or antigen-binding fragments thereof, comprising an HCVR and LCVR amino acid sequence pair contained within any of the exemplary anti-NPR1 antibodies listed in Table 1. In certain embodiments, the HCVR and LCVR amino acid sequence pair is selected from one of SEQ ID NOs: 2 and 10 (e.g., mAb38067), SEQ ID NOs: 22 and 30 (e.g., mAb38072), SEQ ID NOs: 38 and 46 (e.g., mAb38090), and SEQ ID NOs: 55 and 63 (e.g., mAb22034).

The present disclosure also provides antibodies, or antigen-binding fragments thereof, comprising a HCVR and a LCVR, said HCVR comprising an amino acid sequence listed in Table 1 having no more than twelve amino acid substitutions, and/or said LCVR comprising an amino acid sequence listed in Table 1 having no more than ten amino acid substitutions. For example, the present disclosure provides antibodies or antigen-binding fragments thereof comprising a HCVR and a LCVR, said HCVR comprising an amino acid sequence listed in Table 1, said amino acid sequence having one, two, three, four, five, six, seven, eight, nine, ten, eleven or twelve amino acid substitutions. In another example, the present disclosure provides antibodies or antigen-binding fragments thereof comprising a HCVR and a LCVR, said LCVR comprising an amino acid sequence listed in Table 1, said amino acid sequence having one, two, three, four, five, six, seven, eight, nine or ten amino acid substitutions. In one embodiment, the present disclosure provides anti-NPR1 antibodies or antigen-binding fragments thereof comprising a HCVR and a LCVR, said HCVR comprising an amino acid sequence listed in Table 1, said amino acid sequence having at least one amino acid substitution, and/or said LCVR comprising an amino acid sequence listed in Table 1, said amino acid sequence having at least one amino acid substitution.

The present disclosure also provides antibodies, or antigen-binding fragments thereof, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present disclosure also provides antibodies, or antigen-binding fragments thereof, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present disclosure also provides antibodies, or antigen-binding fragments thereof, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present disclosure also provides antibodies, or antigen-binding fragments thereof, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present disclosure also provides antibodies, or antigen-binding fragments thereof, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present disclosure also provides antibodies, or antigen-binding fragments thereof, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

The present disclosure also provides antibodies, or antigen-binding fragments thereof, comprising:

(a) a heavy chain determining region (HCDR) 1 domain having an amino acid sequence selected from the group consisting of SEQ ID NOs: 4, 24, 40, and 57;

(b) a HCDR2 domain having an amino acid sequence selected from the group consisting of SEQ ID NOs: 6, 26, 42, and 59;

(c) a HCDR3 domain having an amino acid sequence selected from the group consisting of SEQ ID NOs: 8, 28, 44, ad 61;

(d) a light chain determining region (LCDR) 1 domain having an amino acid sequence selected from the group consisting of SEQ ID NOs: 12, 48, and 65;

(e) a LCDR2 domain having an amino acid sequence selected from the group consisting of AAS and GAS; and (f) a LCDR3 domain having an amino acid sequence selected from the group consisting of SEQ ID NOs: 16, 32, and 69.

The present disclosure also provides antibodies, or antigen-binding fragments thereof, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present disclosure provides antibodies, or antigen-binding fragments thereof, comprising an HCDR3/LCDR3 amino acid sequence pair contained within any of the exemplary anti-NPR1 antibodies listed in Table 1. In certain embodiments, the HCDR3/LCDR3 amino acid sequence pair is selected from the group consisting of SEQ ID NOs: 8/16 (e.g., mAb38067), 28/32 (e.g., mAb38072), 44/16 (e.g., mAb38090), and 61/69 (e.g., mAb22034).

The present disclosure also provides antibodies, or antigen-binding fragments thereof, comprising a HCVR and a LCVR, said HCVR comprising HCDR1 comprising an amino acid sequence differing from an amino acid sequence listed in Table 1 by 1 amino acid, HCDR2 comprising an amino acid sequence differing from an amino acid sequence listed in Table 1 by 1 amino acid, and HCDR3 comprising an amino acid sequence differing from an amino acid sequence listed in Table 1 by 1 amino acid. In certain embodiments, the present disclosure provides antibodies, or antigen-binding fragments thereof, comprising a HCVR and a LCVR, said LCVR comprising LCDR1 comprising an amino acid sequence differing from an amino acid sequence listed in Table 1 by 1 amino acid, LCDR2 comprising an amino acid sequence differing from an amino acid sequence listed in Table 1 by 1 amino acid, and LCDR3 comprising an amino acid sequence differing from an amino acid sequence listed in Table 1 by 1 amino acid. For example, the present disclosure provides antibodies, or antigen-binding fragments thereof, comprising a HCVR and a LCVR, said HCVR comprising HCDR1 comprising an amino acid sequence of SEQ ID NO: 24 or an amino acid sequence differing from SEQ ID NO: 24 by 1 amino acid, HCDR2 comprising an amino acid sequence of SEQ ID NO: 26 or an amino acid sequence differing from SEQ ID NO: 26 by 1 amino acid, and HCDR3 comprising an amino acid sequence of SEQ ID NO: 28 or an amino acid sequence differing from SEQ ID NO: 28 by 1 amino acid. In another exemplary embodiment, the present disclosure provides antibodies, or antigen-binding fragments thereof, comprising a HCVR and a LCVR, said LCVR comprising LCDR1 comprising an amino acid sequence of SEQ ID NO: 12 or an amino acid sequence differing from SEQ ID NO: 12 by 1 amino acid, LCDR2 comprising an amino acid sequence of AAS or an amino acid sequence differing from AAS by 1 amino acid, and LCDR3 comprising an amino acid sequence of SEQ ID NO: 32 or an amino acid sequence differing from SEQ ID NO: 32 by 1 amino acid.

The present disclosure also provides antibodies, or antigen-binding fragments thereof, comprising a set of six CDRs (i.e., HCDR1-HCDR2-HCDR3-LCDR1-LCDR2-LCDR3) contained within any of the exemplary antibodies listed in Table 1. In certain embodiments, the HCDR1-HCDR2-HCDR3-LCDR1-LCDR2-LCDR3 amino acid sequence set is selected from the group consisting of SEQ ID NO: 4-SEQ ID NO: 6-SEQ ID NO: 8-SEQ ID NO: 12-AAS-SEQ ID NO: 16 (e.g., mAb38067), SEQ ID NO: 24-SEQ ID NO: 26-SEQ ID NO: 28-SEQ ID NO: 12-AAS-SEQ ID NO: 32 (e.g., mAb38072), SEQ ID NO: 40-SEQ ID NO: 42-SEQ ID NO:44-SEQ ID NO: 48-AAS-SEQ ID NO: 16 (e.g., mAb38090), and SEQ ID NO: 57-SEQ ID NO: 59-SEQ ID NO: 61-SEQ ID NO: 65-GAS-SEQ ID NO: 69 (e.g., mAb22034).

In a related embodiment, the present disclosure provides antibodies, or antigen-binding fragments thereof, comprising a set of six CDRs (i.e., HCDR1-HCDR2-HCDR3-LCDR1-LCDR2-LCDR3) contained within an HCVR and LCVR amino acid sequence pair as defined by any of the exemplary antibodies listed in Table 1. For example, the present disclosure includes antibodies, or antigen-binding fragments thereof, comprising the HCDR1-HCDR2-HCDR3-LCDR1-LCDR2-LCDR3 amino acid sequences set contained within an HCVR and LCVR amino acid sequence pair selected from the group consisting of SEQ ID NOs: 8 and 16 (e.g., mAb38067), SEQ ID NOs: 28 and 32 (e.g., mAb38072), SEQ ID NOs: 44 and 16 (e.g., mAb38090), and SEQ ID NOs: 61 and 69 (e.g., mAb22034). In a related embodiment, the present disclosure provides antibodies, or antigen-binding fragments thereof, comprising a heavy chain variable region (HCVR) and light chain variable region (LCVR) amino acid sequence pair selected from the group consisting of SEQ ID NOs: 2 and 10, SEQ ID NOs: 22 and 30, SEQ ID NOs: 38 and 46, and SEQ ID NOs: 55 and 63.

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani, et al., *J. Mol. Biol.* 273:927-948 (1997); and Martin, et al., *Proc. Natl. Acad. Sci. USA* 86:9268-9272 (1989). Public databases are also available for identifying CDR sequences within an antibody.

In certain embodiments, the present disclosure includes an antibody or antigen-binding fragment thereof that binds specifically to NPR1, wherein the antibody or antigen-binding fragment thereof comprises a heavy chain and light chain, wherein the light chain is selected from the group consisting of SEQ ID NOs: 20, 36, 53, and 73.

In additional embodiments, the present disclosure includes an antibody or antigen-binding fragment thereof that binds specifically to NPR1, wherein the antibody or antigen-binding fragment thereof comprises a heavy chain and a light chain, wherein the heavy chain is selected from the group consisting of SEQ ID NOs: 18, 34, 51 and 71; and the light chain is selected from the group consisting of SEQ ID NOs: 20, 36, 53, and 73.

In additional embodiments, the present disclosure includes an antibody or antigen-binding fragment thereof that binds specifically to NPR1, wherein the antibody or antigen-binding fragment thereof binds to residues in the lower lobe of the extracellular domain of NPR1. In still further embodiments, the present disclosure includes an antibody or antigen-binding fragment thereof that binds specifically to NPR1, wherein the antibody or antigen-binding fragment thereof interacts with at least one of the NPR1 residues selected from the group consisting of Arg143, Leu144, Glu384, Leu401, Val402, Ala103, Ser405, Gly406, Arg407, Lys408, Trp411, Leu413, Gly414, Tyr415, and Pro416.

In additional embodiments, the present disclosure includes an antibody or antigen-binding fragment thereof that binds specifically to NPR1, wherein the antibody or antigen-binding fragment thereof comprises a heavy chain and a light chain, wherein the heavy chain comprises an amino acid sequence of SEQ ID NO: 18; and the light chain comprises an amino acid sequence of SEQ ID NO: 20.

In additional embodiments, the present disclosure includes an antibody or antigen-binding fragment thereof that binds specifically to NPR1, wherein the antibody or antigen-binding fragment thereof comprises a heavy chain and a light chain, wherein the heavy chain comprises an amino acid sequence of SEQ ID NO: 34; and the light chain comprises an amino acid sequence of SEQ ID NO: 36.

In additional embodiments, the present disclosure includes an antibody or antigen-binding fragment thereof that binds specifically to NPR1, wherein the antibody or antigen-binding fragment thereof comprises a heavy chain and a light chain, wherein the heavy chain comprises an amino acid sequence of SEQ ID NO: 51; and the light chain comprises an amino acid sequence of SEQ ID NO: 53.

In additional embodiments, the present disclosure includes an antibody or antigen-binding fragment thereof that binds specifically to NPR1, wherein the antibody or antigen-binding fragment thereof comprises a heavy chain and a light chain, wherein the heavy chain comprises an amino acid sequence of SEQ ID NO: 71; and the light chain comprises an amino acid sequence of SEQ ID NO: 73.

In certain embodiments, the present disclosure includes an antibody or antigen-binding fragment thereof that binds specifically to NPR1, wherein the antibody or antigen-binding fragment thereof comprises three heavy chain complementarity determining regions (CDRs) (HCDR1, HCDR2 and HCDR3) contained within a heavy chain variable region (HCVR) and three light chain CDRs (LCDR1, LCDR2 and LCDR3) contained within a light chain variable region (LCVR), wherein the HCVR comprises: (i) an amino acid sequence selected from the group consisting of SEQ ID NOs: 2, 22, 38, and 55; (ii) an amino acid sequence having at least 90% identity to the amino acid sequence selected from the group consisting of SEQ ID NOs: 2, 22, 38, and 55; (iii) an amino acid sequence having at least 95% identity to the amino acid sequence selected from the group consisting of SEQ ID NOs: 2, 22, 38, and 55; or (iv) an amino acid sequence selected from the group consisting of SEQ ID NOs: 2, 22, 38, and 55, said amino acid sequence having no more than 12 amino acid substitutions; and the LCVR comprises: (a) an amino acid sequence selected from the group consisting of SEQ ID NOs: 10, 30, 46, and 63; (b) an amino acid sequence having at least 90% identity to the amino acid sequence selected from the group consisting of SEQ ID NOs: 10, 30, 46, and 63; (c) an amino acid sequence having at least 95% identity to the amino acid sequence selected from the group consisting of SEQ ID NOs: 10, 30, 46, and 63; or (d) an amino acid sequence selected from the group consisting of SEQ ID NOs: 10, 30, 46, and 63, said amino acid sequence having no more than 10 amino acid substitutions.

In certain preferred embodiments, the present disclosure includes antibodies that bind specifically to NPR1 in an antagonist manner, i.e., block or reduce NPR1 binding and/or activity.

The present disclosure includes anti-NPR1 antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield, et al. (2002) JBC 277:26733). In other applications, modification of galactosylation can be made in order to modify complement dependent cytotoxicity (CDC).

In certain embodiments, the present disclosure provides antibodies and antigen-binding fragments thereof that exhibit pH-dependent binding to NPR1. For example, the present disclosure includes antibodies and antigen-binding fragment thereof that bind NPR1 with higher affinity at neutral pH than at basic pH (i.e., reduced binding at basic pH).

The present disclosure also provides for antibodies and antigen-binding fragments thereof that compete for specific binding to NPR1 with an antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

The present disclosure also provides antibodies and antigen-binding fragments thereof that cross-compete for binding to NPR1 with a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

The present disclosure also provides antibodies and antigen-binding fragments thereof that bind to the same epitope as a reference antibody or antigen-binding fragment thereof comprising three CDRs of a HCVR and three CDRs of a LCVR, wherein the HCVR and LCVR each has an amino acid sequence selected from the HCVR and LCVR sequences listed in Table 1.

In certain embodiments, the antibodies or antigen-binding fragments of the present disclosure are bispecific comprising a first binding specificity to a first epitope of NPR1 and a second binding specificity to a second epitope of NPR1 wherein the first and second epitopes are distinct and non-overlapping.

In certain embodiments, the present disclosure provides an isolated antagonist anti-NPR1 antibody or antigen-binding fragment thereof, wherein the antibody or antigen-binding fragment thereof has one or more of the following characteristics: (a) is a fully human monoclonal antibody; (b) binds to human NPR1 at 25° C. and at 37° C. with a dissociation constant ($K_D$) of less than 1.7 nM, as measured in a surface plasmon resonance assay; (c) binds to monkey NPR1 at 25° C. and 37° C. with a $K_D$ of less than 1.99 nM, as measured in a surface plasmon resonance assay; (d) binds to human NPR1 in the presence of ANP at 25° C. and at 37° C. with a $K_D$ of less than 1.52 nM, as measured in a surface plasmon resonance assay; (e) inhibits ligand-induced NPR1 activation (for example, induced by ANP or BNP), as measured by cGMP accumulation assay; (f) binds to human NPR1 in the presence or absence of ANP or BNP with an $EC_{50}$ of less than 2.9 nM, as measured by electrochemiluminescence-based immunoassay; (g) binds to monkey NPR1 in the presence or absence of ANP or BNP with an $EC_{50}$ of less than 4.2 nM, as measured by electrochemiluminescence-based immunoassay; (h) increases the systemic blood pressures (including systolic, diastolic, mean arterial, and pulse pressures) when administered to normotensive and hypotensive mice, wherein the increase in systemic blood pressures lasts for up to about 28 days upon administration of a single dose; (i) increases the systemic blood pressures when administered to ANP overexpression-induced hypotensive mice, wherein the increase in systemic blood pressures lasts for up to about 28 days upon administration of a single dose; (j) increases systemic blood pressures in LPS-induced hypotensive mice; and (k) comprises a HCVR comprising an amino acid sequence selected from the group consisting of HCVR sequence listed in Table 1 and a LCVR comprising an amino acid sequence selected from the group consisting of LCVR sequences listed in Table 1.

In a second aspect, the present disclosure provides nucleic acid molecules encoding anti-NPR1 antibodies or portions thereof. In certain embodiments, an isolated polynucleotide molecule is provided comprising a polynucleotide sequence that encodes a heavy chain variable region (HCVR) of an isolated antibody or antigen-binding fragment thereof that binds specifically to natriuretic peptide receptor 1 (NPR1) protein, wherein the antibody or antigen-binding fragment thereof binds to NPR1 and blocks NPR1. In additional embodiments, an isolated polynucleotide molecule is provided comprising a polynucleotide sequence that encodes a light chain variable region (LCVR) of an isolated antibody or antigen-binding fragment thereof that binds specifically to natriuretic peptide receptor 1 (NPR1) protein, wherein the antibody or antigen-binding fragment thereof binds to NPR1 and blocks NPR1. For example, the present disclosure provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present disclosure also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present disclosure also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present disclosure also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present disclosure also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present disclosure also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present disclosure also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present disclosure also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present disclosure also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary antibodies listed in Table 1.

The present disclosure also provides nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary antibodies listed in Table 1.

The present disclosure also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 1, or a substantially similar sequence thereof having at least 90%, at least 95%, at least 98% or at least 99% sequence identity thereto. In certain embodiments according to this aspect of the disclosure, the nucleic acid molecule encodes an HCVR and LCVR, wherein the HCVR and LCVR are both derived from the same anti-NPR1 antibody listed in Table 1.

In a related aspect, the present disclosure provides a vector comprising a polynucleotide molecule encoding an HCVR of an isolated antibody or antigen-binding fragment thereof that binds specifically to natriuretic peptide receptor 1 (NPR1) protein, wherein the antibody or antigen-binding fragment thereof binds to NPR1 and blocks NPR1. In another related aspect, the present disclosure provides a vector comprising a polynucleotide molecule encoding an LCVR of an isolated antibody or antigen-binding fragment thereof that binds specifically to natriuretic peptide receptor 1 (NPR1) protein, wherein the antibody or antigen-binding fragment thereof binds to NPR1 and blocks NPR1. In yet another related aspect, the present disclosure provides recombinant expression vectors capable of expressing a polypeptide comprising a heavy and/or light chain variable region of an antibody. For example, the present disclosure includes recombinant expression vectors comprising any of the nucleic acid molecules mentioned above, i.e., nucleic acid molecules encoding any of the HCVR, LCVR, and/or CDR sequences as set forth in Table 2. In certain embodiments, the present disclosure provides expression vectors comprising: (a) a nucleic acid molecule comprising a nucleic acid sequence encoding a HCVR of an antibody that binds NPR1, wherein the HCVR comprises an amino acid sequence selected from the group consisting of sequences listed in Table 1; and/or (b) a nucleic acid molecule comprising a nucleic acid sequence encoding a LCVR of an antibody that binds NPR1, wherein the LCVR comprises an amino acid sequence selected from the group consisting of sequences listed in Table 1. Also included within the scope of the present disclosure are host cells comprising a vector according to the disclosure, as well as methods of producing the antibodies or portions thereof by culturing the host cells under conditions permitting production of the antibodies or antibody fragments, and recovering the antibodies and antibody fragments so produced. In certain embodiments, the method of producing according to the disclosure further comprises formulating the antibody or antigen-binding fragment thereof as a pharmaceutical composition comprising an acceptable carrier. In certain embodiments, the host cells comprise a mammalian cell or a prokaryotic cell. In certain embodiments, the host cell is a Chinese Hamster Ovary (CHO) cell or an *Escherichia coli* (*E. coli*) cell. In certain embodiments, the present disclosure provides methods of producing an antibody or antigen-binding fragment thereof of the disclosure, the methods comprising introducing into a host cell an expression vector comprising a nucleic acid sequence encoding a HCVR and/or LCVR of an antibody or antigen-binding fragment thereof of the disclosure operably linked to a promoter; culturing the host cell under conditions favorable for expression of the nucleic acid sequence; and isolating the antibody or antigen-binding fragment thereof from the culture medium and/or host cell. The isolated antibody or antigen-binding fragment thereof may be purified using any of the methods known in prior art.

In a third aspect, the disclosure provides a pharmaceutical composition comprising an antibody or antigen-binding fragment thereof that binds specifically to natriuretic peptide receptor 1 (NPR1) protein, wherein the antibody or antigen-binding fragment thereof binds to NPR1 and blocks NPR1, and a pharmaceutically acceptable carrier. In another embodiment, the pharmaceutical composition comprises a therapeutically effective amount of at least one recombinant monoclonal antibody or antigen-binding fragment thereof that specifically binds NPR1 and a pharmaceutically acceptable carrier. In a related aspect, the disclosure features a composition that is a combination of an anti-NPR1 antibody and a second therapeutic agent or therapy. In one embodiment, the second therapeutic agent or therapy is any agent or therapy that is advantageously combined with an anti-NPR1 antibody. Exemplary agents or therapies that may be advantageously combined with an antagonist anti-NPR1 antibody include, without limitation, other agents that bind and/or block NPR1 signaling and/or activity (including other antibodies or antigen-binding fragments thereof, etc.) and/or agents which do not directly bind NPR1 but nonetheless treat or ameliorate at least one symptom or indication of a NPR1-associated disease or disorder (disclosed elsewhere herein). Additional combination therapies and co-formulations involving the anti-NPR1 antibodies of the present disclosure are disclosed elsewhere herein.

In a fourth aspect, the disclosure provides therapeutic methods for treating a disease or disorder associated with NPR1 in a subject using an anti-NPR1 antibody or antigen-binding portion of an antibody of the disclosure, wherein the therapeutic methods comprise administering a pharmaceutical composition comprising an therapeutically effective amount of an antibody or antigen-binding fragment of an antibody according to the disclosure to the subject in need thereof. In certain embodiments, the disorder treated is any disease or condition that is improved, ameliorated, inhibited or prevented by blocking of NPR1 activity (e.g., hypotension). In certain embodiments, the NPR1-associated disease or disorder is selected from the group consisting of hypotension, circulatory shock, septic shock, neurogenic orthostatic hypotension, postural orthostatic tachycardia syndrome (POTS), heart failure, cardiogenic shock, obesity, renal failure, chronic kidney disease, macular edema, glaucoma, stroke, lung disorders, pulmonary fibrosis, inflammation, asthma, skeletal growth disorders, bone fractures, diabetes, hypoglycemia, and cancer.

In certain embodiments, the disclosure provides methods to prevent, or treat a NPR1-associated disease or disorder comprising administering a therapeutically effective amount of an anti-NPR1 antibody or antigen-binding fragment thereof of the disclosure to a subject in need thereof. In some embodiments, the antibody or antigen-binding fragment thereof may be administered prophylactically or therapeutically to a subject (for example, to a subject having or at risk of having a NPR1-associated disease or disorder). In certain embodiments, the antibody or antigen-binding fragment, or the composition comprising an antibody or antigen-binding fragment thereof, according to the disclosure, is administered in combination with a second therapeutic agent or therapy. The second therapeutic agent or therapy may, in certain embodiments, be selected from the group consisting of an angiogenesis inhibitor, a vasoconstrictor/vasopressor, an immunosuppressant, ascorbic acid, a calcineurin inhibitor, a corticosteroid, a VEGF inhibitor, a decongestant, an antidepressant, hormonal birth control, a stimulant (including cardiac stimulant), caffeine, extracorporeal membrane oxygenation, ventricular assist device, intra-aortic balloon pump, a lifestyle modification, a dietary supplement, an anti-microbial drug, insulin, and an anti-inflammatory drug. In certain embodiments, the second therapeutic agent or therapy may be an agent or therapy that helps to counteract or reduce any possible side effect(s) associated with an antibody or antigen-binding fragment thereof of the disclosure, if such side effect(s) should occur. The antibody or fragment thereof, or the composition comprising an antibody or antigen-binding fragment thereof, according to the disclosure, may be administered subcutaneously, intravenously, intradermally, intraperitoneally, orally, or intramuscularly. The antibody or fragment thereof may be administered at a dose of about 0.1 mg/kg of body weight to about 100 mg/kg of body weight of the subject. In certain embodiments, an antibody of the present disclosure may be administered at one or more doses comprising between 10 mg to 600 mg.

The present disclosure also includes use of an anti-NPR1 antibody or antigen-binding fragment thereof of the disclosure in the manufacture of a medicament for the treatment of a disease or disorder that would benefit from the blocking of NPR1 binding and/or activity.

Other embodiments will become apparent from a review of the ensuing detailed description.

BRIEF DESCRIPTION OF THE FIGURES

FIG. 5 shows the effects of NPR1 antagonist mAb's on systolic blood pressures in normotensive NPR1$^{hu/hu}$ mice-single 25 mg/kg dose. Telemetered normotensive NPR1$^{hu/hu}$ mice were randomized into groups based on body weight. Animals were given a single 25 mg/kg intravenous injection of an NPR1 antagonist mAb or PBS as described in Table 25. All values are mean±SEM, n=6 per group.

DETAILED DESCRIPTION

Figures 1A, 1B:
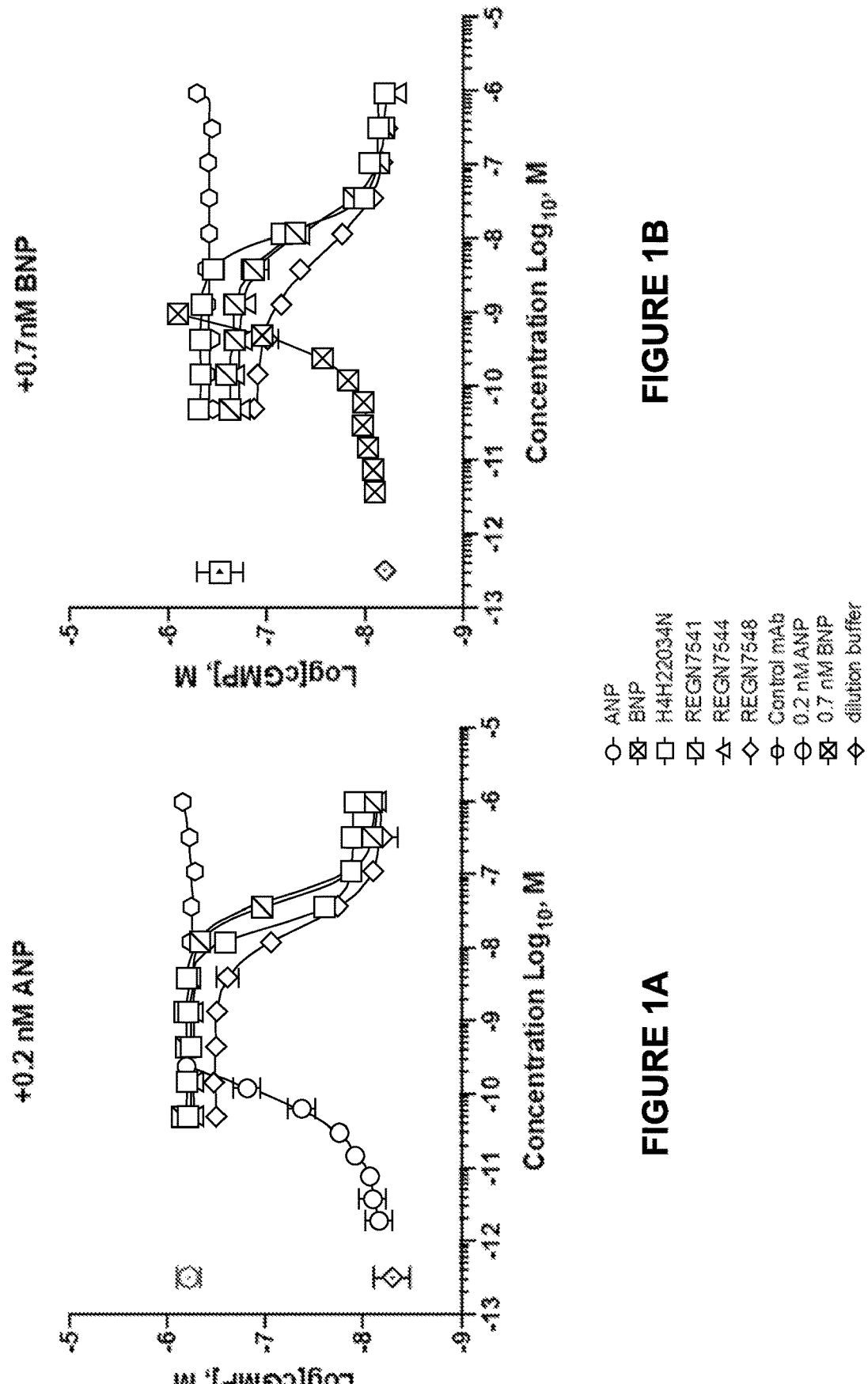
FIGS. 1A and 1B show that anti-NPR1 antibodies inhibited (FIG. 1A) ANP and (FIG. 1B) BNP induced hNPR1 activation. Cells were pre-treated with increasing concentrations of anti-NPR1 antibodies, control mAb, or dilution buffer alone for 15 minutes at 37° C., followed by increasing concentrations of ANP, BNP, 0.2 nM ANP or 0.7 nM BNP for 30 minutes at 37° C. Experiment was performed in duplicate. Open symbols indicate conditions when no test article or only constant concentration of ANP or BNP was added, and closed symbols indicate conditions when the test article was added in a range of concentrations; dilution buffer: OptiMEM with 0.1% FBS.
Figures 2A, 2B:
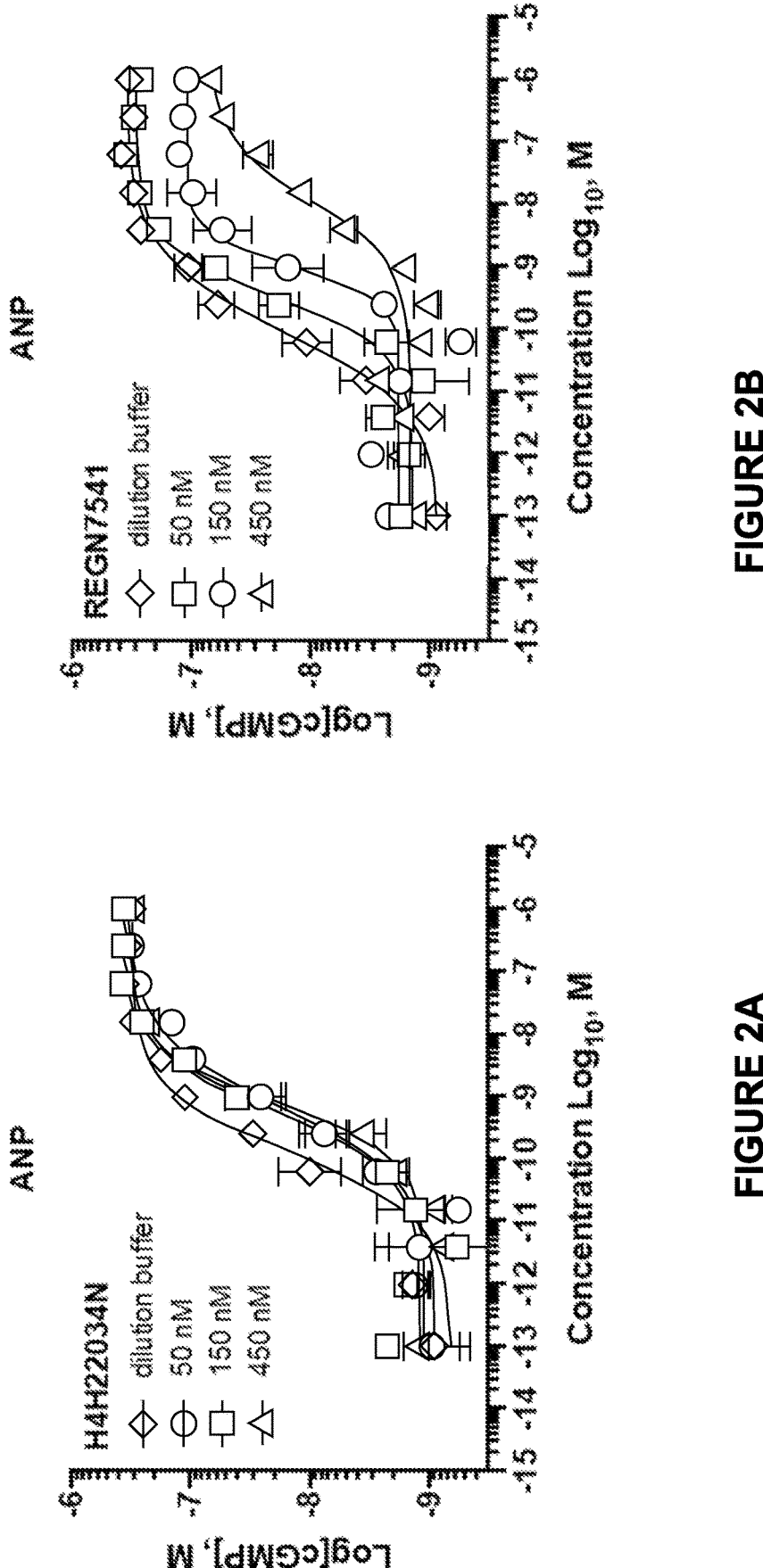
FIGS. 2A-2E show the non-competitive inhibition of ANP-mediated activation of NPR1 by (FIG. 2A) H4H22034N, (FIG. 2B) REGN7541, (FIG. 2C) REGN7544, and (FIG. 2D) REGN7548 with HEK293/hNPR1 cells. The data of the panel of FIGS. 2A to 2D were analyzed in Schild plot analysis (FIG. 2E) to evaluate the Schild slope for each of the anti-NPR1 antibodies. The detection of fluorescence intensity and cGMP concentration were calculated as described in the experimental procedure. Experiment was performed in duplicate. No ligand stimulation for each indicated antibody concentration was plotted at 0.1 pM and included in the Schild plot analysis. Open symbols indicate conditions of ANP alone without test article; closed symbols indicate conditions when the test article was added at indicated concentrations of 50 nM, 150 nM, or 450 nM with ANP in a range of concentrations of 1 pM to 1 μM; dilution buffer: OptiMEM with 0.1% FBS; CR: concentration ratio.
Figures 2C, 2D:
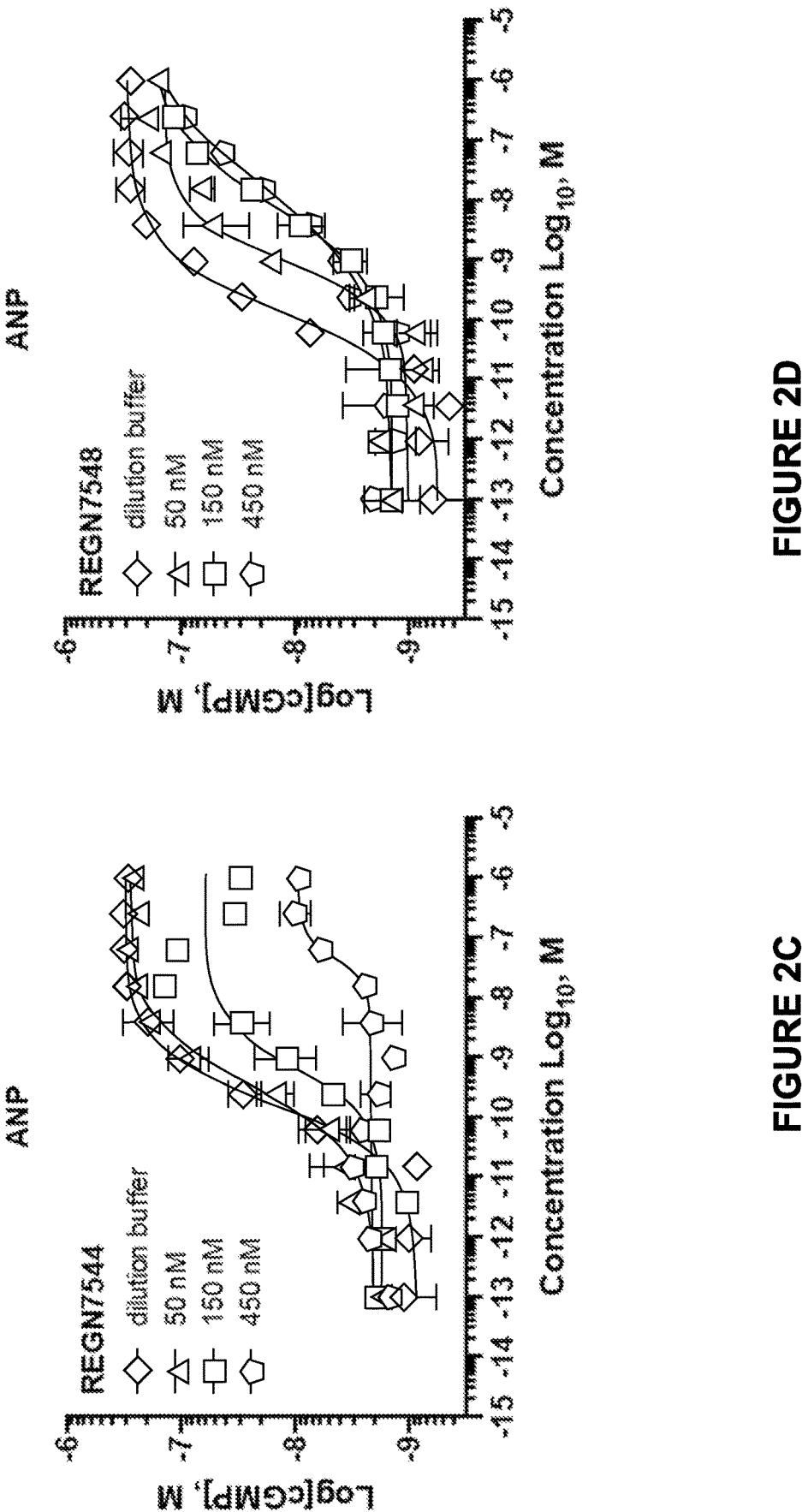
Figure 2E:
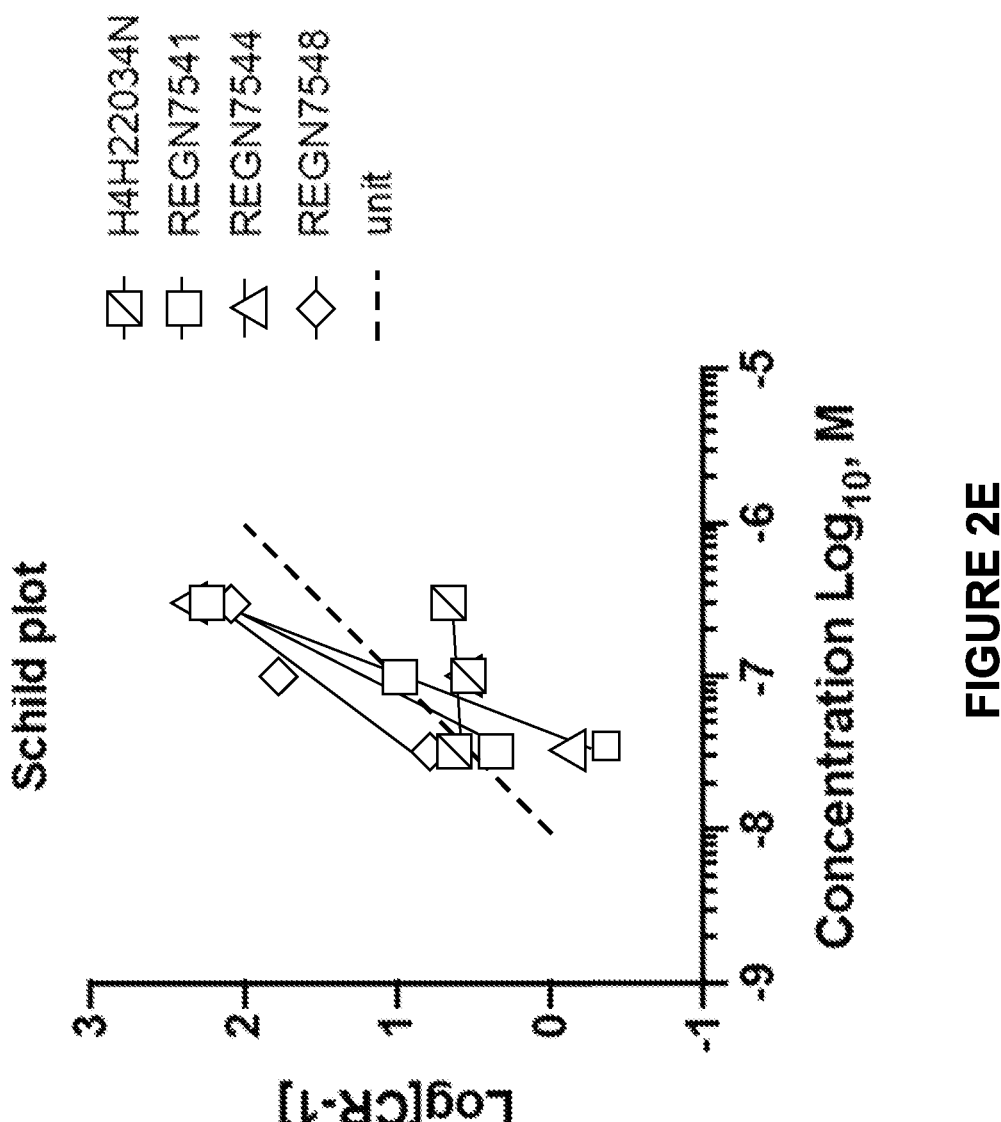

Before the present methods are described, it is to be understood that this disclosure is not limited to particular methods, and experimental conditions described, as such methods and conditions may vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, preferred methods and materials are now described. All publications mentioned herein are incorporated herein by reference in their entirety.

Definitions

The term "NPR1", also called "NPRA" refers to natriuretic peptide receptor 1 (also known as natriuretic peptide receptor A). NPR1 is a homodimeric transmembrane guanylate cyclase, an enzyme that catalyzes cGMP synthesis. NPR1 is the receptor for both atrial (ANP) and brain (BNP) natriuretic peptides and undergoes conformational changes in the extracellular domain upon ligand binding (Ogawa, et al., 2004 *J. Biol. Chem.* 279:28625-31). The protein has 4 distinct regions comprising an extracellular ligand-binding domain, a single transmembrane-spanning region, an intracellular protein kinase-like homology domain and a guanylyl cyclase catalytic domain. The amino acid sequence of full-length NPR1 protein is exemplified by the amino acid sequence provided in UniProtKB/Swiss-Prot as accession number P16066.1. The term "NPR1" includes recombinant NPR1 protein or a fragment thereof. The term also encompasses NPR1 protein or a fragment thereof coupled to, for example, histidine tag, mouse or human Fc, or a signal sequence such as ROR1 (for example, SEQ ID NOs: 74-78).

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g., IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region (CL). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the disclosure, the FRs of the antibody (or antigen-binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan, et al., (1995 *FASEB J.* 9:133-139), analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos, et al., 2002 *J Mol Biol* 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human anti-NPR1 monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present disclosure includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments that comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic biological properties, reduced immunogenicity, etc. Antibodies and antigen-binding fragments obtained in this general manner are encompassed within the present disclosure.

The present disclosure also includes fully human anti-NPR1 monoclonal antibodies comprising variants of any of the HCVR, LCVR, and/or CDR amino acid sequences disclosed herein having one or more conservative substitutions. For example, the present disclosure includes anti-NPR1 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", or "fully human antibody", as used herein, is intended to include antibodies having variable and constant regions derived from human germline immunoglobulin sequences. The human mAbs of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", or "fully human antibody", as used herein, is not intended to include mAbs in which CDR sequences derived from the germline of another mammalian species (e.g., mouse), have been grafted onto human FR sequences. The term includes antibodies that are recombinantly produced in a non-human mammal, or in cells of a non-human mammal. The term is not intended to include antibodies isolated from or generated in a human subject.

The term "recombinant", as used herein, refers to antibodies or antigen-binding fragments thereof of the disclosure created, expressed, isolated or obtained by technologies or methods known in the art as recombinant DNA technology which include, e.g., DNA splicing and transgenic expression. The term refers to antibodies expressed in a non-human mammal (including transgenic non-human mammals, e.g., transgenic mice), or a cell (e.g., CHO cells) expression system or isolated from a recombinant combinatorial human antibody library.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1\times10^{-8}$ M or less (e.g., a smaller Kp denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to NPR1. Moreover, multi-specific antibodies that bind to one domain in NPR1 and one or more additional antigens or a bi-specific that binds to two different regions of NPR1 are nonetheless considered antibodies that "specifically bind", as used herein.

The term "high affinity" antibody refers to those mAbs having a binding affinity to NPR1, expressed as $K_D$, of at least $10^{-8}$ M; preferably $10^{-9}$ M; more preferably 10-10M, even more preferably $10^{-11}$ M, as measured by surface plasmon resonance, e.g., BIACORE™ or solution-affinity ELISA.

By the term "slow off rate", "Koff" or "kd" is meant an antibody that dissociates from NPR1, with a rate constant of $1\times10^{-3}$ s$^{-1}$ or less, preferably $1\times10^{-4}$ s$^{-1}$ or less, as determined by surface plasmon resonance, e.g., BIACORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to NPR1 protein.

In specific embodiments, antibody or antibody fragments of the disclosure may be conjugated to a moiety such a ligand or a therapeutic moiety ("immunoconjugate"), a second anti-NPR1 antibody, or any other therapeutic moiety useful for treating a NPR1-associated disease or disorder.

An "isolated antibody", as used herein, is intended to refer to an antibody that is substantially free of other antibodies (Abs) having different antigenic specificities (e.g., an isolated antibody that specifically binds NPR1, or a fragment thereof, is substantially free of Abs that specifically bind antigens other than NPR1.

An "antagonist antibody", as used herein (or an "antibody that blocks or reduces NPR1 activity"), is intended to refer to an antibody whose binding to NPR1 results in the blocking or reduction of NPR1 signaling and/or at least one biological activity of NPR1. For example, an antagonist anti-NPR1 antibody may increase systemic blood pressure upon administration to a subject in need thereof. The anti-NPR1 antibodies disclosed herein are antagonist antibodies.

An "activating antibody" or an "agonist antibody", as used herein (or an "antibody that increases or potentiates NPR1 activity" or "an antibody that stabilizes the activated conformation"), is intended to refer to an antibody whose binding to NPR1 results in activation of at least one biological activity of NPR1. For example, an activating anti-NPR1 antibody or an agonist anti-NPR1 antibody may decrease systemic blood pressure upon administration to a subject in need thereof.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "cross-competes", as used herein, means an antibody or antigen-binding fragment thereof binds to an antigen and inhibits or blocks the binding of another antibody or antigen-binding fragment thereof. The term also includes competition between two antibodies in both orientations, i.e., a first antibody that binds and blocks binding of second antibody and vice-versa. In certain embodiments, the first antibody and second antibody may bind to the same epitope. Alternatively, the first and second antibodies may bind to different, but overlapping epitopes such that binding of one inhibits or blocks the binding of the second antibody, e.g., via steric hindrance. Cross-competition between antibodies may be measured by methods known in the art, for example, by a real-time, label-free bio-layer interferometry assay. Cross-competition between two antibodies may be expressed as the binding of the second antibody that is less than the background signal due to self-self binding (wherein first and second antibodies is the same antibody). Cross-competition between 2 antibodies may be expressed, for example, as % binding of the second antibody that is less than the baseline self-self background binding (wherein first and second antibodies is the same antibody).

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson, (1994) *Methods Mol. Biol.* 24:307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet, et al., (1992) *Science* 256:1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT, which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the disclosure to a database containing a large number of sequences from different organisms is the computer program BLAST, especially BLASTP or TBLASTN, using default parameters. See, e.g., Altschul, et al., (1990) *J. Mol. Biol.* 215:403-410 and (1997) *Nucleic Acids Res.* 25:3389-3402, each of which is herein incorporated by reference.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding). As used herein, the phrase refers to an amount that blocks NPR1 (e.g., NPR1 signaling, NPR1 activity) and/or that increases systemic blood pressure.

As used herein, the term "subject" refers to an animal, preferably a mammal, more preferably a human, in need of amelioration, prevention and/or treatment of a NPR1-associated disease or disorder such as hypotension. The term includes human subjects who have or are at risk of having such a disease or disorder.

As used herein, the terms "treat", "treating", or "treatment" refer to the reduction or amelioration of the severity of at least one symptom or indication of a NPR1-associated disease or disorder due to the administration of a therapeutic agent such as an antagonist antibody of the present disclosure to a subject in need thereof. The terms include inhibition of progression of disease or of worsening of a symptom/indication. The terms also include positive prognosis of disease, i.e., the subject may be free of disease or may have reduced disease upon administration of a therapeutic agent such as an antibody of the present disclosure. The therapeutic agent may be administered at a therapeutic dose to the subject. The disorder or disease may include hypotension and/or a disorder or disease associated with hypotension and/or hypotension associated with a disease or disorder, for example, septic shock and neurodegenerative disease. The disorder or disease may also include postural orthostatic tachycardia syndrome (POTS).

The terms "prevent", "preventing" or "prevention" refer to inhibition of manifestation of a NPR1-associated disease or disorder such as hypotension or any symptoms or indications of such a disease or disorder upon administration of an antibody of the present disclosure.

As used herein, the phrase "blood pressure" may refer to any one of systolic blood pressure, diastolic blood pressure, mean arterial pressure (area under the arterial pressure/time curve, divided by the cardiac cycle duration), and pulse pressure (difference between systolic and diastolic pressures). Methods for measurement of blood pressure are known in the art. Blood pressure is measured in units of millimeters of mercury (mm Hg) and is usually expressed in terms of systolic (blood) pressure over diastolic (blood) pressure. Measurement methods include auscultatory, oscillometric, ultrasound, finger cuff methods. It can generally be measured, for example, using a digital blood pressure monitor or a sphygmomanometer.

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to NPR1 protein. An antibody fragment may include a Fab fragment, a F(ab') 2 fragment, a Fv fragment, a dAb fragment, a fragment containing a CDR, or an isolated CDR. In certain embodiments, the term "antigen-binding fragment" refers to a polypeptide fragment of a multi-specific antigen-binding molecule. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F (ab') 2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$—$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H1$; (ii) $V_H$-$C_H2$; (iii) $V_H$-$C_H3$; (iv) $V_H$-$C_H1$-$C_H2$; (V) $V_H$-$C_H1$-$C_H2$-$C_H3$; (Vi) $V_H$-$C_H2$-$C_H3$; (vii) $V_H$-CL; (viii) $V_L$-$C_H1$; (ix) $V_L$-$C_H2$; (X) $V_L$-$C_H3$; (Xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-CL. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present disclosure may comprise a homo-dimer or heterodimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bispecific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present disclosure using routine techniques available in the art.

Preparation of Human Antibodies

Methods for generating human antibodies in transgenic mice are known in the art. Any such known methods can be used in the context of the present disclosure to make human antibodies that specifically bind to NPR1.

An immunogen comprising any one of the following can be used to generate antibodies to NPR1 protein. In certain embodiments, the antibodies of the disclosure are obtained from mice immunized with a full length, native NPR1 protein (See, for example, UniProtKB/Swiss-Prot accession number P16066.1) or with DNA encoding the protein or fragment thereof. Alternatively, the protein or a fragment thereof may be produced using standard biochemical techniques and modified and used as immunogen.

In some embodiments, the immunogen may be a recombinant NPR1 protein or fragment thereof expressed in *E. coli* or in any other eukaryotic or mammalian cells such as Chinese hamster ovary (CHO) cells (for example, SEQ ID NOs: 74-78)

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to NPR1 are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the disclosure, for example wild-type or modified IgG1 or IgG4. While the constant region selected may vary according to specific use, high affinity antigen-binding and target specificity characteristics reside in the variable region.

Bioequivalents

The antagonist anti-NPR1 antibodies and antibody fragments of the present disclosure encompass proteins having amino acid sequences that vary from those of the described antibodies, but that retain the ability to bind NPR1 protein. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present disclosure encompass sequences that comprise one or more additions, deletions, or substitutions of nucleotides when compared to the disclosed sequence, but that encode an antibody or antibody fragment that is essentially bioequivalent to an antibody or antibody fragment of the disclosure.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, or potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the disclosure may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Anti-NPR1 Antibodies Comprising Fc Variants

According to certain embodiments of the present disclosure, anti-NPR1 antibodies are provided comprising an Fc domain comprising one or more mutations which enhance or diminish antibody binding to the FcRn receptor, e.g., at acidic pH as compared to neutral pH. For example, the present disclosure includes anti-NPR1 antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 2591 (e.g., V2591), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present disclosure includes anti-NPR1 antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 2571 and 3111 (e.g., P2571 and Q3111); 2571 and 434H (e.g., P2571 and N434H); 376V and 434H (e.g., D376V and N434H); 307A, 380A and 434A (e.g., T307A, E380A and N434A); and 433K and 434F (e.g., H433K and N434F). All possible combinations of the foregoing Fc domain mutations and other mutations within the antibody variable domains disclosed herein, are contemplated within the scope of the present disclosure.

The present disclosure also includes anti-NPR1 antibodies comprising a chimeric heavy chain constant ($C_H$) region, wherein the chimeric $C_H$ region comprises segments derived from the $C_H$ regions of more than one immunoglobulin isotype. For example, the antibodies of the disclosure may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the disclosure comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., U.S. Patent Application Publication 2014/0243504, the disclosure of which is hereby incorporated by reference in its entirety).

Biological Characteristics of the Antibodies

In general, the antagonist antibodies of the present disclosure function by binding to NPR1 protein and blocking its signaling and/or activity. For example, the present disclosure includes antibodies and antigen-binding fragments of antibodies that bind to human NPR1 at 25° C. and at 37° C. with a dissociation constant ($K_D$) of less than 1.7 nM, as measured in a surface plasmon resonance assay, e.g., using the assay format as defined in Example 3 herein. In certain embodiments, the antibodies or antigen-binding fragments thereof bind human NPR1 with a Kp of less than about 1.27 nM, less than about 0.34 nM, less than about 0.08 nM, less than about 0.06 nM, as measured by surface plasmon resonance, e.g., using the assay format as defined in Example 3 herein, or a substantially similar assay.

The present disclosure also includes antibodies and antigen-binding fragments of antibodies that bind to monkey NPR1 at 25° C. and at 37° C. with a dissociation constant ($K_D$) of less than 1.99 nM, as measured in a surface plasmon resonance assay, e.g., using the assay format as defined in Example 3 herein. In certain embodiments, the antibodies or antigen-binding fragments thereof bind monkey NPR1 with a $K_D$ of less than about 1.23 nM, less than about 0.32 nM, less than about 0.1 nM, less than about 0.07 nM, as measured by surface plasmon resonance, e.g., using the assay format as defined in Example 3 herein, or a substantially similar assay.

The present disclosure also includes antibodies and antigen-binding fragments of antibodies that bind to human NPR1 in the presence of ANP at 25° C. and at 37° C. with a $K_D$ of less than 1.52 nM, as measured in a surface plasmon resonance assay, e.g., using the assay format as defined in Example 3 herein. In certain embodiments, the antibodies or antigen-binding fragments thereof bind human NPR1 in the presence of ANP at 25° C. and at 37° C. with a $K_D$ of less than about 1.1 nM, less than about 0.8 nM, less than about 0.6 nM, and less than about 0.5 nM, as measured in a surface plasmon resonance assay, e.g., using the assay format as defined in Example 3 herein, or a substantially similar assay.

The present disclosure also includes antibodies and antigen-binding fragments of antibodies that inhibit ligand-induced NPR1 activation (for example, induced by ANP or BNP), as measured by cGMP accumulation assay, e.g., using the assay format as defined in Example 6 herein. In certain embodiments, the antibodies or antigen-binding fragments thereof inhibit ligand-induced NPR1 activation by at least about 80%, at least about 90%, at least about 92%, at least about 99% and at least about 100%, as measured by cGMP accumulation assay, e.g., using the assay format as defined in Example 6 herein, or a substantially similar assay.

The present disclosure also includes antibodies and antigen-binding fragments of antibodies that bind to human NPR1 in the presence or absence of ANP or BNP with an $EC_{50}$ of less than 2.9 nM, as measured by electrochemiluminescence-based immunoassay, e.g., using the assay format as defined in Example 7 herein. In certain embodiments, the antibodies or antigen-binding fragments thereof bind human NPR1 in the presence or absence of ANP or BNP with an $EC_{50}$ of less than about 2.1 nM, less than about 1.2 nM, and less than about 0.6 nM, as measured by electrochemiluminescence-based immunoassay, e.g., using the assay format as defined in Example 7 herein, or a substantially similar assay.

The present disclosure also includes antibodies and antigen-binding fragments of antibodies that bind to monkey NPR1 in the presence or absence of ANP or BNP with an $EC_{50}$ of less than 4.2 nM, as measured by electrochemiluminescence-based immunoassay, e.g., using the assay format as defined in Example 7 herein. In certain embodiments, the antibodies or antigen-binding fragments thereof bind monkey NPR1 in the presence or absence of ANP or BNP with an $EC_{50}$ of less than about 2.9 nM, less than about 2.1 nM, and less than about 0.7 nM, as measured by electrochemiluminescence-based immunoassay, e.g., using the assay format as defined in Example 7 herein, or a substantially similar assay.

The present disclosure also includes antibodies and antigen-binding fragments of antibodies that increases the systemic blood pressures (including systolic, diastolic, mean arterial, and pulse pressures) when administered to normotensive and hypotensive mice, wherein the increase in systemic blood pressures lasts for up to about 28 days upon administration of a single dose, e.g., as described in Example 9 herein.

The present disclosure also includes antibodies and antigen-binding fragments of antibodies that increase the systemic blood pressures when administered to ANP overexpression-induced hypotensive mice, wherein the increase in systemic blood pressures lasts for up to about 28 days upon administration of a single dose, e.g., as described in Example 10 herein.

The present disclosure also includes antibodies and antigen-binding fragments thereof that increase systemic blood pressures in LPS-induced hypotensive mice, as described in Example 11 herein.

In one embodiment, the present disclosure provides an isolated recombinant antibody or antigen-binding fragment thereof that binds specifically to NPR1 protein in the presence or absence of ANP or BNP and reduces or blocks the signaling and/or activity of NPR1, wherein the antibody or fragment thereof exhibits one or more of the following characteristics: (a) is a fully human monoclonal antibody; (b) binds to human NPR1 at 25° C. and at 37° C. with a dissociation constant ($K_D$) of less than 1.7 nM, as measured in a surface plasmon resonance assay; (c) binds to monkey NPR1 at 25° C. and 37° C. with a $K_D$ of less than 1.99 nM, as measured in a surface plasmon resonance assay; (d) binds to human NPR1 in the presence of ANP at 25° C. and at 37° C. with a $K_D$ of less than 1.52 nM, as measured in a surface plasmon resonance assay; (e) inhibits ligand-induced NPR1 activation, as measured by cGMP accumulation assay; (f) binds to human NPR1 in the presence or absence of ANP or BNP with an $EC_{50}$ of less than 2.9 nM, as measured by electrochemiluminescence-based immunoassay; (g) binds to monkey NPR1 in the presence or absence of ANP or BNP with an $EC_{50}$ of less than 4.2 nM, as measured by electrochemiluminescence-based immunoassay; (h) increases the systemic blood pressures when administered to normotensive and hypotensive mice, wherein the increase in systemic blood pressures lasts for up to about 28 days upon administration of a single dose; (i) increases the systemic blood pressures when administered to ANP overexpression-induced hypotensive mice, wherein the increase in systemic blood pressures lasts for up to about 28 days upon administration of a single dose; (j) increases systemic blood pressures in LPS-induced hypotensive mice; and (k) comprises a HCVR comprising an amino acid sequence selected from the group consisting of HCVR sequences listed in Table 1 and a LCVR comprising an amino acid sequence selected from the group consisting of LCVR sequences listed in Table 1.

The antibodies of the present disclosure may possess one or more of the aforementioned biological characteristics, or any combinations thereof. Other biological characteristics of the antibodies of the present disclosure will be evident to a person of ordinary skill in the art from a review of the present disclosure including the working Examples herein.

Epitope Mapping and Related Technologies

The present disclosure includes antagonist anti-NPR1 antibodies that interact with one or more amino acids found within one or more regions of the NPR1 protein molecule. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within any of the aforementioned domains of the NPR1 protein molecule (e.g. a linear epitope in a domain). Alternatively, the epitope may consist of a plurality of non-contiguous amino acids (or amino acid sequences) located within either or both of the aforementioned domains of the protein molecule (e.g. a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, NY). Other methods include alanine scanning mutational analysis, peptide blot analysis (Reineke, (2004) *Methods Mol. Biol.* 248:443-63), peptide cleavage analysis crystallographic studies and NMR analysis. In addition, methods such as epitope excision, epitope extraction and chemical modification of antigens can be employed (Tomer, (2000) *Prot. Sci.* 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues that correspond to the specific amino acids with which the antibody interacts. See, e.g., Ehring, (1999) *Analytical Biochemistry* 267:252-259; Engen and Smith, (2001) *Anal. Chem.* 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the disclosure into groups of antibodies binding different epitopes.

In certain embodiments, the present disclosure includes antagonist anti-NPR1 antibodies and antigen-binding fragments thereof that interact with one or more epitopes found within the extracellular domain of NPR1. The epitope(s) may consist of one or more contiguous sequences of 3 or more (e.g., 3, 4, 5, 6, 7, 8, 9, 10, 11, 12, 13, 14, 15, 16, 17, 18, 19, 20 or more) amino acids located within the extracellular domain of NPR1. Alternatively, the epitope may consist of a plurality of non-contiguous amino acids (or amino acid sequences) located within NPR1.

The present disclosure includes antagonist anti-NPR1 antibodies that bind to the same epitope, or a portion of the epitope, as any of the specific exemplary antibodies listed in Table 1. Likewise, the present disclosure also includes antagonist anti-NPR1 antibodies that compete for binding to NPR1 protein or a fragment thereof with any of the specific exemplary antibodies listed in Table 1. For example, the present disclosure includes antagonist anti-NPR1 antibodies that cross-compete for binding to NPR1 protein with one or more antibodies listed in Table 1.

One can easily determine whether an antibody binds to the same epitope as, or competes for binding with, a reference anti-NPR1 antibody by using routine methods known in the art. For example, to determine if a test antibody binds to the same epitope as a reference anti-NPR1 antibody of the disclosure, the reference antibody is allowed to bind to a NPR1 protein or peptide under saturating conditions. Next, the ability of a test antibody to bind to the NPR1 protein molecule is assessed. If the test antibody is able to bind to NPR1 following saturation binding with the reference anti-NPR1 antibody, it can be concluded that the test antibody binds to a different epitope than the reference anti-NPR1 antibody. On the other hand, if the test antibody is not able to bind to the NPR1 protein following saturation binding with the reference anti-NPR1 antibody, then the test antibody may bind to the same epitope as the epitope bound by the reference anti-NPR1 antibody of the disclosure.

To determine if an antibody competes for binding with a reference anti-NPR1 antibody, the above-described binding methodology is performed in two orientations: In a first orientation, the reference antibody is allowed to bind to a NPR1 protein under saturating conditions followed by assessment of binding of the test antibody to the NPR1 molecule. In a second orientation, the test antibody is allowed to bind to a NPR1 molecule under saturating conditions followed by assessment of binding of the reference antibody to the NPR1 molecule. If, in both orientations, only the first (saturating) antibody is capable of binding to the NPR1 molecule, then it is concluded that the test antibody and the reference antibody compete for binding to NPR1. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans, et al., *Cancer Res.* 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

In certain embodiments, the present disclosure provides an isolated antibody or antigen-binding fragment thereof that binds specifically to natriuretic peptide receptor 1 (NPR1) protein and blocks NPR1.

Immunoconjugates

The disclosure encompasses a human antagonist anti-NPR1 monoclonal antibody conjugated to a therapeutic moiety ("immunoconjugate"), to treat a NPR1-associated disease or disorder (e.g., hypotension). As used herein, the term "immunoconjugate" refers to an antibody that is chemically or biologically linked to a radioactive agent, a cytokine, an interferon, a target or reporter moiety, an enzyme, a peptide or protein or a therapeutic agent. The antibody may be linked to the radioactive agent, cytokine, interferon, target or reporter moiety, enzyme, peptide or therapeutic agent at any location along the molecule so long as it is able to bind its target. Examples of immunoconjugates include antibody drug conjugates and antibody-toxin fusion proteins. In one embodiment, the agent may be a second different antibody to NPR1 protein. The type of therapeutic moiety that may be conjugated to the anti-NPR1 antibody and will take into account the condition to be treated and the desired therapeutic effect to be achieved. Examples of suitable agents for forming immunoconjugates are known in the art; see for example, WO 05/103081.

Multi-specific Antibodies

The antagonist antibodies of the present disclosure may be mono-specific, bi-specific, or multi-specific. Multi-specific antibodies may be specific for different epitopes of one target polypeptide or may contain antigen-binding domains specific for more than one target polypeptide. See, e.g., Tutt, et al., 1991, *J. Immunol.* 147:60-69; Kufer, et al., 2004, *Trends Biotechnol.* 22:238-244.

Any of the multi-specific antigen-binding molecules of the disclosure, or variants thereof, may be constructed using standard molecular biological techniques (e.g., recombinant DNA and protein expression technology), as will be known to a person of ordinary skill in the art.

In some embodiments, NPR1-specific antibodies are generated in a bi-specific format (a "bi-specific") in which variable regions binding to distinct domains of NPR1 protein are linked together to confer dual-domain specificity within a single binding molecule. Variable regions with specificity for individual domains, (e.g., segments of the N-terminal domain), or that can bind to different regions within one domain, are paired on a structural scaffold that allows each region to bind simultaneously to the separate epitopes, or to different regions within one domain. In one example for a bi-specific, heavy chain variable regions (VA) from a binder with specificity for one domain are recombined with light chain variable regions ($V_L$) from a series of binders with specificity for a second domain to identify non-cognate $V_L$ partners that can be paired with an original $V_H$ without disrupting the original specificity for that $V_H$. In this way, a single $V_L$ segment (e.g., $V_L1$) can be combined with two different $V_H$ domains (e.g., $V_H1$ and $V_H2$) to generate a bi-specific comprised of two binding "arms" ($V_H1$-$V_L1$ and $V_H2$-$V_L1$). Use of a single $V_L$ segment reduces the complexity of the system and thereby simplifies and increases efficiency in cloning, expression, and purification processes used to generate the bi-specific (See, for example, US2011/0195454 and US2010/0331527).

Alternatively, antibodies that bind more than one domains and a second target, such as, but not limited to, for example, a second different anti-NPR1 antibody, may be prepared in a bi-specific format using techniques described herein, or other techniques known to those skilled in the art. Antibody variable regions binding to distinct regions may be linked together with variable regions that bind to relevant sites on, for example, the extracellular domain of NPR1, to confer dual-antigen specificity within a single binding molecule. Appropriately designed bi-specifics of this nature serve a dual function. Variable regions with specificity for the extracellular domain are combined with a variable region with specificity for outside the extracellular domain and are paired on a structural scaffold that allows each variable region to bind to the separate antigens.

Other exemplary bispecific formats that can be used in the context of the present disclosure include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab2 bispecific formats (see, e.g., Klein, et al., 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane, et al., *J. Am. Chem. Soc.* [Epub: Dec. 4, 2012]).

Therapeutic Administration and Formulations

The disclosure provides therapeutic compositions comprising the antagonist anti-NPR1 antibodies or antigen-binding fragments thereof of the present disclosure. Therapeutic compositions in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFEC-TIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also, Powell, et al., "Compendium of excipients for parenteral formulations" *PDA* (1998) *J Pharm Sci Technol* 52:238-311.

The dose of antibody may vary depending upon the age and the size of a subject to be administered, target disease, conditions, route of administration, and the like. When an antibody of the present disclosure is used for treating a disease or disorder in an adult patient, or for preventing such a disease, it is advantageous to administer the antibody of the present disclosure normally at a single dose of about 0.1 to about 100 mg/kg body weight. In one embodiment, the antibody according to the disclosure is administered at a single dose of about 25 mg/kg body weight. Depending on the severity of the condition, the frequency and the duration of the treatment can be adjusted. In certain embodiments, the antibody or antigen-binding fragment thereof of the disclosure can be administered as an initial dose of at least about 0.1 mg to about 800 mg, about 1 to about 600 mg, about 5 to about 500 mg, about 10 to about 400 mg, or about 100 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the disclosure, e.g., encapsulation in liposomes, microparticles, microcapsules, recombinant cells capable of expressing the mutant viruses, receptor mediated endocytosis (see, e.g., Wu, et al., (1987) *J. Biol. Chem.* 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer, (1990) *Science* 249: 1527-1533).

The use of nanoparticles to deliver the antibodies of the present disclosure is also contemplated herein. Antibody-conjugated nanoparticles may be used both for therapeutic and diagnostic applications. Antibody-conjugated nanoparticles and methods of preparation and use are described in detail by Arruebo, M., et al., 2009 ("Antibody-conjugated nanoparticles for biomedical applications" in *J. Nanomat.* Volume 2009, Article ID 439389, 24 pages, doi: 10.1155/2009/439389), incorporated herein by reference. Nanoparticles may be developed and conjugated to antibodies contained in pharmaceutical compositions to target cells. Nanoparticles for drug delivery have also been described in, for example, U.S. Pat. No. 8,257,740, or U.S. Pat. No. 8,246,995, each incorporated herein in its entirety.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracranial, intraperitoneal and intramuscular injections, drip infusions, etc. These injectable preparations may be prepared by methods publicly known.

A pharmaceutical composition of the present disclosure can be delivered subcutaneously or intravenously with a standard needle and syringe. In addition, with respect to subcutaneous delivery, a pen delivery device readily has applications in delivering a pharmaceutical composition of the present disclosure. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the antibody contained is generally about 5 to about 500 mg per dosage form in a unit dose; especially in the form of injection, it is preferred that the antibody is contained in about 5 to about 300 mg and in about 10 to about 300 mg for the other dosage forms.

Therapeutic Uses of the Antibodies

The antagonist antibodies of the present disclosure are useful for the treatment, and/or prevention of a disease or disorder or condition associated with NPR1 and/or for ameliorating at least one symptom associated with such disease, disorder, or condition. In certain embodiments, an antibody or antigen-binding fragment thereof of the disclosure may be administered at a therapeutic dose to a patient with a disease or disorder or condition associated with NPR1.

The disorder or disease may include hypotension, and/or a disorder or disease associated with hypotension, and/or hypotension associated with a disease or disorder, for example, circulatory shock, septic shock, and neurodegenerative disease. Hypotension is a decrease in systemic blood pressure below accepted low values. Hypotension exists as a range, with no accepted standard hypotensive value, but pressures less than 90 mm Hg (systolic)/60 mm Hg (diastolic) are recognized as hypotensive. Symptoms of hypotension may include, without limitation, lightheadedness, dizziness, syncope, chest pain, shortness of breath, irregular heartbeat, elevated body temperature, headache, stiff neck, severe upper back pain, cough with sputum, diarrhea, vomiting, dysuria, acute allergic reactions, fatigue, and vision aberrations. Complications of untreated hypotension with poor cardiac output are severe and can ultimately lead to death. In impending shock or fulminant shock, untreated hypotension can lead to multi-organ failure (Sharma, et al., updated 2021, Hypotension, available from www.ncbi. nlm.nih.gov/books/NBK499961/). In one embodiment, an antagonistic anti-NPR1 antibody or antigen-binding fragment thereof according to the disclosure is used to treat a symptom or an indication of a type of hypotension. In another embodiment, an antagonistic anti-NPR1 antibody or antigen-binding fragment thereof according to the disclosure is used to increase the blood pressure of a subject having hypotension and/or having a disease or disorder associated with hypotension.

Septic shock is characterized by refractory hypotension, causing inadequate perfusion of tissues, and is associated with high mortality rates. The standard of care for sepsis coupled with hypotension is the administration of vasopressors, such as catecholamines or mimetics, vasopressin, or Ang II, to maintain arterial pressure and serum lactate levels in the absence of hypovolemia. However, the standard of care vasopressors have significant drawbacks, including requiring frequent titration, having a narrow therapeutic range, requiring central venous access and ICU care, and possibly even reducing capillary perfusion (causing tissue ischemia (for example, digital necrosis) at prolonged high doses). Thus, there remains a significant unmet need for addressing the (refractory) hypotension. In one embodiment, an antagonistic anti-NPR1 antibody or antigen-binding fragment thereof according to the disclosure is used to treat a symptom or an indication of septic shock, or to treat the refractory hypotension of septic shock. In another embodiment, the use of an antagonistic anti-NPR1 antibody or antigen-binding fragment thereof according to the disclosure to treat septic shock, or to treat the refractory hypotension of septic shock, allows for a reduced use of vasopressors. As a result, a reduced length of intensive care unit (ICU) stay is required.

Neurogenic orthostatic hypotension constitutes hypotension in the upright position (blood pressure drops when standing, leading to cerebral hypoperfusion) and is generally due to defects in autonomic reflexes associated with neurodegenerative disease. It complicates multiple diseases and is associated with significant morbidity, with symptom impact on daily activities rating as severe or very severe in almost 50% of patients. The two presently approved drug therapies are only modestly efficacious, both being short-acting and requiring three times daily (TID) dosing. In one embodiment, an antagonistic anti-NPR1 antibody or antigen-binding fragment thereof according to the disclosure is used to treat neurogenic orthostatic hypotension.

The disorder or disease may also include postural orthostatic tachycardia syndrome (POTS). This syndrome is marked by tachycardia plus symptoms in upright position, though without hypotension. In POTS, a heart rate increase from horizontal to standing (or as tested on a tilt table) of at least 30 beats per minute is registered in adults, measured during the first 10 minutes of standing. POTS typically afflicts young women and causes significant morbidity. The symptoms that occur upon standing include lightheadedness, tremor, palpitations, weakness, fatigue, blurry vision, occasional syncope, and the like. A significantly reduced quality of life is reported by over 80% of POTS patients. While fludrocortisone, midodrine, and beta-blockers are commonly used, they have not exhibited significant treatment efficacy; indeed, no specific drugs to treat POTS are currently FDA-approved. In one embodiment, an antagonistic anti-NPR1 antibody or antigen-binding fragment thereof according to the disclosure is used to treat POTS.

In certain embodiments, the antagonist antibodies of the present disclosure are useful for treating or preventing at least one symptom or indication of a disease or disorder selected from the group consisting of hypotension, circulatory shock, septic shock, neurogenic orthostatic hypotension, postural orthostatic tachycardia syndrome (POTS), heart failure, cardiogenic shock, obesity, renal failure, chronic kidney disease, macular edema, glaucoma, stroke, lung disorders, pulmonary fibrosis, inflammation, asthma, skeletal growth disorders, bone fractures, diabetes, hypoglycemia, and cancer.

It is also contemplated herein to use one or more antibodies of the present disclosure prophylactically to subjects at risk for suffering from a NPR1-associated disease or disorder.

In one embodiment of the disclosure, the present antibodies are used for the preparation of a pharmaceutical composition or medicament for treating patients suffering from a disease, disorder or condition disclosed herein. In another embodiment of the disclosure, the present antibodies are used as adjunct therapy with any other agent or any other therapy known to those skilled in the art useful for treating or ameliorating a disease, disorder or condition disclosed herein.

Combination Therapies

Combination therapies may include an antagonist antibody of the disclosure and any additional therapeutic agent that may be advantageously combined with an antibody of the disclosure, or with a biologically active fragment of an antibody of the disclosure. The antibodies of the present disclosure may be combined synergistically with one or more drugs or therapy used to treat a NPR1-associated disease or disorder, including hypotension. In some embodiments, the antibodies of the disclosure may be combined with a second therapeutic agent or therapy to ameliorate one or more symptoms of said disease or condition.

Depending upon the disease, disorder, or condition, the antibodies of the present disclosure may be used in combination with one or more additional therapeutic agents including, but not limited to, an angiogenesis inhibitor, a vasoconstrictor/vasopressor, an immunosuppressant, ascorbic acid, a calcineurin inhibitor, a corticosteroid, a VEGF inhibitor, a decongestant, an antidepressant, hormonal birth control, a stimulant (including cardiac stimulant), caffeine, extracorporeal membrane oxygenation, ventricular assist device, intra-aortic balloon pump, a lifestyle modification, a dietary supplement, an anti-microbial drug, insulin, and an anti-inflammatory drug.

As used herein, the term "in combination with" means that additional therapeutically active component(s) may be administered prior to, concurrent with, or after the administration of the antagonist anti-NPR1 antibody of the present disclosure. The term "in combination with" also includes sequential or concomitant administration of an anti-NPR1 antibody and a second therapeutic agent or therapy.

The additional therapeutically active component(s) may be administered to a subject prior to administration of an anti-NPR1 antibody of the present disclosure. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, or less than 30 minutes before administration of the second component. In other embodiments, the additional therapeutically active component(s) may be administered to a subject after administration of an anti-NPR1 antibody of the present disclosure. For example, a first component may be deemed to be administered "after" a second component if the first component is administered 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after or more after administration of the second component. In yet other embodiments, the additional therapeutically active component(s) may be administered to a subject concurrent with administration of an anti-NPR1 antibody of the present disclosure. "Concurrent" administration, for purposes of the present disclosure, includes, e.g., administration of an anti-NPR1 antibody and an additional therapeutically active component to a subject in a single dosage form, or in separate dosage forms administered to the subject within about 30 minutes or less of each other. If administered in separate dosage forms, each dosage form may be administered via the same route (e.g., both the anti-NPR1 antibody and the additional therapeutically active component may be administered intravenously, etc.); alternatively, each dosage form may be administered via a different route (e.g., the anti-NPR1 antibody may be administered intravenously, and the additional therapeutically active component may be administered orally). In any event, administering the components in a single dosage from, in separate dosage forms by the same route, or in separate dosage forms by different routes are all considered "concurrent administration," for purposes of the present disclosure. For purposes of the present disclosure, administration of an anti-NPR1 antibody "prior to", "concurrent with," or "after" (as those terms are defined herein above) administration of an additional therapeutically active component is considered administration of an anti-NPR1 antibody "in combination with" an additional therapeutically active component.

The present disclosure includes pharmaceutical compositions in which an anti-NPR1 antibody of the present disclosure is co-formulated with one or more of the additional therapeutically active component(s) as described elsewhere herein.

Diagnostic Uses of the Antibodies

The antagonist antibodies of the present disclosure may be used to detect and/or measure NPR1 in a sample, e.g., for diagnostic purposes. Some embodiments contemplate the use of one or more antibodies of the present disclosure in assays to detect a NPR1-associated-disease or disorder. Exemplary diagnostic assays for NPR1 may comprise, e.g., contacting a sample, obtained from a patient, with an anti-NPR1 antibody of the disclosure, wherein the anti-NPR1 antibody is labeled with a detectable label or reporter molecule or used as a capture ligand to selectively isolate NPR1 from patient samples. Alternatively, an unlabeled anti-NPR1 antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure NPR1 in a sample include enzyme-linked immunosorbent assay (ELISA), radioimmunoassay (RIA), and fluorescence-activated cell sorting (FACS).

Samples that can be used in NPR1 diagnostic assays according to the present disclosure include any tissue or fluid sample obtainable from a patient, which contains detectable quantities of either NPR1 protein, or fragments thereof, under normal or pathological conditions. Generally, levels of NPR1 protein in a particular sample obtained from a healthy patient (e.g., a patient not afflicted with a disease associated with NPR1) will be measured to initially establish a baseline, or standard, level of NPR1. This baseline level of NPR1 can then be compared against the levels of NPR1 measured in samples obtained from individuals suspected of having a NPR1-associated condition, or symptoms associated with such condition.

The antibodies specific for NPR1 protein may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

EXAMPLES

The following examples are put forth so as to provide those of ordinary skill in the art with a complete disclosure and description of how to make and use the methods and compositions of the disclosure, and are not intended to limit the scope of what the inventors regard as their disclosure. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Generation of Human Antibodies to Natriuretic Peptide Receptor 1 (NPR1)

Human antibodies to NPR1 protein were generated in a VELOCIMMUNE® mouse comprising DNA encoding human immunoglobulin heavy and kappa light chain variable regions. The mice were immunized with human NPR1 and mouse ANP DNA by hydrodynamic DNA delivery and boosted by extracellular domain of human NPR1 protein complexed to mouse ANP.

The antibody immune response was monitored by a NPR1-specific immunoassay. When a desired immune response was achieved, splenocytes were harvested and fused with mouse myeloma cells to preserve their viability and form hybridoma cell lines. The hybridoma cell lines were screened and selected to identify cell lines that produce NPR1-specific antibodies. The cell lines were used to obtain several anti-NPR1 chimeric antibodies (i.e., antibodies possessing human variable domains and mouse constant domains).

Anti-NPR1 antibodies were also isolated directly from antigen-positive mouse B cells without fusion to myeloma cells, as described in U.S. Pat. No. 7,582,298, herein specifically incorporated by reference in its entirety. Using this method, several fully human anti-NPR1 antibodies (i.e., antibodies possessing human variable domains and human constant domains) were obtained.

Exemplary antibodies generated as disclosed above were designated as mAb38067, mAb38072, mAb38090, and mAb22034.

The biological properties of the exemplary antibodies generated in accordance with the methods of this Example are described in detail in the Examples set forth below.

Example 2: Heavy and Light Chain Variable Region Amino Acid and Nucleotide Sequences Table 1 sets forth the amino acid sequence identifiers of the heavy and light chain variable regions and CDRs of selected anti-NPR1 antibodies of the disclosure.

Antibodies referred to herein typically have fully human variable regions but may have human or mouse constant regions. As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG1 or a human IgG4, etc.), but in any event, the variable domains (including the CDRs)—which are indicated by the numerical identifiers shown in Table 1-will remain the same, and the binding properties to antigen are expected to be identical or substantially similar regardless of the nature of the Fc domain.

In certain embodiments, selected antibodies with a mouse IgG1 Fc are converted to antibodies with human IgG4 Fc. In one embodiment, the IgG4 Fc domain comprises 2 or more amino acid changes as disclosed in US20100331527. In one embodiment, the human IgG4 Fc comprises a serine to proline mutation in the hinge region (S108P) to promote dimer stabilization. Unless indicated otherwise, all antibodies used in the following examples comprise a human IgG4 isotype.

Exemplary antibodies mAb38067, mAb38072, mAb38090, and mAb22034 comprising a human IgG4 Fc comprising a serine to proline mutation in the hinge region (S108P) were designated as REGN7541, REGN7544, REGN7548, and H4H22034 respectively. Table 3 sets forth the nucleic acid and amino acid sequence identifiers of full-length heavy chain and light chain sequences of these antibodies.

TABLE 1

| Amino Acid Sequence Identifiers | | | | | | | |
|---|---|---|---|---|---|---|---|
| Antibody | SEQ ID NOs: | | | | | | |
| Designation | HCVR | HCDR1 | HCDR2 | HCDR3 | LCVR | LCDR1 | LCDR2 | LCDR3 |
| mAb38067 | 2 | 4 | 6 | 8 | 10 | 12 | AAS | 16 |
| mAb38072 | 22 | 24 | 26 | 28 | 30 | 12 | AAS | 32 |
| mAb38090 | 38 | 40 | 42 | 44 | 46 | 48 | AAS | 16 |
| mAb22034 | 55 | 57 | 59 | 61 | 63 | 65 | GAS | 69 |

The corresponding nucleic acid sequence identifiers are set forth in Table 2.

TABLE 2

| Nucleic Acid Sequence Identifiers | | | | | | | |
|---|---|---|---|---|---|---|---|
| Antibody | SEQ ID NOs: | | | | | | |
| Designation | HCVR | HCDR1 | HCDR2 | HCDR3 | LCVR | LCDR1 | LCDR2 | LCDR3 |
| mAb38067 | 1 | 3 | 5 | 7 | 9 | 11 | gctgcatcc | 15 |
| mAb38072 | 21 | 23 | 25 | 27 | 29 | 11 | gctgcatcc | 31 |
| mAb38090 | 37 | 39 | 41 | 43 | 45 | 47 | gctgcatcc | 49 |
| mAb22034 | 54 | 56 | 58 | 60 | 62 | 64 | ggcgcatcc | 68 |

TABLE 3

Full-length Heavy Chain and Light Chain Sequence identifiers

| Antibody | Antibody | SEQ ID NOs: | | | |
|---|---|---|---|---|---|
| | | HC | | LC | |
| ID | Name | DNA | PEP | DNA | PEP |
| mAb38067 | REGN7541 | 17 | 18 | 19 | 20 |
| mAb38072 | REGN7544 | 33 | 34 | 35 | 36 |
| mAb38090 | REGN7548 | 50 | 51 | 52 | 53 |
| mAb22034 | H4H22034 | 70 | 71 | 72 | 73 |

Control Constructs used in the Following Examples

The following control construct (anti-NPR1 antibody) was included in the experiments disclosed herein, for comparative purposes: "Comparator 1," a monoclonal antibody against human NPR1 having $V_H/V_L$ sequences of antibody "mAb5591" according to US Patent No. 20120114659 (Morphosys).

Example 3: Biacore Binding Kinetics of Anti-NPR1 Monoclonal Antibodies Binding to Various NPR1 Reagents Measured at 25° C. And 37° C.

Experimental Procedure

The equilibrium dissociation constant ($K_D$) for different NPR1 reagents binding to purified anti-NPR1 monoclonal antibodies (mAbs) were determined using a real-time surface plasmon resonance (SPR) based Biacore 8k biosensor. All binding studies were performed in 10 mM HEPES, 150 mM NaCl, 3 mM EDTA, and 0.05% v/v Surfactant P20, pH 7.4 (HBS-EP) running buffer at 25° C. and 37° C. The Biacore CM5 sensor chip surface was first derivatized by amine coupling with anti-human Fc specific antibody to capture anti-NPR1 mAbs. Binding studies were performed on human NPR1 extracellular domain expressed with a C-terminal myc-myc-hexahistidine (hNPR1-MMH; SEQ ID NO:74), monkey NPR1 extracellular domain expressed with a C-terminal myc-myc-hexahistidine (mfNPR1-MMH; SEQ ID NO:75), mouse NPR1 extracellular domain expressed with a C-terminal myc-myc-hexahistidine (mNPR1-MMH; SEQ ID NO:76), dog NPR1 extracellular domain expressed with a C-terminal myc-myc-hexahistidine (dog_NPR1-MMH; SEQ ID NO:77), pig NPR1 extracellular domain expressed with a C-terminal myc-myc-hexahistidine (pig_NPR1-MMH; SEQ ID NO: 78), and hNPR1-MMH+ 10× hANP.

Different concentrations (40 nM-0.625 nM, 4-fold serial dilutions) of hNPR1-MMH, mfNPR1-MMH, hNPR1-MMH in the presence of 10-fold concentration of hANP, or a fixed concentration (40 nM) of mNPR1-MMH, dog_NPR1-MMH, pig_NPR1-MMH were prepared in HBS-EP running buffer, and then injected for 150 sec at a flow rate of 30 μL/min, while the dissociation of mAb bound different NPR1 reagents was monitored for 30 minutes in HBS-EP running buffer. At the end of each cycle, the anti-NPR1 mAb capture surface was regenerated using a 12 sec injection of 10 mM phosphoric acid. The association rate (ka) and dissociation rate (kd) were determined by fitting the real-time binding sensorgrams to a 1:1 binding model with mass transport limitation using Biacore insight evaluation software. Binding dissociation equilibrium constant ($K_D$) and dissociative half-life (t½) were calculated from the kinetic rates as:

$$K_D(M) = \frac{kd}{ka}, \text{ and } t1/2(\text{min}) = \frac{\ln(2)}{60*kd}$$

Binding kinetics parameters for different NPR1 reagents binding to different anti-NPR1 mAbs of the disclosure at 25° C. and 37° C. are shown in Tables 4 through 15.

Results

At 25° C., anti-NPR1 monoclonal antibodies bound to hNPR1-MMH with Ko values ranging from 47.4 pM to 1.27 nM, as shown in Table 4.

TABLE 4

Binding kinetics parameters of different anti-NPR1 mAbs to hNPR1-MMH at 25° C.

| mAb Captured | mAb Capture Level (RU) | 40 nM Ag Bound (RU) | $k_a$ (1/Ms) | $k_d$ (1/s) | $K_D$ (M) | t½ (min) |
|---|---|---|---|---|---|---|
| H4H22034N | 59 ± 0.4 | 34 | 3.26E+05 | 4.15E−04 | 1.27E−09 | 28 |
| REGN7541 | 59 ± 0.2 | 26 | 2.02E+05 | 6.80E−05 | 3.36E−10 | 170 |
| REGN7544 | 60 ± 0.4 | 29 | 2.81E+05 | 1.33E−05 | 4.74E−11 | 868 |
| REGN7548 | 59 ± 0.3 | 38 | 4.22E+05 | 3.40E−05 | 8.06E−11 | 340 |
| Isotype control | 59 ± 0.1 | 0 | NB* | NB | NB | NB |

*NB = no binding detected

At 37° C., anti-NPR1 monoclonal antibodies bound to hNPR1-MMH with a Ko values ranging from 57.4 pM to 1.7 nM, as shown in Table 5.

TABLE 5

Binding kinetics parameters of different anti-NPR1 mAbs to hNPR1-MMH at 37° C.

| mAb Captured | mAb Capture Level (RU) | 40 nM Ag Bound (RU) | $k_a$ (1/Ms) | $k_d$ (1/s) | $K_D$ (M) | t½ (min) |
|---|---|---|---|---|---|---|
| H4H22034N | 71 ± 0.3 | 44 | 6.26E+05 | 1.06E−03 | 1.70E−09 | 11 |
| REGN7541 | 69 ± 0.4 | 41 | 7.47E+05 | 1.34E−04 | 1.79E−10 | 86 |
| REGN7544 | 72 ± 0.2 | 43 | 5.69E+05 | 3.27E−05 | 5.74E−11 | 353 |

TABLE 5-continued

| | Binding kinetics parameters of different anti-NPR1 mAbs to hNPR1-MMH at 37° C. | | | | | |
|---|---|---|---|---|---|---|
| mAb Captured | mAb Capture Level (RU) | 40 nM Ag Bound (RU) | $k_a$ (1/Ms) | $k_d$ (1/s) | $K_D$ (M) | $t^{1/2}$ (min) |
| REGN7548 | 71 ± 0.3 | 50 | 7.77E+05 | 6.60E−05 | 8.49E−11 | 175 |
| Isotype control | 73 ± 0.1 | 0 | NB* | NB | NB | NB |

*NB = no binding detected

At 25° C., anti-NPR1 monoclonal antibodies bound to mfNPR1-MMH with Ko values ranging from 69 pM to 1.23 nM, as shown in Table 6.

TABLE 6

| | Binding kinetics parameters of different anti-NPR1 mAbs to mfNPR1-MMH at 25° C. | | | | | |
|---|---|---|---|---|---|---|
| mAb Captured | mAb Capture Level (RU) | 40 nM Ag Bound (RU) | $k_a$ (1/Ms) | $k_d$ (1/s) | $K_D$ (M) | $t^{1/2}$ (min) |
| H4H22034N | 59 ± 0.4 | 33 | 3.18E+05 | 3.92E−04 | 1.23E−09 | 29 |
| REGN7541 | 59 ± 0.2 | 26 | 2.11E+05 | 6.71E−05 | 3.18E−10 | 172 |
| REGN7544 | 60 ± 0.1 | 29 | 2.79E+05 | 2.02E−05 | 7.25E−11 | 571 |
| REGN7548 | 59 ± 0.2 | 38 | 4.19E+05 | 2.89E−05 | 6.90E−11 | 399 |
| Isotype control | 59 ± 0.1 | 1 | NB* | NB | NB | NB |

*NB = no binding detected

At 37° C., anti-NPR1 monoclonal antibodies bound to mfNPR1-MMH with a Ko values ranging from 53.6 pM to 1.99 nM, as shown in Table 7.

TABLE 7

| | Binding kinetics parameters of different anti-NPR1 mAbs to mfNPR1-MMH at 37° C. | | | | | |
|---|---|---|---|---|---|---|
| mAb Captured | mAb Capture Level (RU) | 40 nM Ag Bound (RU) | $k_a$ (1/Ms) | $k_d$ (1/s) | $K_D$ (M) | $t^{1/2}$ (min) |
| H4H22034N | 71 ± 0.3 | 37 | 5.04E+05 | 1.00E−03 | 1.99E−09 | 12 |
| REGN7541 | 69 ± 0.4 | 36 | 6.63E+05 | 1.04E−04 | 1.57E−10 | 111 |
| REGN7544 | 72 ± 0.1 | 36 | 5.48E+05 | 2.94E−05 | 5.36E−11 | 393 |
| REGN7548 | 71 ± 0.2 | 39 | 6.62E+05 | 6.49E−05 | 9.81E−11 | 178 |
| Isotype control | 72 ± 0.1 | 0 | NB* | NB | NB | NB |

*NB = no binding detected

45

At 25° C., anti-NPR1 monoclonal antibodies bound to hNPR1-MMH in the presence of 10-fold concentration of hANP with Ko values ranging from 78.8 pM to 500 pM, as shown in Table 8.

TABLE 8

| | Binding kinetics parameters of different anti-NPR1 mAbs to hNPR1-MMH in the presence of 10-fold concentration of hANP at 25° C. | | | | | |
|---|---|---|---|---|---|---|
| mAb Captured | mAb Capture Level (RU) | 40 nM Ag Bound (RU) | $k_a$ (1/Ms) | $k_d$ (1/s) | $K_D$ (M) | $t^{1/2}$ (min) |
| H4H22034N | 60 ± 0.2 | 35 | 3.46E+05 | 1.73E−04 | 5.00E−10 | 67 |
| REGN7541 | 60 ± 0.2 | 23 | 2.19E+05 | 6.07E−05 | 2.77E−10 | 190 |
| REGN7544 | 59 ± 0 | 26 | 2.61E+05 | 4.83E−05 | 1.85E−10 | 239 |
| REGN7548 | 61 ± 0 | 39 | 5.52E+05 | 4.35E−05 | 7.88E−11 | 266 |
| Isotype control | 57 ± 0.2 | 0 | NB* | NB | NB | NB |

*NB = no binding detected

At 37° C., anti-NPR1 monoclonal antibodies bound to hNPR1-MMH in the presence of 10-fold concentration of hANP with Ko values ranging from 642 pM to 1.52 nM, as shown in Table 9.

TABLE 9

| mAb Captured | mAb Capture Level (RU) | 40 nM Ag Bound (RU) | $k_a$ (1/Ms) | $k_d$ (1/s) | $K_D$ (M) | $t\frac{1}{2}$ (min) |
|---|---|---|---|---|---|---|
| H4H22034N | 75 ± 0.2 | 42 | 4.71E+05 | 7.17E−04 | 1.52E−09 | 16 |
| REGN7541 | 72 ± 0.2 | 32 | 3.49E+05 | 3.78E−04 | 1.08E−09 | 31 |
| REGN7544 | 69 ± 0.2 | 34 | 4.26E+05 | 3.51E−04 | 8.25E−10 | 33 |
| REGN7548 | 75 ± 0.1 | 42 | 5.93E+05 | 3.80E−04 | 6.42E−10 | 30 |
| Isotype control | 69 ± 0.1 | 0 | NB* | NB | NB | NB |

*Binding kinetics parameters of different anti-NPR1 mAbs to hNPR1-MMH in the presence of 10-fold concentration of hANP at 37° C.*

*NB = no binding detected

At 25° C., only two anti-NPR1 monoclonal antibodies bound to pig_NPR1-MMH with Ko values ranging from 35.8 nM to 122 nM as shown in Table 10.

TABLE 10

| mAb Captured | mAb Capture Level (RU) | 40 nM Ag Bound (RU) | $k_a$ (1/Ms) | $k_d$ (1/s) | $K_D$ (M) | $t\frac{1}{2}$ (min) |
|---|---|---|---|---|---|---|
| H4H22034N | 60 ± 0.1 | 0 | NB | NB | NB | NB |
| REGN7541 | 60 ± 0 | 0 | NB | NB | NB | NB |
| REGN7544 | 59 ± 0.1 | 2 | 5.58E+04 | 6.79E−03 | 1.22E−07 | 1.7 |
| REGN7548 | 61 ± 0.1 | 11 | 1.19E+05 | 4.27E−03 | 3.58E−08 | 2.7 |
| Isotype control | 57 ± 0 | 0 | NB* | NB | NB | NB |

*Binding kinetics parameters of different anti-NPR1 mAbs to pig_NPR1-MMH at 25° C.*

*NB = no binding detected

At 37° C., only two anti-NPR1 monoclonal antibodies bound to pig_NPR1-MMH with Ko values ranging from 42.1 nM to 98.1 nM as shown in Table 11.

TABLE 11

| mAb Captured | mAb Capture Level (RU) | 40 nM Ag Bound (RU) | $k_a$ (1/Ms) | $k_d$ (1/s) | $K_D$ (M) | $t\frac{1}{2}$ (min) |
|---|---|---|---|---|---|---|
| H4H22034N | 75 ± 0 | 0 | NB | NB | NB | NB |
| REGN7541 | 73 ± 0 | 0 | NB | NB | NB | NB |
| REGN7544 | 69 ± 0.3 | 5 | 9.65E+04 | 9.47E−03 | 9.81E−08 | 1.2 |
| REGN7548 | 75 ± 0.1 | 14 | 2.20E+05 | 9.27E−03 | 4.21E−08 | 1.2 |
| Isotype control | 69 ± 0.1 | 0 | NB* | NB | NB | NB |

*Binding kinetics parameters of different anti-NPR1 mAbs to pig_NPR1-MMH at 37° C.*

*NB = no binding detected

At 25° C. or at 37° C., none of the anti-NPR1 monoclonal antibodies bound to mNPR1-MMH as shown in Table 12 and Table 13, respectively.

TABLE 12

| mAb Captured | mAb Capture Level (RU) | 40 nM Ag Bound (RU) | $k_a$ (1/Ms) | $k_d$ (1/s) | $K_D$ (M) | $t\frac{1}{2}$ (min) |
|---|---|---|---|---|---|---|
| H4H22034N | 60 | 0 | NB | NB | NB | NB |
| REGN7541 | 60 | 0 | NB | NB | NB | NB |
| REGN7544 | 59 | 0 | NB | NB | NB | NB |

*Binding kinetics parameters of different anti-NPR1 mAbs to mNPR1-MMH at 25° C.*

TABLE 12-continued

| mAb Captured | mAb Capture Level (RU) | 40 nM Ag Bound (RU) | $k_a$ (1/Ms) | $k_d$ (1/s) | $K_D$ (M) | $t^{1/2}$ (min) |
|---|---|---|---|---|---|---|
| | | Binding kinetics parameters of different anti-NPR1 mAbs to mNPR1-MMH at 25° C. | | | | |
| REGN7548 | 61 | 0 | NB | NB | NB | NB |
| Isotype control | 57 | 0 | NB* | NB | NB | NB |

*NB = no binding detected

TABLE 13

| mAb Captured | mAb Capture Level (RU) | 40 nM Ag Bound (RU) | $k_a$ (1/Ms) | $k_d$ (1/s) | $K_D$ (M) | $t^{1/2}$ (min) |
|---|---|---|---|---|---|---|
| | | Binding kinetics parameters of different anti-NPR1 mAbs to mNPR1-MMH at 37° C. | | | | |
| H4H22034N | 75 | 0 | NB | NB | NB | NB |
| REGN7541 | 73 | 0 | NB | NB | NB | NB |
| REGN7544 | 69 | 0 | NB | NB | NB | NB |
| REGN7548 | 75 | 0 | NB | NB | NB | NB |
| Isotype control | 69 | 0 | NB* | NB | NB | NB |

*NB = no binding detected

At 25° C. or at 37° C., none of the anti-NPR1 monoclonal antibodies bound to dog_NPR1-MMH as shown in Table 14 and Table 15, respectively.

TABLE 14

| mAb Captured | mAb Capture Level (RU) | 40 nM Ag Bound (RU) | $k_a$ (1/Ms) | $k_d$ (1/s) | $K_D$ (M) | $t^{1/2}$ (min) |
|---|---|---|---|---|---|---|
| | | Binding kinetics parameters of different anti-NPR1 mAbs to dog_NPR1-MMH at 25° C. | | | | |
| H4H22034N | 60 ± 0 | 0 | NB | NB | NB | NB |
| REGN7541 | 60 ± 0.1 | 0 | NB | NB | NB | NB |
| REGN7544 | 59 ± 0.2 | 0 | NB | NB | NB | NB |
| REGN7548 | 61 ± 0 | 0 | NB | NB | NB | NB |
| Isotype control | 57 ± 0 | 0 | NB* | NB | NB | NB |

*NB = no binding detected

TABLE 15

| mAb Captured | mAb Capture Level (RU) | 40 nM Ag Bound (RU) | $k_a$ (1/Ms) | $k_d$ (1/s) | $K_D$ (M) | $t^{1/2}$ (min) |
|---|---|---|---|---|---|---|
| | | Binding kinetics parameters of different anti-NPR1 mAbs to dog_NPR1-MMH at 37° C. | | | | |
| H4H22034N | 75 ± 0 | 0 | NB | NB | NB | NB |
| REGN7541 | 73 ± 0.3 | 0 | NB | NB | NB | NB |
| REGN7544 | 69 ± 0.2 | 0 | NB | NB | NB | NB |
| REGN7548 | 75 ± 0 | 0 | NB | NB | NB | NB |
| Isotype control | 69 ± 0.1 | 0 | NB* | NB | NB | NB |

*NB = no binding detected

Example 4: PH Sensitivity of Anti-NPR1 Monoclonal Antibodies Binding to NPR1 Reagents Measured at 37° C.

Experimental Procedure

The dissociation rate constants ($k_d$) for different anti-NPR1 monoclonal antibodies (mAbs) in pH7.4, and pH6.0 buffers were determined using a real-time surface plasmon resonance (SPR) based Biacore 4000 biosensor. All binding studies were performed at 37° C. using two running buffers, (i) PBS, 0.05% v/v Surfactant Tween-20, pH7.4 (PBS-T-pH7.4), and (ii) PBS, 0.05% v/v Surfactant Tween-20, pH6.0 (PBS-T-pH6.0). The Biacore CM5 sensor chip surface was first derivatized by amine coupling with anti-human Fc specific antibody to capture anti-NPR1 mAbs. Different concentrations of human NPR1 extracellular domain expressed with a C-terminal myc-myc-hexahistidine (hNPR1-MMH; SEQ ID NO:74) or monkey NPR1 extracellular domain expressed with a C-terminal myc-myc-hexahistidine (mfNPR1-MMH; SEQ ID NO:75) (30 nM and 10 nM) were prepared in PBS-T-pH7.4 buffer were injected at a flow rate of 30 pL/min for 4 minutes followed by the dissociation of bound NPR1 reagents in PBS-T-pH7.4 or PBS-T-pH6.0 running buffers for 5 minutes.

The dissociation rate constants (ka) in two pH running buffers were determined by fitting the real-time binding sensorgrams to a 1:1 binding model using Scrubber 2.0c curve-fitting software. The dissociative half-life (t½) was calculated from the ka values as:

$$t1/2(\text{min}) = \frac{\ln(2)}{60 * kd}$$

Results

The ka and t½ values for different anti-NPR1 mAbs binding to hNPR1-MMH or mfNPR1-MMH in PBS-T, pH7.4 followed by dissociation in PBS-T-pH7.4, or PBS-T-pH6.0 of the disclosure at 37° C. are shown in Table 16 through Table 19.

TABLE 16

Binding of different anti-NPR1 monoclonal antibodies (mAbs) to hNPR1-MMH in PBS-T-pH 7.4 buffer and the dissociation in PBS-T-pH 7.4 buffer at 37° C.

| mAb Captured | mAb Capture Level (RU) | 30 nM Ag Bound (RU) | $k_d$ (1/s) | t½ (min) |
|---|---|---|---|---|
| H4H22034N | 310 ± 1.5 | 150 | 7.67E−04 | 15 |
| REGN7541 | 326 ± 0.4 | 170 | 7.34E−05 | 157 |
| REGN7544 | 359 ± 1.1 | 192 | 4.24E−05 | 273 |
| REGN7548 | 356 ± 1.4 | 215 | 6.58E−05 | 176 |
| Isotype control | 340 ± 1.4 | 2 | NB* | NB |

*NB = no binding detected

TABLE 17

Binding of different anti-NPR1 monoclonal antibodies (mAbs) to hNPR1-MMH in PBS-T-pH 7.4 buffer and the dissociation in PBS-T-pH 6.0 buffer at 37° C.

| mAb Captured | mAb Capture Level (RU) | 30 nM Ag Bound (RU) | $k_d$ (1/s) | t½ (min) |
|---|---|---|---|---|
| H4H22034N | 349 ± 0.6 | 172 | 1.38E−04 | 83 |
| REGN7541 | 369 ± 0.5 | 193 | 5.31E−05 | 217 |
| REGN7544 | 368 ± 1.1 | 193 | 1.58E−05 | 731 |
| REGN7548 | 366 ± 1.3 | 219 | 1.65E−05 | 702 |
| Isotype control | 344 ± 0.9 | 2 | NB* | NB |

*NB = no binding detected

TABLE 18

Binding of different anti-NPR1 monoclonal antibodies (mAbs) to mfNPR1-MMH in PBS-T-pH 7.4 buffer and the dissociation in PBS-T-pH 7.4 buffer at 37° C.

| mAb Captured | mAb Capture Level (RU) | 30 nM Ag Bound (RU) | kd (1/s) | t½ (min) |
|---|---|---|---|---|
| H4H22034N | 308 ± 0.2 | 139 | 7.81E−04 | 15 |
| REGN7541 | 322 ± 0.5 | 158 | 9.48E−05 | 122 |
| REGN7544 | 356 ± 1.2 | 178 | 3.55E−05 | 325 |
| REGN7548 | 354 ± 0.8 | 203 | 6.22E−05 | 186 |
| Isotype control | 340 ± 2.2 | 1 | NB* | NB |

*NB = no binding detected

TABLE 19

Binding of different anti-NPR1 monoclonal antibodies (mAbs) to mfNPR1-MMH in PBS-T-pH 7.4 buffer and the dissociation in PBS-T-pH 6.0 buffer at 37° C.

| mAb Captured | mAb Capture Level (RU) | 30 nM Ag Bound (RU) | $k_d$ (1/s) | t½ (min) |
|---|---|---|---|---|
| H4H22034N | 336 ± 8.2 | 157 | 1.54E−04 | 75 |
| REGN7541 | 367 ± 0.5 | 179 | 6.94E−05 | 166 |
| REGN7544 | 363 ± 1.9 | 181 | 1.50E−05 | 768 |
| REGN7548 | 363 ± 0.8 | 207 | 2.67E−05 | 433 |
| Isotype control | 336 ± 4.4 | 2 | NB* | NB |

*NB = no binding detected

Example 5: Octet cross-competition between different anti-NPR1 monoclonal antibodies Experimental Procedure Binding competition between different anti-NPR1 monoclonal antibodies (mAbs) was determined using a real time, label-free bio-layer interferometry (BLI) assay on the Octet HTX biosensor platform (Pall ForteBio Corp.). The entire experiment was performed at 25° C. in 10 mM HEPES, 150 mM NaCl, 3 mM EDTA, 1 mg/mL BSA, 0.02% NaN3, 0.05% v/v Surfactant Tween-20, pH7.4 (HBS-EBT) buffer with the plate shaking at a speed of 1000 rpm. To assess whether two antibodies are able to compete with one another for binding to their respective epitopes on recombinant human NPR1 extracellular domain expressed with a C-terminal myc-myc-hexahistidine (hNPR1-MMH; SEQ ID NO:74), around 0.64 nm of hNPR1-MMH was first captured onto anti-Penta-His antibody coated Octet biosensor tips (Fortebio Inc, #18-5122) by submerging the biosensor tips in wells containing 40-50 µg/mL solution of hNPR1-MMH for 60 seconds.

The antigen captured biosensor tips were then saturated with a first anti-NPR1 monoclonal antibody (subsequently referred to as mAb-1) by dipping into wells containing 50 µg/mL solution of mAb-1 for 4 minutes. The biosensor tips were then subsequently dipped into wells containing 50 g/mL solution of a second anti-NPR1 monoclonal antibody (subsequently referred to as mAb-2) for 3 minutes. The biosensor tips were washed in HBS-EBT buffer in between every step of the experiment. The real-time binding response was monitored during the entire course of the experiment and the binding response at the end of every step was recorded.

Results

The response of mAb-2 binding to hNPR1-MMH pre-complexed with mAb-1 was compared to the binding response when the order was reversed (mAb-2 first antibody bound, mAb1 second antibody bound) and competitive/non-competitive behavior of different anti-NPR1 monoclonal antibodies was determined as summarized in Table 20.

TABLE 20

Cross-competition between different anti-NPR1 monoclonal antibodies for binding to hNPR1-MMH

| mAb-1 | mAb-2 competing with mAb-1 |
|---|---|
| H4H22034N | H4H22034N |
| | REGN7541 |
| | REGN7544 |
| | REGN7548 |
| REGN7541 | H4H22034N |
| | REGN7541 |
| | REGN7544 |
| | REGN7548 |
| REGN7544 | H4H22034N |
| | REGN7541 |
| | REGN7544 |
| | REGN7548 |
| REGN7548 | H4H22034N |
| | REGN7541 |
| | REGN7544 |
| | REGN7548 |

Example 6: Assessment of NPR1 Antagonism of Antagonistic Anti-NPR1 Antibodies

Experimental Procedure

In order to assess the regulation of human natriuretic peptide receptor 1 (hNPR1), a HEK293 cell line stably expressing hNPR1 (amino acids M1 to G1061 of accession #NP_000897.3) with C-term myc and FLAG tags was generated and sorted for high hNPR1 expressing cells. The resulting cell line was named HEK293/hNPR1.MycDDK HS, abbreviated as HEK293/hNPR1, and was maintained in DMEM containing 10% FBS, NEAA, pen/strep/glutamine, and 500 μg/mL G418 sulfate. Binding of ligand to NPR1 activates the receptor's guanylate cyclase domain, which catalyzes the production of cGMP from GTP (Zois, et al., 2014 Natriuretic peptides in cardiometabolic regulation and disease. Nature Publishing Group, 11 (7), 403-412). A homogeneous time resolved fluorescence (HTRF) assay that measures cGMP levels was used to evaluate NPR1 activity.

Analysis of NPR1 Antagonism

To assess NPR1 antagonism, HEK293/hNPR1 cells were plated in 96-well half-area plates at 20,000 cells/well in complete growth media and cultured overnight. The next day, the growth media was replaced with dilution buffer (OptiMEM with 0.1% FBS) containing anti-NPR1 or iso-type control antibodies over a range of concentrations (0.017 nM-1 μM, with an additional condition without antibody) and incubated for 15 minutes at 37° C. After the pre-treatment, HEK293/hNPR1 cells were stimulated with ligand, ANP or BNP, over a range of concentrations (ANP=0.002-2 nM or BNP=0.0039-4 nM, with an additional condition without ligand) made in dilution buffer or dilution buffer containing 0.2 nM ANP or 0.7 nM BNP and incubated at 37° C. for 30 min.

The HTRF assay was performed using a cGMP HTRF kit (Cisbio, #62GM2PEH) according to manufacturer's instructions. The fluorescence intensity was detected using an EnVision multilabel plate reader (Perkin Elmer), and the fluorescence resonance energy transfer (FRET) ratio was calculated according to manufacturer's instructions. The FRET ratios were converted to cGMP concentrations in logarithmic scale according to the cGMP standard curve and analyzed using a 4-parameter logistic equation over a 10-point concentration-response curve to obtain the half maximal inhibitory concentration (IC50) values for the anti-NPR1 antibodies using GraphPad Prism 8. The half maximal effective concentration ($EC_{50}$) values of the ligand were not calculated due to the limit of quantitation at high concentrations. The maximal inhibition was calculated with the equation described below:

$$\% \text{ Maximal inhibition} = \frac{[\text{Log } cGMP, M]_{0.2nM\,ANP\,or\,0.7nM\,BNP} - [\text{Log } cGMP, M]_{1\,\mu M\,test\,antibody\,with\,ligand}}{[\text{Log } cGMP, M]_{0.2nM\,ANP\,or\,0.7nM\,BNP} - [\text{Log } cGMP, M]_{baseline}} \times 100$$

In this equation, $[\text{Log cGMP, M}]_{baseline}$, $[\text{Log cGMP, M}]_{1\,\mu M\,test\,antibody\,with\,ligand}$ and $[\text{Log cGMP, M}]_{0.2\,nM\,ANP\,or\,0.7\,nM\,BNP}$ are the cGMP concentration values in logarithmic scale from the cells treated with dilution buffer alone, the highest concentration of the anti-NPR1 antibodies at 1 μM with 0.2 nM ANP or 0.7 nM BNP, and 0.2 nM ANP or 0.7 nM BNP alone respectively.

Determination of the Mode of NPR1 Antagonism

The mode of anti-NPR1 antibody inhibition of ANP-mediated NPR1 activation was assessed by Schild analysis (Kenakin 1997 Pharmacologic Analysis of Drug-Receptor Interaction. 3rd edition. Philadelphia: Lippincott-Raven) of a cGMP accumulation assay. Conditions were optimized to have the ANP concentration response curves fall in the linear range of the cGMP standard curve. Briefly, HEK293/hNPR1 cells were lifted from the plates using an enzyme free cell dissociation solution. The cell suspension was then replated in low-volume 96-well plates at 1,000 cells/well in dilution buffer. Cells were then pre-treated with anti-NPR1 antibodies in dilution buffer at a fixed concentration of 0 nM, 50 nM, 150 nM or 450 nM for 15 minutes at room temperature. After the pre-treatment, ANP, at a range of concentrations (1.0 pM to 1 μM) in dilution buffer (with an additional condition without ANP), was added to the cells and incubated at room temperature for 5 minutes.

The HTRF assay, detection of fluorescence intensity and calculation of cGMP concentration were all performed as described previously. Using 96-well low-volume plates, the volumes necessary for the cGMP standard curve and detection reagents were half of those used with 96-well half-area plates.

All assay parameters were analyzed using GraphPad Prism 8. The $EC_{50}$ values of ANP in the presence or absence of anti-NPR1 antibodies were calculated using a 4-parameter logistic equation over a 11-point concentration-response curve. The decrease of ANP maximal response by anti-NPR1 antibodies was calculated using the equation:

$$\% \text{ } ANP \text{ Maximal response decrease} = \frac{[\text{Log } cGMP, M]_{1uM \text{ } ANP} - [\text{Log } cGMP, M]_{1 \text{ } uM \text{ } ANP \text{ with } 450nM \text{ antagonist}}}{[\text{Log } cGMP, M]_{1 \text{ } \mu M \text{ } ANP} - [\text{Log } cGMP, M]_{baseline}} \times 100$$

The Schild slope was determined by Schild plot analysis derived by plotting Log (concentration ratio-1) on the Y axis against the antagonist concentrations in logarithmic scale on the X axis. Concentration ratio is defined as the $EC_{50}$ values of ANP in the presence of antagonist at different concentrations divided by the $EC_{50}$ value of ANP in the absence of antagonist.

Analysis of Anti-NPR1 Antibody Mediated Internalization with Secondary Antibody-Drug Conjugates in a Cell-Based Cytotoxicity Assay Internalization of anti-NPR1 antibodies was indirectly assessed by a cytotoxicity assay using a secondary antibody conjugated with cytotoxic payload, Monomethyl auristatin F (MMAF). After binding NPR1 on cells, the anti-NPR1 antibody will internalize with the receptor, resulting in co-internalization of the anti-human Fc fab secondary antibody-drug conjugate (secondary ADC), release of the conjugated cytotoxic payload and killing of cells. Therefore, the extent of cytotoxicity can be used to assess the ability of the antibody to internalize upon target engagement.

For the assay, HEK293/hNPR1 cells were plated in 96-well white plates at 1,000 cells/well in complete growth media and cultured overnight. The next day, cells were pre-treated with anti-NPR1 or control antibodies over a range of concentrations (serial dilutions from 914 fM to 6 nM in dilution buffer, with an additional condition without antibody) in the presence or absence of 100 nM ANP or 100 nM BNP for 5 minutes at 37° C. After the pre-treatment, the secondary ADC at final concentration of 20 nM was added to HEK293/hNPR1 cells. To evaluate maximal killing in the assay, digitonin at final concentration of 48 μg/ml was added to control wells. The treated cells were incubated at 37° C. for three days.

To measure cell viability, Promega CellTiter-Glo was used according to manufacturer's instructions. The luminescence intensity was detected using an EnVision multilabel plate reader and analyzed using a 4-parameter logistic equation over a 9-point concentration-response curve to obtain the IC50 values of the anti-NPR1 antibodies using GraphPad Prism 8. The percentage of cell viability or cell kill was calculated using the equations described below:

$$\% \text{ Viability} = \frac{RLU_{dilution \text{ } buf,100 \text{ } nM \text{ } ANP \text{ } or \text{ } 100nM \text{ } BNP \text{ } alone} - RLU_{6 \text{ } nM \text{ } test \text{ } antibody}}{RLU_{dilution \text{ } buf,100 \text{ } nM \text{ } ANP \text{ } or \text{ } 100nM \text{ } BNP \text{ } alone} - RLU_{digitonin}} \times 100$$

$$\% \text{ Kill} = 100 - \% \text{ Viability}$$

Results

Evaluation of the Inhibition of Ligand Mediated NPR1 Activation by Anti-NPR1 Antibodies Both ANP and BNP activated HEK293/hNPR1 cells, stimulating cGMP accumulation in a concentration-dependent manner (FIGS. 1A and 1B). All the anti-NPR1 antibodies significantly blocked 0.2 nM ANP or 0.7 nM BNP induced NPR1 activation with IC50 values of 7.0-51 nM and maximal inhibition of 82%-107% (FIGS. 1A and 1B and Table 21). The isotype control antibody did not show any significant inhibition of 0.2 nM ANP or 0.7 nM BNP induced NPR1 activation (FIGS. 1A and 1B and Table 21).

TABLE 21

| Anti-NPR1 antibodies significantly inhibited ligand induced NPR1 activation as measured by cGMP accumulation assay | | | | |
| --- | --- | --- | --- | --- |
| | With 0.2 nM ANP | | With 0.7 nM BNP | |
| Antibody | $IC_{50}$, M | Max inh., % | $IC_{50}$, M | Max inh., % |
| H4H22034N | 2.00E−08 | 82 | 1.33E−08 | 99 |
| REGN7541 | 4.41E−08 | 90 | 1.49E−08 | 100 |
| REGN7544 | 5.13E−08 | 92 | 1.63E−08 | 107 |
| REGN7548 | 1.91E−08 | 92 | 7.02E−09 | 103 |
| Control mAb | ND | −1 | ND | −9 |

ND: not determined due to lack of concentration dependent changes in signal; Max Inh.: maximal inhibition.

Taken together, H4H22034N, REGN7541, REGN7544, and REGN7548 showed significant inhibition of ligand induced NPR1 activation as measured by the cGMP accumulation assay. Evaluation of the Mode by which anti-NPR1 antibodies Inhibit ANP Mediated NPR1 Activation Schild analysis was performed to determine the mode of anti-NPR1 antibody inhibition on ANP-mediated NPR1 activation. In the analysis, a parallel rightward shift of agonist concentration-response curves with a Schild slope of ~1 without altering the maximal response is indicative of a competitive antagonist. In contrast, an unparalleled rightward shift of agonist concentration-response curves with a Schild slope not close to one is indicative of a non-competitive antagonist. An antagonist that can change the maximal response of an agonist is defined as an insurmountable antagonist, while an antagonist that does not change the maximal response of an agonist is defined as a surmountable antagonist (Kenakin, 1997).

Using Schild analysis, H4H22034N, REGN7541, REGN7544 and REGN7548 demonstrated non-competitive inhibition of ANP agonist in a cGMP accumulation assay (FIGS. 2A-2E). Increasing the concentration of the four anti-NPR1 antibodies resulted in unparalleled rightward shifts of ANP concentration-response curves with Schild slopes that were not close to 1. In addition, inhibition by H4H22034N did not change the maximal response of ANP while inhibition by REGN7541, REGN7544 and REGN7548 decreased the maximal response of ANP to 10-62% (FIGS. 2A-2E and Table 22).

TABLE 22

| Anti-NPR1 antibodies showed non-competitive antagonism in Schild analysis | | |
|---|---|---|
| Antibody | Schild slope | % ANP Max decrease |
| H4H22034N | 0.05 | 0.1 |
| REGN7541 | 2.0 | 25.5 |
| REGN7544 | 2.6 | 61.6 |
| REGN7548 | 1.4 | 10.0 |

Taken together, H4H22034N, REGN7541, REGN7544 and REGN7548 demonstrated non-competitive antagonism with various effects on the maximum ligand response.

Evaluation of Anti-NPR1 Antibodies Induced NPR1 Internalization

Figures 3A, 3B:
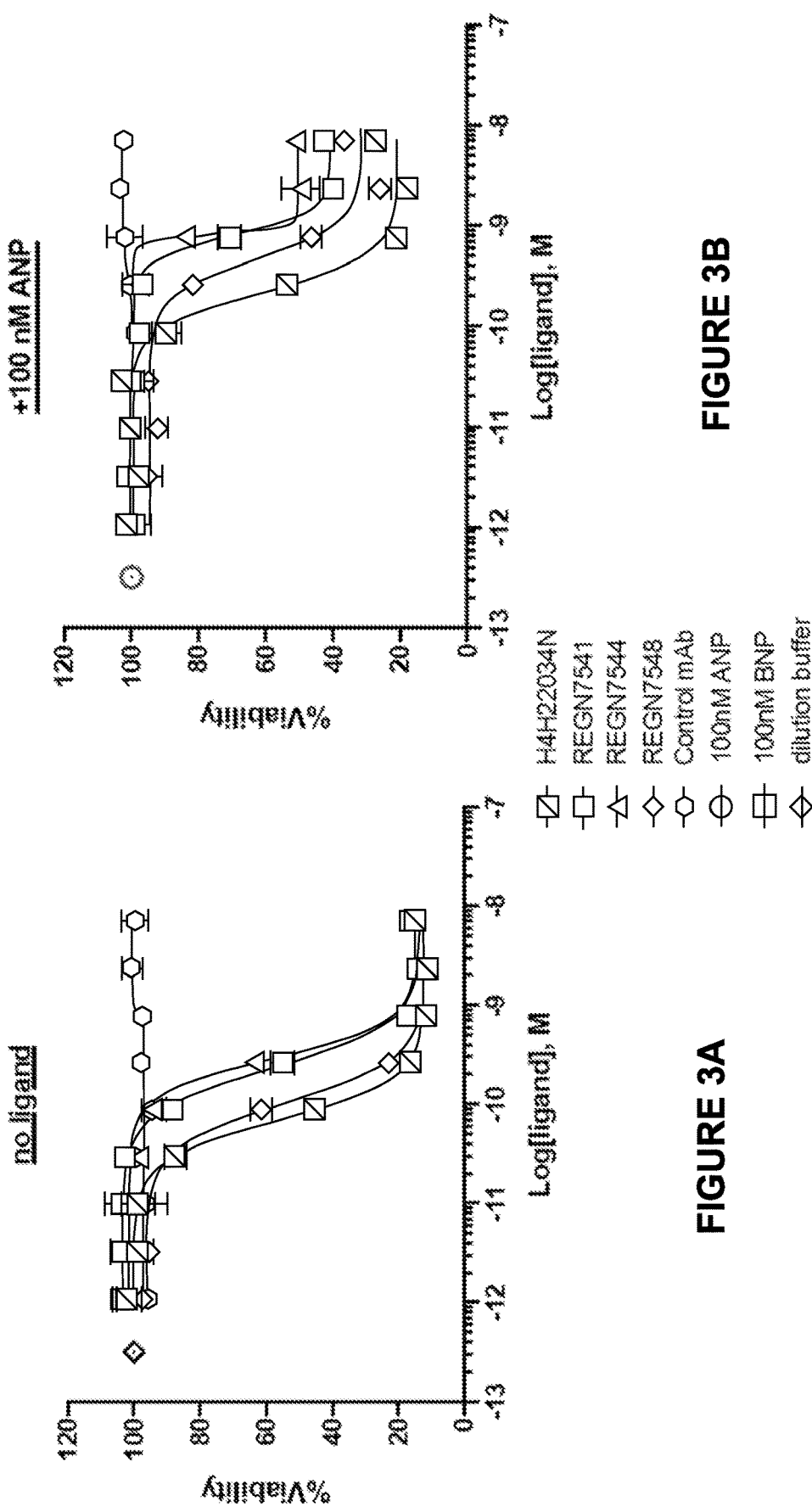
FIGS. 3A-3C show that anti-NPR1 antibodies induced NPR1 internalization as measured by cytotoxicity assay with secondary ADC (FIG. 3A) in the absence of ligand or in the presence of (FIG. 3B) 100 nM ANP or (FIG. 3C) 100 nM BNP. HEK293/hNPR1 cells were pre-treated with increasing concentrations of anti-NPR1 antibodies, control mAb, or dilution buffer alone in the presence or absence of 100 nM ANP or 100 nM BNP for 5 minutes at 37° C., followed with secondary ADC treatment for 3 days at 37° C. Experiment was performed in duplicate. Open symbols indicate conditions when no test article or only constant concentration of ANP or BNP was added, and closed symbols indicate conditions when the test article was added in a range of concentrations; dilution buffer: OptiMEM with 0.1% FBS.
Figure 3C:
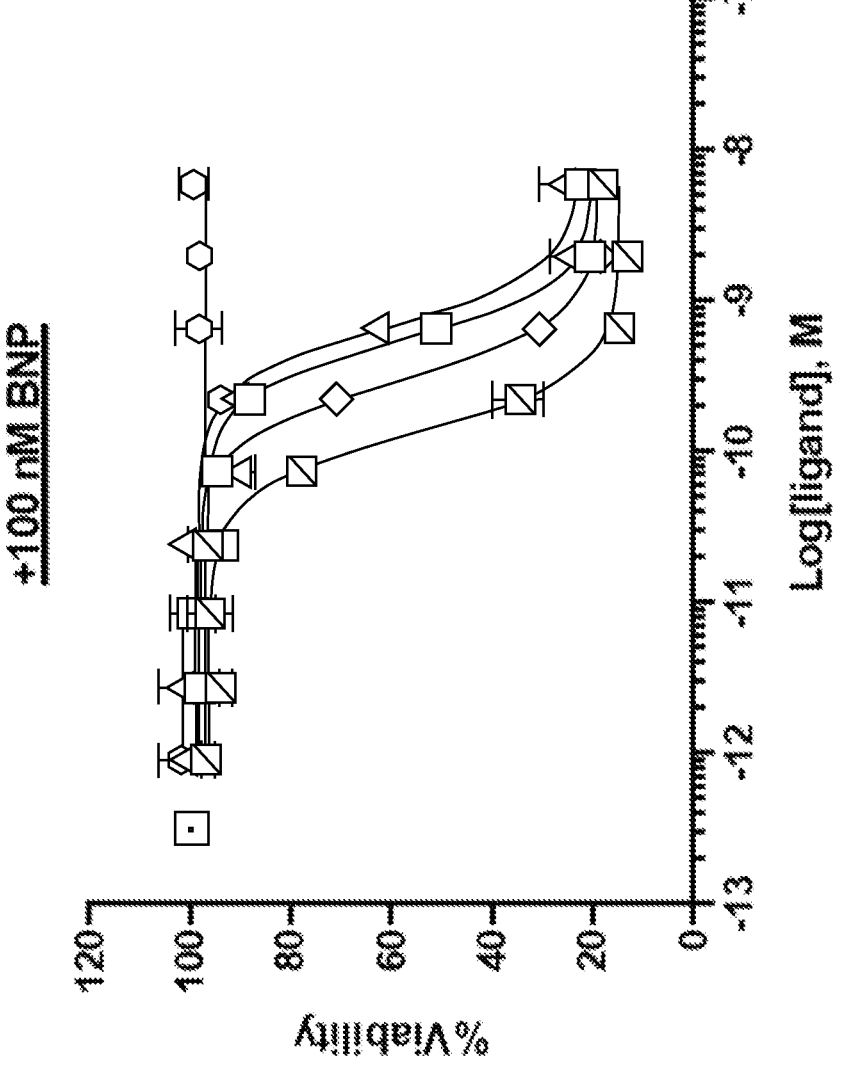

Internalization of the anti-NPR1 antibodies was assessed using a secondary ADC mediated cytotoxicity assay in the presence or absence of ligand. In the absence of ligand, all the anti-NPR1 antibodies induced NPR1 internalization in a concentration-dependent manner with IC50 values of 58-243 pM and maximal killing of 82%-85% (FIGS. 3A-3C and Table 23). In the presence of 100 nM ligand, the anti-NPR1 antibodies induced NPR1 internalization with IC50 values of 132-703 pM and maximal killing of 50%-82%. The isotype control antibody did not show any significant NPR1 internalization in the presence or absence of ligand (FIGS. 3A-3C and Table 23).

TABLE 23

| | Internalization of anti-NPR1 antibodies in the presence or absence of ligand as measured by secondary ADC mediated cytotoxicity assay | | | | | |
|---|---|---|---|---|---|---|
| | No ligand | | With 100 nM ANP | | With 100 nM BNP | |
| Antibody | $IC_{50}$, M | Max Kill, % | $IC_{50}$, M | Max Kill, % | $IC_{50}$, M | Max Kill, % |
| H4H22034N | 5.84E−11 | 85 | 1.85E−10 | 82 | 1.32E−10 | 82 |
| REGN7541 | 1.95E−10 | 83 | 6.67E−10 | 60 | 5.55E−10 | 78 |
| REGN7544 | 2.43E−10 | 82 | 7.03E−10 | 50 | 6.77E−10 | 74 |
| REGN7548 | 8.69E−11 | 85 | 3.97E−10 | 74 | 2.95E−10 | 79 |
| Control mAb | ND | 0.01 | ND | −4 | ND | 0.5 |

ND: not determined due to lack of concentration dependent changes in signal.

Taken together, H4H22034N, REGN7541, REGN7544 and REGN7548 showed anti-NPR1 antibody internalization of NPR1 in the presence or absence of ligand as measured by secondary ADC mediated cytotoxicity assay.

Example 7: Potency and Specificity of Anti-NPR1 Antibodies Binding to NPR1 Alone or in Complex with ANP or BNP on the Cell Surface Using Electrochemiluminescence-Based Detection

Experimental Procedure

The ability of anti-human NPR1 monoclonal antibodies to bind human or monkey (*Macaca fascicularis*) NPR1 (hNPR1 or mfNPR1) expressing cells in the presence or absence of human atrial (ANP) or human brain (BNP) natriuretic peptide ligands was determined using an electro-chemiluminescence (ECL) based immunoassay.

Briefly, HEK293/hNPR1 expressing cells were generated by transfecting human embryonic kidney (HEK) 293 cells with the neomycin resistant pLVX.hNPR1.myc.DDK plasmid encoding human NPR1 (amino acids M1-G1061, UniProtKB-P16066). Similarly, HEK293/mfNPR1 cells were generated by transfecting HEK293 cells with the neomycin resistant pRG984 plasmid encoding full-length monkey NPR1 (amino acids M1-G1061, accession number XP_005541809.1). The non-transfected HEK293 cell line, which showed no detectable binding of a commercial anti-hNRP1 antibody by fluorescence activated cell sorting (FACS), was included in the experiment as a non-specific binding control.

Experiments were carried out according to the following procedure. Cultures of the cell lines described above were rinsed once in 1×PBS buffer without $Ca^{2+}/Mg^{2+}$ and incubated for 10 minutes at 37° C. with Enzyme Free Cell Dissociation Solution to detach cells from the flask. The collected cell pellets were washed once with and resuspended in 1×PBS with $Ca^{2+}/Mg^{2+}$ and then cells were counted with a Cellometer™ Auto T4 cell counter (Nexcelom Bioscience, Lawrence, MA). Approximately $2.0×10^4$ cells per well were seeded onto 96-well carbon electrode plates (Meso Scale Diagnostics, Rockville, MD) and incubated for 1 hour at 37° C. Nonspecific binding sites were blocked using 2% BSA (w/v) in 1×PBS containing $Ca^{2+}/Mg^{2+}$ for 1 h at room temperature. Subsequently, HEK293/hNPR1 and HEK293/mfNPR1 cells were incubated for 0.5 hour at room temperature with 10 nM hANP (Tocris, Minneapolis, MN), 100 nM hBNP (Tocris, Minneapolis, MN), or sample dilution buffer alone, while HEK293 cells were treated with sample dilution buffer only. Without washing, serial dilutions of anti-NPR1, Comparator 1 or the isotype control antibody, ranging from 1.7 pM to 100 nM, or buffer containing no antibody were added to the cells followed by 1 hour incubation at room temperature. Plates were then washed to remove unbound antibodies, hANP, and hBNP using an AquaMax2000 plate washer with a cell washing head (MDS Analytical Technologies, Sunnyvale, CA). The plate-bound antibodies were detected with a SULFO-TAG™-conjugated polyclonal goat anti-human IgG antibody specific for heavy and light chains (Jackson Immunoresearch, West Grove, PA) that was incubated with the cells for 1 hour at room temperature.

After washes, plates were developed with Read Buffer (Meso Scale Diagnostics, Rockville, MD) according to manufacturer's recommended procedure and luminescent signals were recorded with a SECTOR Imager 600 (Meso Scale Diagnostics, Rockville, MD). The binding signals in a unit of RLU were analyzed as a function of the antibody concentration and data were fitted with a sigmoidal (four-parameter logistic) dose-response model using R statistical package (open source). The $EC_{50}$ value, defined as the concentration of antibody at which 50% of the maximal binding signal is detected, was determined to indicate binding potency of the anti-NPR1 antibodies to NPR1 expressing cells with or without ANP or BNP complexed to NPR1 on the cell surface.

Results

The ability of the anti-NPR1 monoclonal antibodies to bind specifically to the surface of HEK293 cells engineered to express human or monkey NPR1 in the presence or absence of ANP or BNP was assessed using an electrochemi-luminescence-based immunoassay. The concentration dependence of antibody binding was analyzed and $EC_{50}$ values were determined.

The results are summarized in Table 24.

In contrast, the Comparator 1 exhibited binding specificity to hNPR1 cells only when hANP or hBNP were present (10 nM hANP or 100 nM hBNP), with $EC_{50}$ values of 0.57 nM and 1.8 nM, respectively, and no detectable binding was observed in the absence of hANP and hBNP, hence it is classified as NPR1-ANP/BNP complex only binder.

Anti-NPR1 antibodies H4H22034, REGN7541, REGN7544, REGN7548 also bound to the monkey NPR1 expressing cells (HEK293/mfNPR1) with $EC_{50}$ values ranging from 0.33 nM to 1.7 nM. Similar to hNPR1 cells, addition of 10 nM hANP or 100 nM of hBNP did not affect anti-NPR1 antibody binding to HEK293/mfNPR1 cells; $EC_{50}$ values for antibody binding ranged from 0.67 nM to 4.2 nM or 0.42 nM to 1.7 nM in the presence of hANP and hBNP, respectively (Table 24) and no binding was detected for any of the antibodies on the parental HEK293 cells. In contrast, the Comparator 1 specifically bound to HEK293/mfNPR1 engineered cells only in the presence of 10 nM hANP or 100 nM hBNP, however, $EC_{50}$ values could not be determined due to the concentration dependent binding curve lacking sigmoidal curvature and data could not be fitted with the binding model.

In the experiment the isotype control did not bind to HEK293/hNPR1, HEK293/mfNPR1 nor HEK293 cells.

TABLE 24

Potency of Anti-NPR1 Antibodies Binding to NPR1 Expressing Cells in the Presence or Absence of NPR1 Ligands.

| | | Cell Binding Potency, $EC_{50}$ (M) | | | | | |
|---|---|---|---|---|---|---|---|
| | | HEK293/hNPR1 | | | HEK293/mfNPR1 | | |
| Antibody | Experiment | No ligand added | +10 nM hANP | +100 nM hBNP | No ligand added | +10 nM hANP | +100 nM hBNP |
| H4H22034 | 1 | 3.4E−10 | 5.6E−10 | 4.3E−10 | 3.3E−10 | 6.7E−10 | 4.2E−10 |
| REGN7541 | 1 | 1.3E−09 | 2.1E−09 | 1.1E−09 | 1.4E−09 | 2.9E−09 | 9.2E−10 |
| REGN7544 | 1 | 1.7E−09 | 2.9E−09 | 1.5E−09 | 1.7E−09 | 4.2E−09 | 1.7E−09 |
| REGN7548 | 2 | 6.8E−10 | 1.2E−09 | 8.1E−10 | 5.6E−10 | 1.2E−09 | 5.6E−10 |
| Comparator 1 | 2 | NB | 5.7E−10 | 1.8E−09 | NB | INC | INC |
| Isotype control | 2 | NB | NB | NB | NB | NB | NB |

Abbreviations: NB—no binding; INC—inconclusive: $EC_{50}$ value could not be calculated due to the data lacking sigmoidal curvature to be fitted with the sigmoidal dose-response model (4 parameters sigmoidal curve fit), but the antibody displayed marginal specific binding to mfNPR1 expressing cells in the presence of 10 nM hANP or 100 nM hBNP.

Four anti-NPR1 antibodies (H4H22034, REGN7541, REGN7544, REGN7548) of the disclosure bound to the human NPR1 engineered cells in the presence of 10 nM hANP or 100 nM hBNP. The potency of these antibodies on HEK293/hNPR1.myc.DDK cells in the presence of 10 nM hANP or 100 nM hBNP ranged from $EC_{50}$ values of 0.56 nM to 2.9 nM or 0.43 nM to 1.5 nM, respectively (Table 24). Similar binding potencies were determined on hNPR1 expressing cells in the absence of hANP and hBNP, with $EC_{50}$ values ranging from 0.34 nM to 1.7 nM. No detectable binding was observed for these antibodies on parental HEK293 cells under the same experimental conditions. These results suggest that the antibodies are NPR1 specific binders, and that the human NPR1 binding potency for these antibodies is not affected by the presence of ANP or BNP.

Example 8: Characterization of the Acute Effects on Systemic Blood Pressure Following a Single 25 mg/Kg Intravenous Dose of an NPR1 Antagonist mAb in Normotensive Telemetered NPR1$^{hu/Hu}$ Mice Experimental Procedure The objectives of this study were to assess the acute effects of NPR1 antagonist antibodies on baseline systemic blood pressure in telemetered normotensive NPR1$^{hu/hu}$ mice. Male NPR1$^{hu/hu}$ (n=30) mice aged ~14-16 weeks were implanted with PA-C10 telemeters (DSI, St. Paul, MN) and allowed to recover for at least 7 days. Animals were stratified into groups (Groups 1-5) based on body weight (Table 25). Animals were individually housed under standard conditions (Temperatures of 64° F. to 84° F. (18° C. to 29° C.);

relative humidity of 30% to 70%) and a 12 hour light/12 hour dark cycle was maintained. Food (Research Diets Standard pellet chow) and water were provided ad libitum.

TABLE 25

| | | | Dose | Number of |
| Group No. | Test or Control Article | Dose Level (mg/kg/dose) | Volume (mL/kg) | Animals Males |
|---|---|---|---|---|
| | | Summary of Doses and Dose Groups | | |
| 1 | PBS | 0 | 5 | 6 |
| 2 | H4H22034N | 25 | | 6 |
| 3 | REGN7541 | | | 6 |
| 4 | REGN7544 | | | 6 |
| 5 | REGN7548 | | | 6 |

The test proteins were administered to the appropriate animals by single intravenous injection on Day 0. The dose volume for each animal was based on the most recent body weight measurement.

Systolic pressure, diastolic pressure, mean arterial pressure, pulse pressure and heart rate were collected for 10 seconds every minute for the duration of the testing period. Telemetry data are presented as mean 60-min or 24-hour values. All data are presented as mean±SEM.

Results

Figure 4:
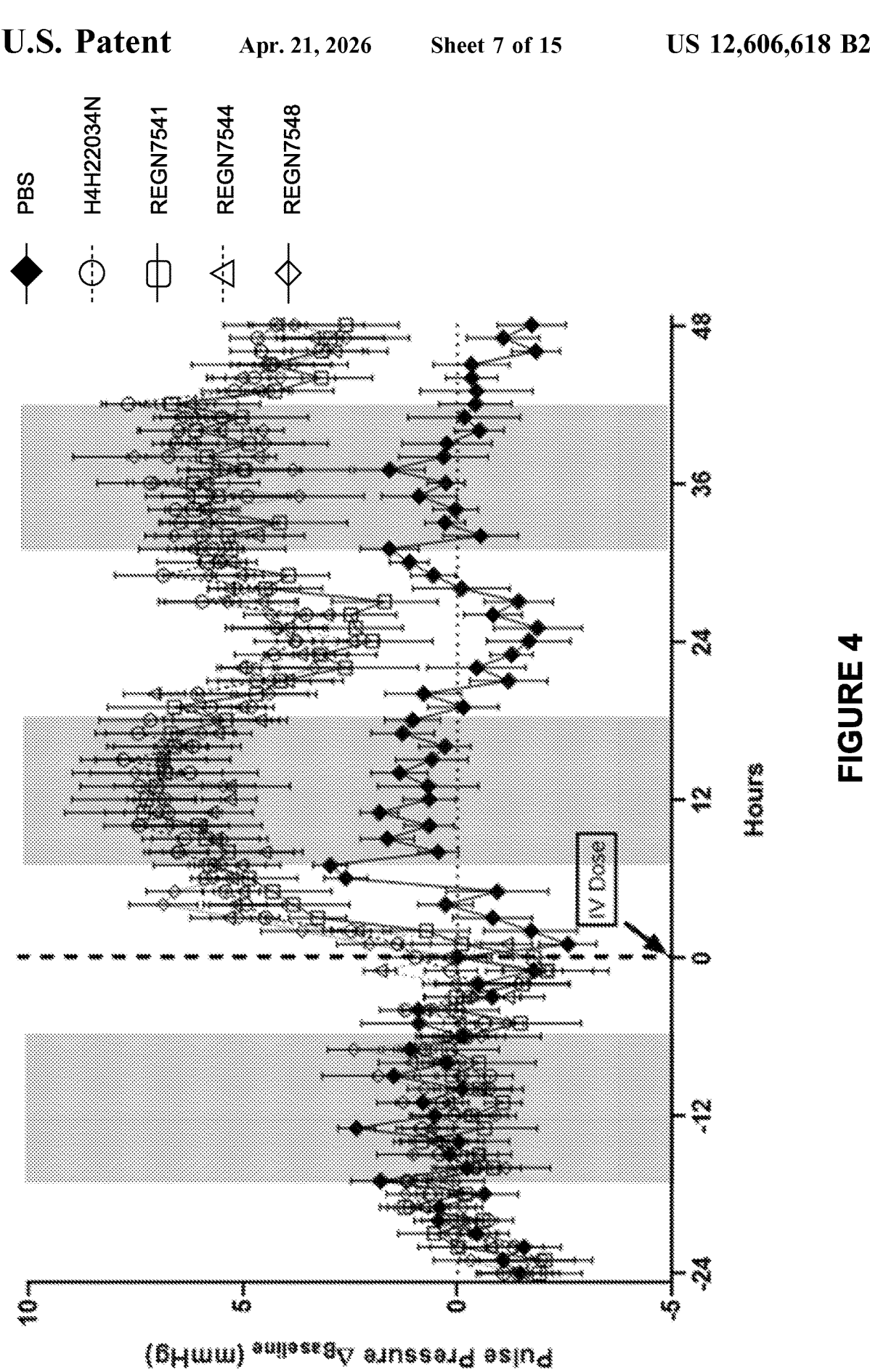
FIG. 4 shows the acute effects of NPR1 antagonist mAb's on pulse pressures in normotensive NPR1$^{hu/hu}$ mice-single 25 mg/kg dose. Telemetered normotensive NPR1$^{hu/hu}$ mice were randomized into groups based on body weight. Animals were given a single 25 mg/kg intravenous injection of an NPR1 antagonist mAb or PBS as described in Table 25. All values are mean±SEM, n=6 per group.
Figure 5:
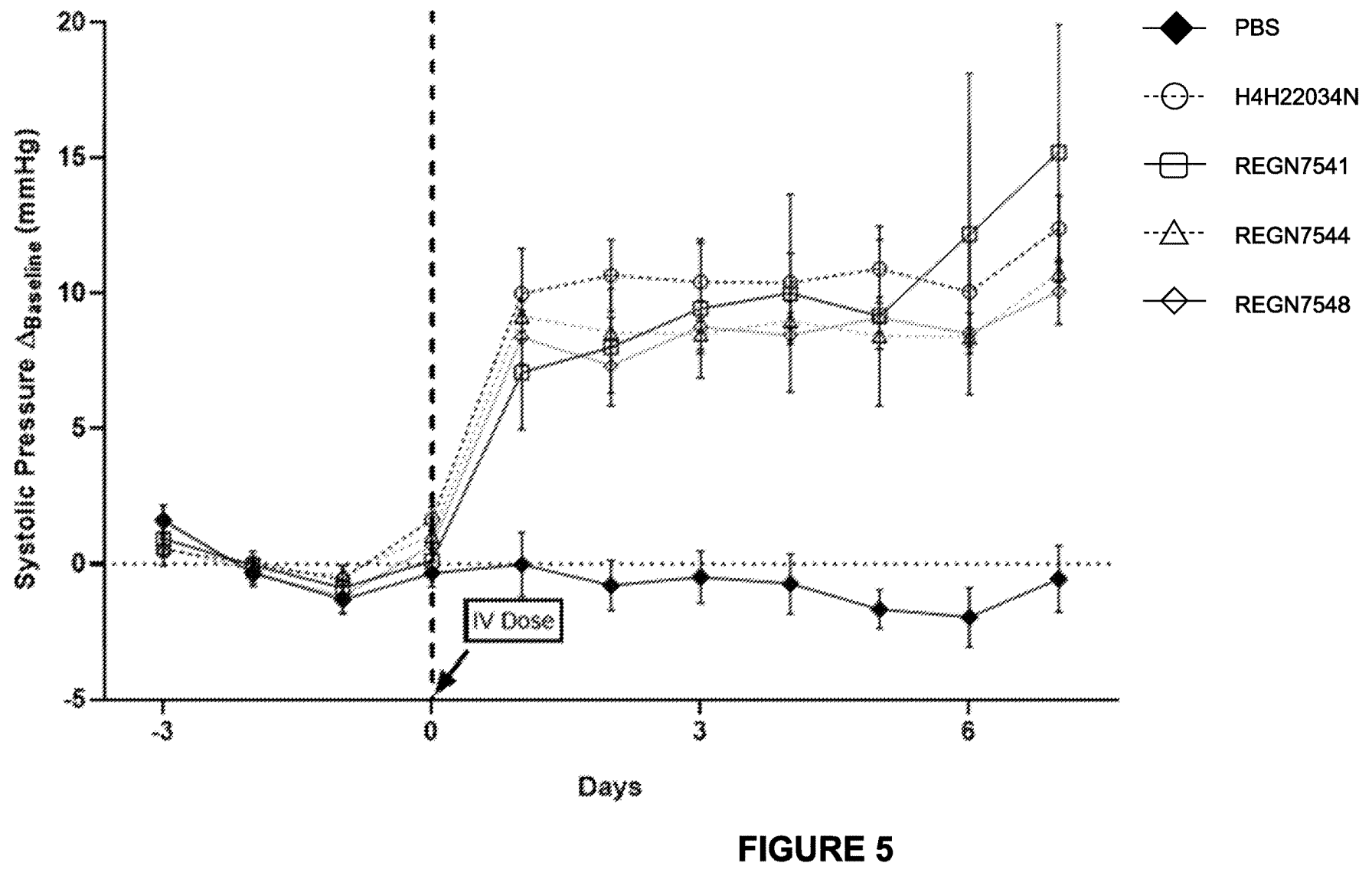

The in vivo assessment demonstrated that when compared to PBS control, animals dosed with an NPR1 antagonist antibody had rapid and persistent increases of systemic blood pressure (FIG. 4) following a single intravenous dose of any of the antibodies assessed. The pressures changes occurred almost immediately (FIG. 4), and last through day 7 of the study, the duration of the experiment (FIG. 5). The magnitude of acute blood pressure increase as assessed by mean (of 48-hours post-dose) systolic blood pressure change from baseline ranged from +7.64±1.13 (REGN7541) to +9.81±1.03 (H4H22034N) mmHg. The magnitude of blood pressure increase as assessed by mean (of 7-days post-dose) systolic blood pressure change from baseline ranged from +7.65±1.03 (REGN7548) to +9.55±1.16 (H4H22034N) mmHg.

Diastolic, mean arterial and pulse pressures (Table 26 and Table 27) were also significantly changed following dosing of NPR1 blocking mAbs, with magnitudes and durations of effect consistent with that observed and reported on systolic blood pressures. Heart rate responses were variable (Table 26 and Table 27), with acute changes generally trending toward a greater reduction in rate relative to baseline. These changes are consistent with the observed increase in pressure. Assessment of heart rate out 7 days demonstrated a significant relative increase for animals that received REGN7548.

TABLE 26

48-Hour Post Dose Mean Change from Baseline Blood Pressures and Heart Rates

| Dose Group: | Dose (mg/kg) | Systolic (mmHg) | Diastolic (mmHg) | Mean Arterial (mmHg) | Pulse Pressure (mmHg) | Heart Rate (BPM) |
|---|---|---|---|---|---|---|
| PBS | 0 | 0.08 ± 1.0 | 0.04 ± 0.89 | 0.03 ± 0.95 | 0.04 ± 0.17 | −10.02 ± 6.85 |
| H4H22034N | 25 | 9.81 ± 1.03**** | 4.30 ± 0.89**** | 7.22 ± 0.96**** | 5.51 ± 0.21**** | −22.80 ± 6.75 |
| REGN7541 | | 7.64 ± 1.13**** | 3.01 ± 0.95**** | 5.62 ± 1.04**** | 4.55 ± 0.28**** | −14.38 ± 8.59 |
| REGN7544 | | 8.68 ± 1.03**** | 3.79 ± 0.94**** | 6.42 ± 0.98**** | 4.89 ± 0.22**** | −17.91 ± 7.22 |
| REGN7548 | | 7.87 ± 1.08**** | 2.78 ± 0.94*** | 5.55 ± 1.01**** | 5.09 ± 0.22**** | −11.44 ± 6.73 |

Telemetered normotensive NPR1$^{hu/hu}$ mice were randomized into groups based on body weight. Animals were given a single 25 mg/kg intravenous injection of NPR1 antagonist mAb or PBS as described in Table 25. All values are mean ± SEM, n = 6 per group. Statistics - two way ANOVA with Dunnett's; *p < .05 vs. PBS.

TABLE 27

7-day Post Dose Mean Change from Baseline Blood Pressures and Heart Rates

| Dose Group: | Dose (mg/kg) | Systolic (mmHg) | Diastolic (mmHg) | Mean Arterial (mmHg) | Pulse Pressure (mmHg) | Heart Rate (BPM) |
|---|---|---|---|---|---|---|
| PBS | 0 | −0.82 ± 0.24 | −0.26 ± 0.17 | −0.66 ± 0.20 | −0.56 ± 0.15 | −21.98 ± 3.75 |
| H4H22034N | 25 | 9.55 ± 1.16**** | 4.79 ± 0.49**** | 7.19 ± 0.83**** | 4.76 ± 0.70**** | −22.75 ± 3.93 |
| REGN7541 | | 8.89 ± 1.54**** | 5.44 ± 1.12**** | 7.19 ± 1.27**** | 3.45 ± 0.64*** | −18.41 ± 4.51 |
| REGN7544 | | 7.97 ± 1.03**** | 3.85 ± 0.64**** | 5.96 ± 0.80**** | 4.12 ± 0.63**** | −22.53 ± 4.89 |
| REGN7548 | | 7.65 ± 1.03**** | 3.44 ± 0.47**** | 5.66 ± 0.75**** | 4.21 ± 0.62**** | −9.54 ± 3.25*** |

Telemetered normotensive NPR1$^{hu/hu}$ mice were randomized into groups based on body weight. Animals were given a single 25 mg/kg intravenous injection of NPR1 antagonist mAb or PBS as described in Table 25. All values are mean ± SEM, n = 6 per group. Statistics - two way ANOVA with Dunnett's; *p < .05 vs. PBS.

NPR1 antagonist antibodies H4H22034N, REGN7541, REGN7544 and REGN7548 significantly and rapidly increased systemic blood pressures within hours following a single subcutaneous injection to normotensive NPR1$^{hu/hu}$ mice. The observed hemodynamic effects lasted the duration of the 7 day experiment.

Example 9: Characterization of the Effect on Systemic Blood Pressure of a Single 1 or 25 Mg/Kg Dose of an NPR1 Antagonist mAb in Normotensive NPR1$^{hu/Hu}$ Mice

Experimental Procedure

The objectives of this study were to assess the effects of NPR1 antagonist antibodies on baseline systemic blood pressure in telemetered normotensive NPR1$^{hu/hu}$ mice. Male NPR1$^{hu/hu}$ (n=54) mice aged ~20-24 weeks were implanted with PA-C10 telemeters (DSI, St. Paul, MN) and allowed to recover for at least 7 days. Animals were stratified into groups (Groups 1-10) based on body weight and baseline systolic and pule pressures, prior to being assigned to group (Table 28). Animals were individually housed under standard conditions (Temperatures of 64° F. to 84° F. (18° C. to 29° C.); relative humidity of 30% to 70%) and a 12-hour light/12-hour dark cycle was maintained. Food (Research Diets Standard pellet chow) and water were provided ad libitum.

TABLE 28

| | Summary of Doses and Dose Groups | | | |
|---|---|---|---|---|
| Group No. | Test or Control Article | Dose Level (mg/kg/dose) | Dose Volume (mL/kg) | Number of Animals Males |
| 1 | PBS | 0 | 5 | 5 |
| 2 | IgG4P isotype control mAb | 25 | | 5 |
| 3 | H4H22034N | 1 | | 5 |

TABLE 28-continued

| | Summary of Doses and Dose Groups | | | |
|---|---|---|---|---|
| Group No. | Test or Control Article | Dose Level (mg/kg/dose) | Dose Volume (mL/kg) | Number of Animals Males |
| 4 | REGN7541 | | | 5 |
| 5 | REGN7544 | | | 5 |
| 6 | REGN7548 | | | 5 |
| 7 | H4H22034N | 25 | | 6 |
| 8 | REGN7541 | | | 6 |
| 9 | REGN7544 | | | 6 |
| 10 | REGN7548 | | | 6 |

The test proteins were administered to the appropriate animals by single subcutaneous injection on Day 0. The dose volume for each animal was based on the most recent body weight measurement.

Systolic pressure, diastolic pressure, mean arterial pressure, pulse pressure and heart rate were collected for 10 seconds every 10 minutes for the duration of the testing period. Telemetry data are presented as mean 24-hour values. All data are presented as mean±SEM.

Results

Figure 6:
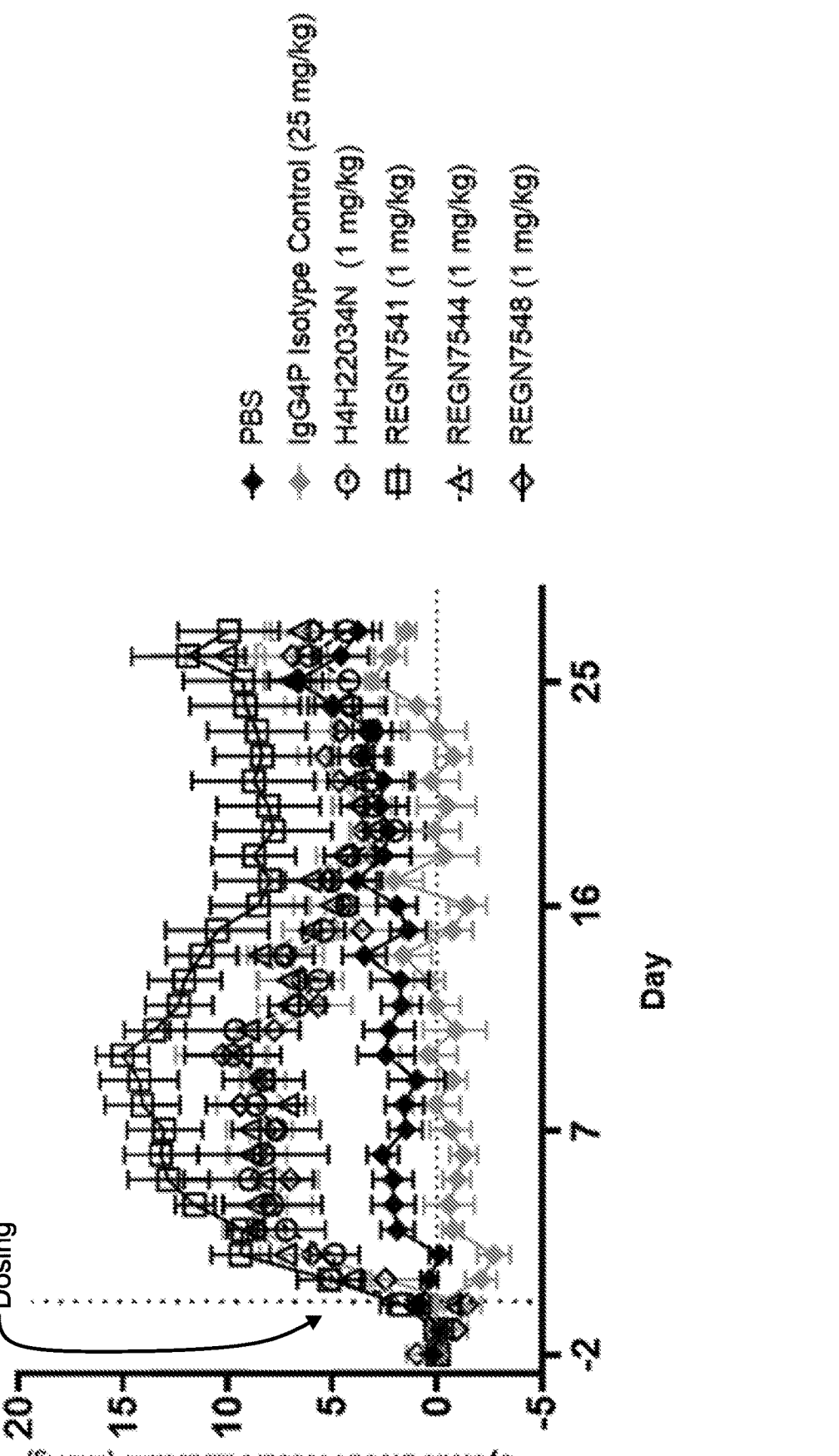
FIG. 6 show the effects of NPR1 antagonist mAb's on systolic blood pressures in normotensive NPR1$^{hu/hu}$ Mice-single 1 mg/kg dose. Telemetered normotensive NPR1$^{hu/hu}$ mice were randomized into groups based on body weight. Animals were given a single 1 mg/kg subcutaneous injection of an NPR1 antagonist mAb or single 25 mg/kg injection of IgG4P isotype control mAb as described in Table 28. All values are mean±SEM, n=4-5 per group.
Figure 7:
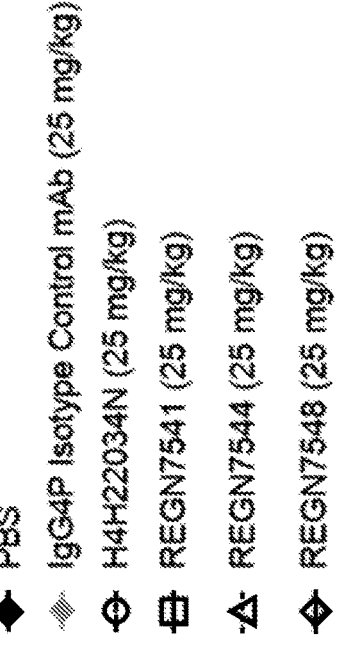
FIG. 7 shows the effects of NPR1 antagonist mAb's on systolic blood pressures in normotensive NPR1$^{hu/hu}$ mice-single 25 mg/kg dose. Telemetered normotensive NPR1$^{hu/hu}$ mice were randomized into groups based on body weight. Animals were given a single 25 mg/kg subcutaneous injection of an NPR1 antagonist mAb or IgG4P isotype control mAb as described in Table 28. All values are mean±SEM, n=4-5 per group.
Figure 7:
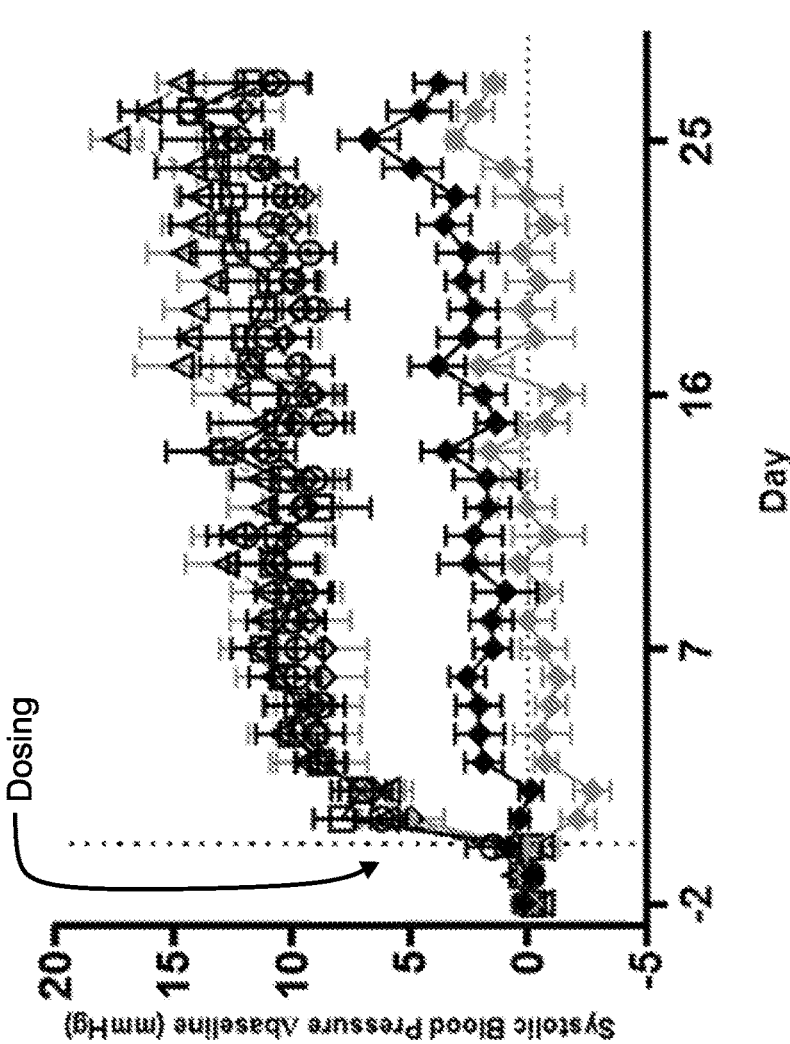

The in vivo characterization of NPR1 antagonist antibodies demonstrated that when compared to IgG4P isotype and PBS control-dosed animals, NPR1 antagonist-dosed NPR1$^{hu/hu}$ mice presented with significant and persistent increases of systemic blood pressure following a single subcutaneous dose of 1 or 25 mg/kg of any NPR1 antagonist antibody evaluated (Table 29, Table 30, FIG. 6, FIG. 7). The magnitude of blood pressure increase following a single subcutaneous 1 mg/kg dose as assessed by mean (of days 0 to 14 post-dose) systolic blood pressure change from baseline ranged from +6.81±0.76 (REGN7548) to +11.22±0.93 (REGN7541) mmHg (Table 29 and FIG. 6). The magnitude of blood pressure increase following a single subcutaneous 25 mg/kg dose as assessed by mean (of days 0 to 14 post-dose) systolic blood pressure change from baseline ranged from +8.82±0.64 (H4H22034) to +9.76±0.92 (REGN7544) mmHg (Table 29 and FIG. 7).

TABLE 29

| | | | 14-day Post Dose Mean Change from Baseline Blood Pressures and Heart Rates | | | |
|---|---|---|---|---|---|---|
| Dose Group: | Dose (mg/kg) | Systolic (mmHg) | Diastolic (mmHg) | Mean Arterial (mmHg) | Pulse Pressure (mmHg) | Heart Rate (BPM) |
| PBS | 0 | 1.69 ± 0.23 | −0.39 ± 0.14 | 0.57 ± 0.13 | 2.07 ± 0.19 | −6.52 ± 2.45 |
| IgG4P isotype control mAb | 25 | −0.53 ± 0.27**** | 0.26 ± 0.26 | −0.03 ± 0.26 | −0.80 ± 0.09**** | −4.92 ± 1.78 |
| H4H22034N | 1 | 7.10 ± 0.60**** | 3.81 ± 0.43**** | 5.55 ± 0.51**** | 3.29 ± 0.30 | −16.51 ± 3.24 |
| REGN7541 | | 11.22 ± 0.93**** | 7.23 ± 0.69**** | 9.29 ± 0.78**** | 4.0 ± 0.41*** | −0.48 ± 2.74 |
| REGN7544 | | 7.39 ± 0.67**** | 4.00 ± 0.39**** | 5.82 ± 0.51**** | 3.39 ± 0.37* | −1.43 ± 2.74 |
| REGN7548 | | 6.81 ± 0.76**** | 3.91 ± 0.84**** | 5.36 ± 0.68**** | 2.93 ± 0.68 | −9.06 ± 1.90 |
| H4H22034N | 25 | 8.82 ± 0.64**** | 4.55 ± 0.58**** | 6.70 ± 0.56**** | 4.29 ± 0.32**** | −7.45 ± 2.48 |
| REGN7541 | | 9.24 ± 0.76**** | 5.77 ± 0.61**** | 7.47 ± 0.66**** | 3.50 ± 0.33 | −12.63 ± 2.45 |
| REGN7544 | | 9.76 ± 0.92**** | 3.13 ± 0.42**** | 6.51 ± 0.64**** | 6.66 ± 0.54**** | −21.61 ± 3.17**** |
| REGN7548 | | 8.37 ± 0.69**** | 3.61 ± 0.38**** | 6.14 ± 0.52**** | 4.77 ± 0.35**** | −12.43 ± 2.32 |

Telemetered normotensive NPR1$^{hu/hu}$ mice were randomized into groups based on body weight. Animals were given a single 1 or 25 mg/kg subcutaneous injection of NPR1 antagonist mAb, isotype control or PBS as described in Table 28. All values are mean ± SEM, n = 4-5 per group. Statistics - two way ANOVA with Dunnett's; *p < .05 vs. PBS.

TABLE 30

| | Dose (mg/kg) | Systolic (mmHg) | Diastolic (mmHg) | Mean Arterial (mmHg) | Pulse Pressure (mmHg) | Heart Rate (BPM) |
|---|---|---|---|---|---|---|
| Dose Group: | | | | | | |

15- through 27-day Post Dose Mean Change from Baseline Blood Pressures and Heart Rates

| Dose Group: | Dose (mg/kg) | Systolic (mmHg) | Diastolic (mmHg) | Mean Arterial (mmHg) | Pulse Pressure (mmHg) | Heart Rate (BPM) |
|---|---|---|---|---|---|---|
| PBS | 0 | 3.37 ± 0.40 | −0.17 ± 0.35 | 1.45 ± 0.36 | 3.55 ± 0.07 | −30.93 ± 1.85 |
| IgG4P isotype control mAb | 25 | 0.50 ± 0.38**** | 0.44 ± 0.35 | 0.49 ± 0.35 | 0.07 ± 0.07**** | −25.24 ± 1.95 |
| H4H22034N | 1 | 4.04 ± 0.30 | 1.50 ± 0.28 | 2.62 ± 0.28 | 2.55 ± 0.20 | −41.12 ± 2.29* |
| REGN7541 | | 9.03 ± 0.32**** | 5.83 ± 0.51**** | 7.44 ± 0.49**** | 3.60 ± 0.21 | −24.76 ± 1.89 |
| REGN7544 | | 5.20 ± 0.54* | 5.02 ± 0.42**** | 4.95 ± 0.47**** | 0.16 ± 0.32**** | −15.75 ± 2.68** |
| REGN7548 | | 4.79 ± 0.34 | 3.47 ± 0.31**** | 3.92 ± 0.30*** | 1.36 ± 0.19* | −19.30 ± 1.86** |
| H4H22034N | 25 | 10.53 ± 0.43**** | 5.38 ± 0.42**** | 7.78 ± 0.42**** | 5.17 ± 0.15** | −29.57 ± 2.31 |
| REGN7541 | | 12.05 ± 0.32**** | 9.36 ± 0.44**** | 10.29 ± 0.35**** | 2.73 ± 0.23 | −31.24 ± 1.97 |
| REGN7544 | | 14.20 ± 0.42**** | 4.94 ± 0.36**** | 9.43 ± 0.37**** | 9.30 ± 0.14**** | −41.43 ± 2.15** |
| REGN7548 | | 10.58 ± 0.29**** | 4.71 ± 0.25**** | 7.52 ± 0.26**** | 5.89 ± 0.10**** | −35.53 ± 1.75 |

Telemetered normotensive NPR1$^{hu/hu}$ mice were randomized into groups based on body weight. Animals were given a single 1 or 25 mg/kg subcutaneous injection of NPR1 antagonist mAb, isotype control or PBS as described in Table 28. All values are mean ± SEM, n = 4-5 per group. Statistics - two way ANOVA with Dunnett's; *p < .05 vs. PBS.

Chronic effects of these NPR1 antagonist antibodies were evaluated over 27 days (Table 30 and FIG. 6 and FIG. 7). Following a single subcutaneous 1 mg/kg injection on day 0, systemic blood pressure remained significantly elevated for 3 of the 4 NPR1 blocking mAb's evaluated for the duration of the testing period (Table 30 and FIG. 6). The magnitude of blood pressure increase following a single subcutaneous 1 mg/kg dose as assessed by mean (of days 15 to 27 post-dose) systolic blood pressure change from baseline ranged from +4.04±0.30 (H4H22034) to +9.03±0.32 (REGN7541) mmHg. Following a single subcutaneous 25 mg/kg injection on day 0, systemic blood pressure remained significantly elevated for all NPR1 blocking mAb's evaluated. The magnitude of blood pressure increase following a single subcutaneous 25 mg/kg dose as assessed by mean (of days 15 to 27 post-dose) systolic blood pressure change from baseline ranged from +10.53±0.43 (H4H22034) to +14.2±0.42 (REGN7544) mmHg. Heart rate responses were variable (Table 29 and Table 30), with general trends of rate reductions consistent with the observed increase of systemic blood pressures. Diastolic, mean arterial and pulse pressures (Table 29 and Table 30) were also significantly changed following dosing of NPR1 blocking mAbs, with magnitudes and durations of effect consistent with that observed and reported on systolic blood pressures.

NPR1 antagonist antibodies H4H22034N, REGN7541, REGN7544 and REGN7548 significantly increased systemic blood pressures for up to 27 days following a single subcutaneous injection to normotensive NPR1$^{hu/hu}$ mice.

Example 10: Characterization of the Effect on Systemic Blood Pressure of Overexpression of ANP Via Hydrodynamic DNA Delivery and Ability to Reverse Effects Following a Single 25 Mg/Kg Dose of an NPR1 Antagonist mAb in Hypotensive NPR1$^{hu/Hu}$ Mice Experimental Procedure The objectives of this study were to assess the effects of NPR1 antagonist antibodies and their ability to reverse the blood pressure-lowering effects of ANP over expression in telemetered hypotensive NPR1$^{hu/hu}$ mice. Male NPR1$^{hu/hu}$ (n=48) mice aged ~12-16 weeks were implanted with PA-C10 telemeters (DSI, St. Paul, MN) and allowed to recover for at least 7 days. Animals were stratified into groups (Groups 1-6) based on body weight (Table 31). Animals were individually housed under standard conditions (Temperatures of 64° F. to 84° F. (18° C. to 29° C.); relative humidity of 30% to 70%) and a 12-hour light/12-hour dark cycle was maintained. Food (Research Diets Standard pellet chow) and water were provided ad libitum.

TABLE 31

| | | | | | | |
|---|---|---|---|---|---|---|
| Group No. | HDD Construct | HDD Construct Dose (μg DNA, i.v.) | Test or Control Article | Dose Level (mg/kg/dose, i.v.) | Dose Volume (mL/kg) | Number of Animals Males |
| 1 | Control plasmid | 50 | Isotype | 25 | 5 | 8 |
| 2 | ANP plasmid | | control mAb | | | 8 |
| 3 | | | H4H22034N | | | 8 |
| 4 | | | REGN7541 | | | 8 |
| 5 | | | REGN7544 | | | 8 |
| 6 | | | REGN7548 | | | 8 |

Summary of Doses and Dose Groups

The HDD plasmids and test proteins were administered to the appropriate animals by single intravenous injections on Day 0 and Day 7, respectively. The dose volume for administration of test proteins was based on the most recent body weight measurement.

Systolic pressure, diastolic pressure, mean arterial pressure, pulse pressure and heart rate were collected for 10 seconds every minute for the duration of the testing period.

Telemetry data are presented as mean 24-hour values. All data are presented as mean±SEM.

Results

Figure 8:
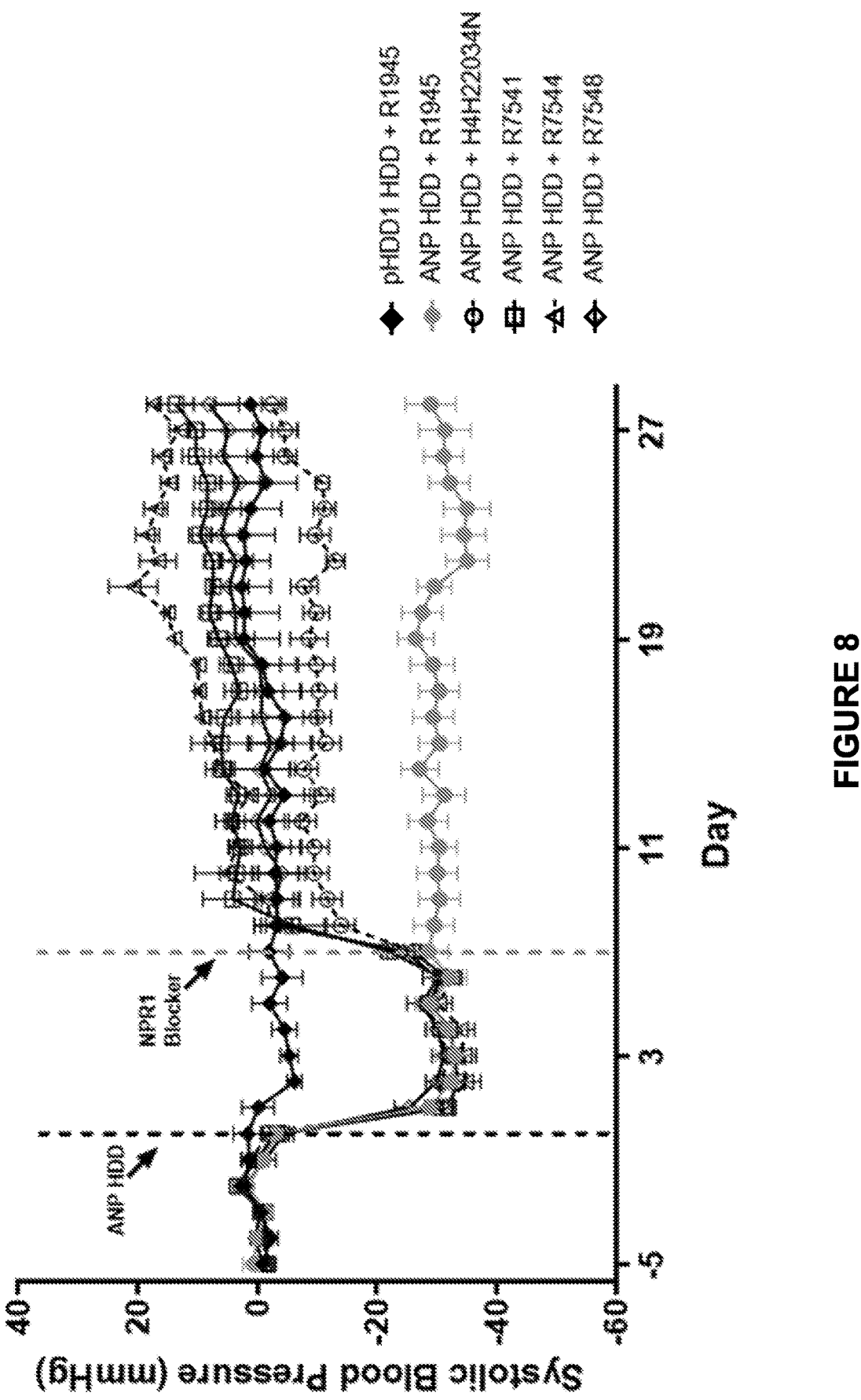
FIG. 8 shows the effects of NPR1 antagonist mAb's on systolic blood pressures in ANP overexpression-induced hypotensive NPR1$^{hu/hu}$ mice. Telemetered normotensive NPR1$^{hu/hu}$ mice were randomized into groups based on body weight. Animals were given a single 50 ug HDD dose of control or ANP plasmid followed by a single 25 mg/kg intravenous injection of NPR1 antagonist mAb or isotype control as described in Table 31. All values are mean±SEM, n=4-7 per group.

The in vivo characterization of NPR1 antagonist antibodies demonstrated that when compared to IgG4P isotype control-dosed animals, NPR1 antagonist antibodies were able to rapidly and persistently normalize the ANP overexpression-induced reductions of systemic blood pressure in NPR1$^{hu/hu}$ mice (Table 32 and Table 33). Serum NTproANP concentrations were significantly and persistently increased for the duration of the testing period (Table 34), indicating effective overexpression of ANP. The magnitude of blood pressure increase in ANP HDD-induced hypotensive mice following a single intravenous 25 mg/kg dose of an NPR1 blocker as assessed by mean (of days 7 to 28 post-dose) systolic blood pressure change from baseline ranged from −9.27±0.61 (H4H22034N) to +10.26±1.48 (REGN7544) mmHg (Table 33 and FIG. 8) relative to pre-ANP HDD dosing.

TABLE 32

7-day Post HDD Dose Mean Change from Baseline Blood Pressures and Heart Rates

| HDD Group: | Test Article | Test Article Dose (mg/kg) | Systolic (mmHg) | Diastolic (mmHg) | Mean Arterial (mmHg) | Pulse Pressure (mmHg) | Heart Rate (BPM) |
|---|---|---|---|---|---|---|---|
| Control plasmid | Isotype control mAb | 25 | −2.83 ± 0.94 | −0.79 ± 0.88 | −1.75 ± 0.84 | −2.05 ± 0.43 | 0.36 ± 6.65 |
| ANP plasmid | | | −27.31 ± 3.53**** | −14.21 ± 1.75**** | −21.65 ± 2.72**** | −13.00 ± 1.82**** | 29.90 ± 11.10*** |
| | H4H22034N | | −26.27 ± 3.57**** | −12.94 ± 1.74**** | −20.13 ± 2.69**** | −13.23 ± 1.86**** | 32.31 ± 14.17*** |
| | REGN7541 | | −26.92 ± 3.58**** | −13.92 ± 1.84**** | −20.70 ± 2.77**** | −12.96 ± 1.78**** | 21.84 ± 10.08* |
| | REGN7544 | | −28.18 ± 3.73**** | −14.57 ± 1.79**** | −21.99 ± 2.80**** | −13.62 ± 2.04**** | 18.67 ± 17.90 |
| | REGN7548 | | −25.40 ± 3.12**** | −12.65 ± 1.44**** | −19.72 ± 2.35**** | −12.70 ± 1.72**** | 27.46 ± 11.94** |

Telemetered normotensive NPR1$^{hu/hu}$ mice were randomized into groups based on body weight. Animals were given a single 50 ug HDD dose of control or ANP plasmid followed by a single 25 mg/kg intravenous injection of NPR1 antagonist mAb or isotype control as described in Table 31. All values are mean ± SEM, n = 4-7 per group. Statistics - two way ANOVA with Dunnett's; *p < .05 vs. Control Plasmid (pHDD1) + Isotype control.

TABLE 33

8 through 28-day Post HDD Dose Mean Change from Baseline Blood Pressures and Heart Rates

| HDD Group: | Test Article | Test Article Dose (mg/kg) | Systolic (mmHg) | Diastolic (mmHg) | Mean Arterial (mmHg) | Pulse Pressure (mmHg) | Heart Rate (BPM) |
|---|---|---|---|---|---|---|---|
| Control plasmid | Isotype control mAb | 25 | −0.93 ± 0.53**** | 0.81 ± 0.46**** | −0.18 ± 0.47**** | −1.75 ± 0.22**** | −14.04 ± 1.86**** |
| ANP plasmid | | | −30.40 ± 0.51 | −15.68 ± 0.41 | −23.77 ± 0.45 | −14.64 ± 0.18 | 10.49 ± 1.77 |
| | H4H22034N | | −9.27 ± 0.61**** | −6.21 ± 0.61**** | −7.67 ± 0.57**** | −3.04 ± 0.24**** | −23.86 ± 2.40**** |
| | REGN7541 | | 6.02 ± 0.85**** | 0.43 ± 0.54**** | 3.25 ± 0.64**** | 5.59 ± 0.54**** | −51.16 ± 3.86**** |
| | REGN7544 | | 10.26 ± 1.48**** | 2.95 ± 0.87**** | 6.45 ± 1.12**** | 7.32 ± 0.72**** | −65.29 ± 5.12**** |
| | REGN7548 | | 1.44 ± 0.80**** | −1.29 ± 0.65**** | 0.07 ± 0.67**** | 2.73 ± 0.21**** | −41.61 ± 2.57**** |

Telemetered normotensive NPR1$^{hu/hu}$ mice were randomized into groups based on body weight. Animals were given a single 50 ug HDD dose of control or ANP plasmid followed by a single 25 mg/kg intravenous injection of NPR1 antagonist mAb or isotype control as described in Table 31. All values are mean ± SEM, n = 4-7 per group. Statistics - two way ANOVA with Dunnett's; *p < .05 vs. Control Plasmid (pHDD1) + Isotype control.

TABLE 34

Days 14, 21 and 28 Serum NTproANP Concentrations

| HDD Group: | Test Article | Test Article Dose (mg/kg) | Serum NTproANP Concentrations (nMol/L) | | |
|---|---|---|---|---|---|
| | | | Day 14 | Day 21 | Day 28 |
| Control plasmid | Isotype control mAb | 25 | 0.61 ± 0.07 | 0.85 ± 0.15 | 0.49 ± 0.08 |
| ANP plasmid | | | 5.21 ± 1.00**** | 5.54 ± 0.55**** | 5.45 ± 0.96**** |
| | H4H22034N | | 4.74 ± 0.62*** | 4.76 ± 0.61*** | 4.71 ± 0.56*** |
| | REGN7541 | | 5.51 ± 0.84**** | 5.26 ± 0.85*** | 4.96 ± 0.87*** |
| | REGN7544 | | 6.88 ± 0.41**** | 5.58 ± 0.77*** | 6.40 ± 0.42**** |
| | REGN7548 | | 6.07 ± 0.29**** | 5.44 ± 0.88**** | 5.78 ± 0.21**** |

Telemetered normotensive NPR1$^{hu/hu}$ mice were randomized into groups based on body weight. Animals were given a single 50 ug HDD dose of control orANP plasmid followed by a single 25 mg/kg intravenous injection of NPR1 antagonist mAb or isotype control as described in Table 31.
All values are mean + SEM, n = 5-8 per group. Statistics - two way ANOVA with Dunnett's;
*p < .05 vs. Control plasmid (pHDD1) + Isotype control.

Figures 9A, 9B:
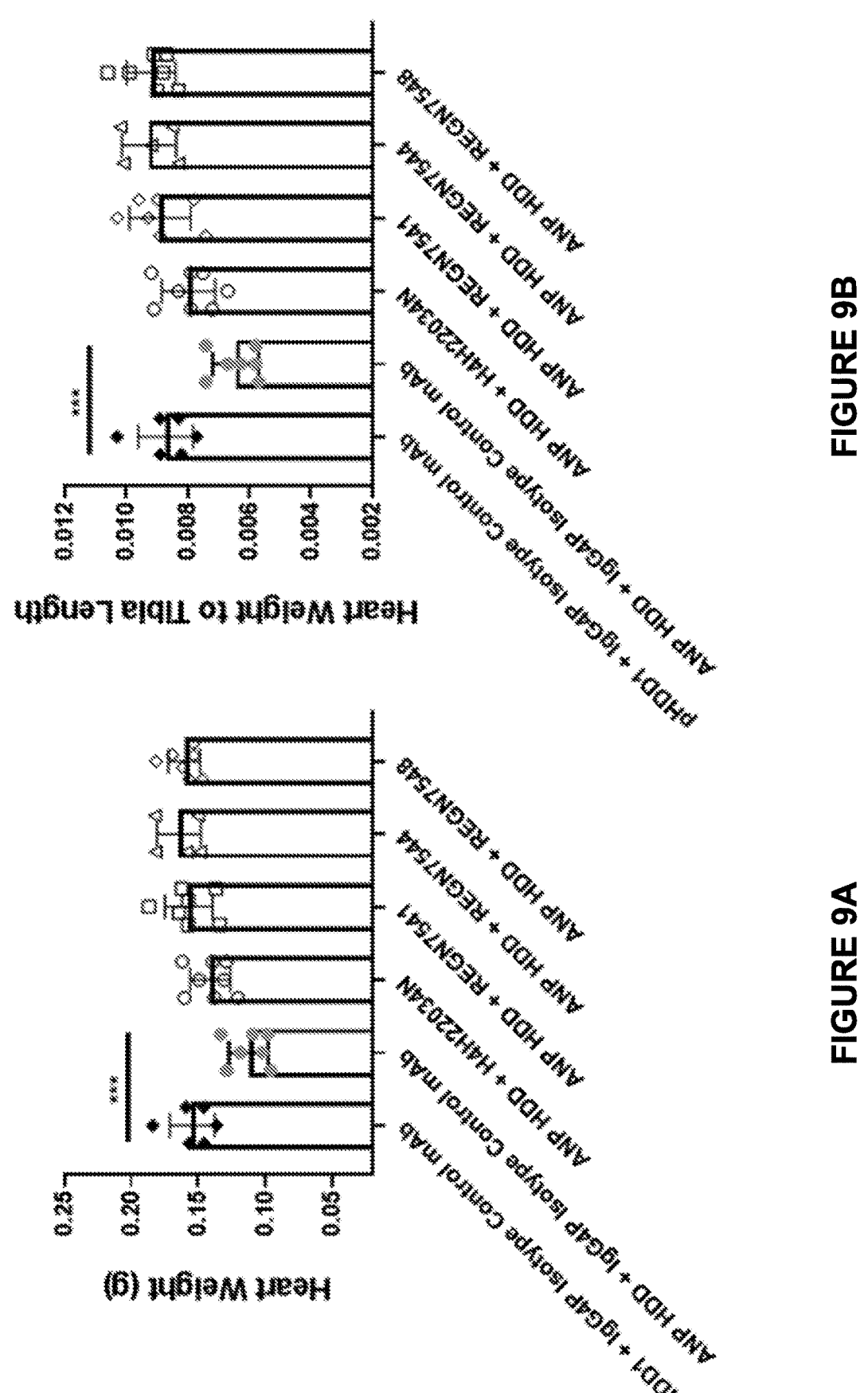
FIGS. 9A and 9B show the effects of NPR1 antagonist mAb's on absolute (FIG. 9A) and relative heart weight (FIG. 9B) following overexpression-induced hypotensive NPR1$^{hu/hu}$ mice. Telemetered normotensive NPR1$^{hu/hu}$ mice were randomized into groups based on body weight. Animals were given a single 25 mg/kg subcutaneous injection of an NPR1 antagonist mAb or IgG4P isotype control mAb as described in Table 31. All values are mean±SEM, n=5-8 per group.

Consistent with the significant and persistent reductions of systemic pressures and likely reductions of left ventricular afterload, absolute and relative heart weights were significantly reduced in mice that had received ANP HDD (FIGS. 9A and 9B). Hearts of animals that received an NPR1 blocking mAb were not different than normotensive controls and indicate an effective increase in systemic and ventricular pressures.

NPR1 antagonist antibodies H4H22034N, REGN7541, REGN7544 and REGN7548 significantly and persistently increased systemic blood pressures for up to 28 days in ANP HDD-induced hypotensive NPR1$^{hu/hu}$ mice.

Example 11: NPR1 Blockade in Preventative and Therapeutic Dosing with LPS Induced Shock Model in Telemetered NPR1$^{hu/Hu}$ Mice Experimental Procedure The objectives of this study were to assess the effects of NPR1 antagonist antibodies dosed preventatively or therapeutically to telemetered NPR1$^{hu/hu}$ mice that had hypotension resulting from the administration of LPS. Male NPR1$^{hu/hu}$ (n=58) mice aged ~12-17 weeks were implanted with PA-C10 telemeters (DSI, St. Paul, MN) and allowed to recover for at least 7 days. Animals were stratified into groups (Groups 1-6) based on body weight and systolic and pulse pressures, prior to being assigned to group (Table 35). Animals were individually housed under standard conditions (Temperatures of 64° F. to 84° F. (18° C. to 29° C.); relative humidity of 30% to 70%) and a 12-hour light/12-hour dark cycle was maintained. Food (Research Diets Standard pellet chow) and water were provided ad libitum.

TABLE 35

Summary of Doses and Dose Groups

| Group No. | Number of Animals Males | Challenge | Test or Control Article | Dose Level (mg/kg/ i.v.) | Dose Volume (mL/kg) |
|---|---|---|---|---|---|
| 1 | 8 | Saline | PBS | 0 | 5 |
| 2 | 10 | LPS | | | |
| 3 | 10 | (5 mg/kg, | REGN7544 | 25 | |
| 4 | 10 | i.p.) | REGN7548 | | |

TABLE 35-continued

Summary of Doses and Dose Groups

| Group No. | Number of Animals Males | Challenge | Test or Control Article | Dose Level (mg/kg/ i.v.) | Dose Volume (mL/kg) |
|---|---|---|---|---|---|
| 5 | 10 | | * Preventative* - REGN7544 | | |
| 6 | 10 | | * Preventative* - REGN7548 | | |

Animals were administered a single intraperitoneal injection of 5 mg/kg LPS or PBS on day 0. The test proteins were administered to the appropriate animals by single intravenous injection ~24 hours pre- or 8 hours post-LPS dose. The dose volume for each animal was based on the most recent body weight measurement.

Systolic pressure, diastolic pressure, mean arterial pressure, pulse pressure and heart rate were collected for 10 seconds every 10 minutes for the duration of the testing period. Telemetry data are presented as mean 24-hour values. All data are presented as mean±SEM.

Results

Figure 10:
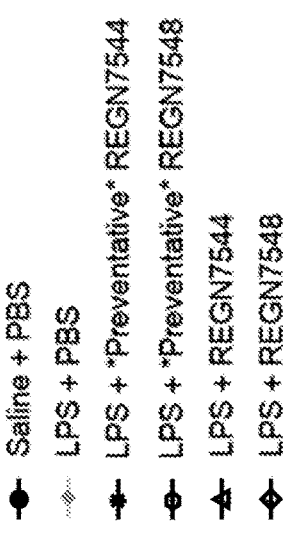
FIG. 10 shows the effects of NPR1 antagonist mAb's on pulse pressures in LPS-induced hypotensive NPR1$^{hu/hu}$ mice-single 25 mg/kg preventative or therapeutic intravenous dose. Telemetered NPR1$^{hu/hu}$ mice were randomized into groups based on body weight. Animals were given a single 5 mg/kg intraperitoneal injection of LPS or saline and a single intravenous injection of an NPR1 antagonist mAb or PBS ~24 hours pre- or 8 hours post-LPS dose as described in Table 35. All values are mean±SEM, n=7-10 per group.
Figure 10:
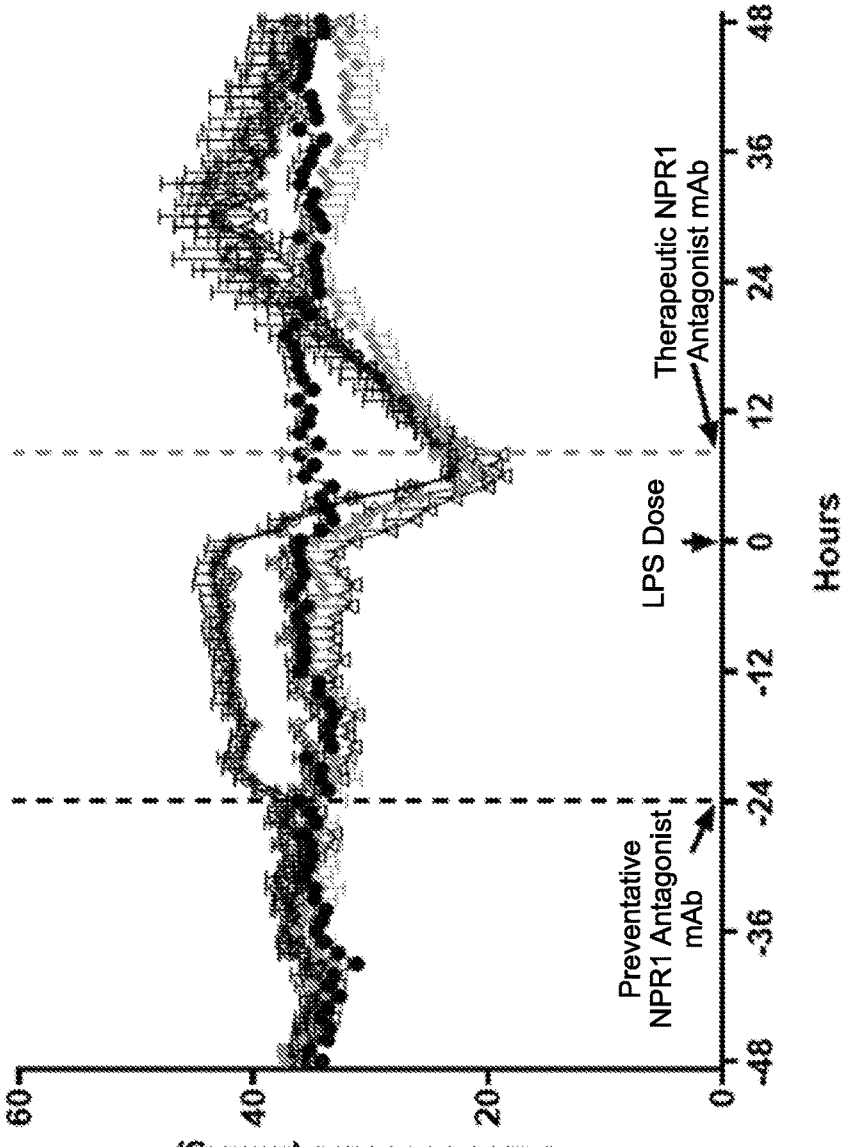

The in vivo characterization of NPR1 antagonist antibodies dosed preventatively or therapeutically to LPS-induced hypotensive NPR1$^{hu/hu}$ mice showed significant and persistent increases of systemic blood pressure (Table 36, Table 37, FIG. 10). Animals dosed preventatively presented with rapid increases of pressure (Table 36). The magnitude of blood pressure increase in the preventative arm of the study following a single intravenous 25 mg/kg dose as assessed by mean (of 24 hours prior to through time of LPS dose) systolic blood pressure change from baseline ranged from +7.24±1.18 (REGN7548) to +9.07±1.10 (REGN7541) mmHg (Table 36 and FIG. 10). The magnitude of blood pressure increase following a single intravenous 25 mg/kg dose administered 8 hours after LPS dosing as assessed by mean (of 8 hours to 48 hours post-LPS dose) systolic blood pressure change from baseline ranged from −1.49±2.244 (REGN7548) to −1.49±2.24 (REGN7544) mmHg (Table 37). Pulse pressures in therapeutically dosed animals as assessed by mean (of 8 hours to 48 hours post-LPS dose) pulse pressured pressure change from baseline ranged from 0.27±0.93 (REGN7548) to −0.40±0.91 (REGN7544) mmHg (Table 37, FIG. 10).

TABLE 36

24-hour pre to time 0 prior to LPS Dose Mean Change from Baseline Blood Pressures and Heart Rates

| Challenge | Dose Group: | Dose (mg/kg) | Systolic (mmHg) | Diastolic (mmHg) | Mean Arterial (mmHg) | Pulse Pressure (mmHg) | Heart Rate (BPM) |
|---|---|---|---|---|---|---|---|
| Saline | PBS | 0 | 0.14 ± 1.2 | −0.13 ± 1.02 | 0.03 ± 1.10 | 0.30 ± 0.23*** | 1.85 ± 8.06 |
| LPS | PBS | | −0.90 ± 1.2 | 0.26 ± 1.06 | −0.37 ± 1.15 | −1.13 ± 0.19 | 4.89 ± 7.91 |
| LPS | *Preventative* - REGN7544 | 25 | 9.07 ± 1.10**** | 3.49 ± 0.96*** | 6.65 ± 0.99**** | 5.60 ± 0.32**** | −2.57 ± 5.84 |
| LPS | *Preventative* - REGN7548 | | 7.24 ± 1.18**** | 1.93 ± 1.08 | 4.93 ± 1.09**** | 5.30 ± 0.24**** | −2.93 ± 5.31 |
| LPS | REGN7544 | | −0.04 ± 1.36 | 2.46 ± 1.28 | 1.08 ± 1.31 | −2.55 ± 0.20** | −0.57 ± 8.27 |
| LPS | REGN7548 | | −0.44 ± 1.26 | −0.49 ± 1.11 | −0.41 ± 1.18 | 0.05 ± 0.18**** | 2.85 ± 8.05 |

Telemetered NPR1$^{hu/hu}$ mice were randomized into groups based on body weight. Animals were given a single 5 mg/kg intraperitoneal injection of LPS or saline and a single intravenous injection of an NPR1 antagonist mAb or PBS ~24 hours pre- or 8 hours post-LPS dose as described in Table 35. All values are mean ± SEM, n = 7-10 per group. Statistics - two way ANOVA with Dunnett's; *p < .05 vs. LPS + PBS.

TABLE 37

| | | Dose | Systolic | Diastolic | Mean Arterial | Pulse Pressure | Heart Rate |
|---|---|---|---|---|---|---|---|
| Challenge | Dose Group: | (mg/kg) | (mmHg) | (mmHg) | (mmHg) | (mmHg) | (BPM) |
| Saline | PBS | 0 | 0.66 ± 0.68**** | 0.10 ± 0.69**** | −0.15 ± 0.71**** | 0.56 ± 0.13**** | −41.12 ± 6.54**** |
| LPS | PBS | | −7.52 ± 1.75 | −3.33 ± 1.34 | −5.77 ± 1.48 | −4.19 ± 0.54 | −10.32 ± 5.50 |
| LPS | *Preventative* - REGN7544 | 25 | −3.32 ± 2.28** | −3.41 ± 1.69 | −3.88 ± 1.93 | 0.24 ± 0.85**** | −39.73 ± 3.84**** |
| LPS | *Preventative* - REGN7548 | | −6.13 ± 2.19 | −5.10 ± 1.48 | −5.84 ± 1.76 | −1.03 ± 0.95**** | −4.37 ± 5.63 |
| LPS | REGN7544 | | −1.49 ± 2.46**** | −1.92 ± 1.71 | −1.57 ± 2.03*** | −0.40 ± 0.91**** | −66.59 ± 9.70**** |
| LPS | REGN7548 | | −1.49 ± 2.24**** | −1.50 ± 1.60 | −1.63 ± 1.85** | 0.27 ± 0.93**** | −69.46 ± 8.02**** |

8- to 48-hour Post LPS Dose Mean Change from Baseline Blood Pressures and Heart Rates Telemetered NPR1$^{hu/hu}$ mice were randomized into groups based on body weight. Animals were given a single 5 mg/kg intraperitoneal injection of LPS or saline and a single intravenous injection of an NPR1 antagonist mAb or PBS ~24 hours pre- or 8 hours post-LPS dose as described in Table 35. All values are mean ± SEM, n = 7-10 per group. Statistics - two way ANOVA with Dunnett's; *p < .05 vs. LPS + PBS.

NPR1 antagonist antibodies REGN7544 and REGN7548 significantly and persistently increased systemic blood pressures when administered preventatively or therapeutically to mice that developed LPS-induced hypotension following a single intraperitoneal dose of LPS.

Example 12: Each NPR1 Monomer Binds One REGN7544 Fab

Experimental Procedure

Complex formation of NPR1+REGN7544 Fab+ANP

Human NPR1 extracellular domain with a C-terminal myc-myc-6×His tag (hNPR1-mmh; SEQ ID NO: 74) was mixed with Atrial Natriuretic factor (ANP, Tocris) and REGN7544 Fab in a molar ratio of 1 hNPR1-mmh+2 ANP+1 REGN7544 Fab. The complex was incubated overnight at 4° C. then purified over a Superdex 200 increase 10/300 GL gel filtration column equilibrated with 50 mM Tris pH 7.5, 150 mM NaCl. Peak fractions were collected and concentrated and concentrated using a 10 kDa MWCO centrifugal concentrator (Amicon).

Cryo EM Grid Preparation and Data Collection

The NPR1-ANP-REGN7544 complex was diluted to 0.87 mg/ml, and Poly (Maleic Anhydride-alt-1-Decene) substituted with 3-(Dimethylamino) Propylamine (PMAL-C8; Anatrace Cat. #P5008) was added to 0.15% final concentration. The sample was deposited onto a freshly plasma cleaned UltrAufoil grid (Quantifoil GmbH). Excess solution was blotted away with filter paper and plunge frozen into liquid ethane using a Vitrobot Mark IV (Thermo Fisher Part #1086439). The grid was loaded into a Titan Krios G3i (Thermo Fisher, Part #1137337) equipped with a Bioquantum energy filter+K3 direct electron detector (Gatan Inc, Part #1147213). Movies were collected using EPU v 2.7 (Thermo Fisher) at 105,000× magnification, corresponding to a pixel size of 0.86 Å. A dose rate of 15 electrons per pixel per second was used, and each movie was 2 seconds and 46 frames, corresponding to a total dose of ~40 electrons per Å2.

Cryo-EM Data Processing

All cryo-EM data processing was carried out using cryoSPARC v3.2.0 (Structura Biotechnology Inc.). The movies were aligned using patch motion correction and patch CTF estimation. A total of 6692 movies were collected and then 6474 movies selected after motion correction and patch CTF. An initial set of particles picked using blob picker were subjected to 2D classification to generate templates for template picking. ~1.6 million particles picked by template picking were subjected to multiple rounds of 2D classification, resulting in 814,655 'good' complex particles. Ab initio reconstruction with 6 classes followed by heterogeneous refinement generated one "good" class containing 310,944 particles that corresponded to the full NPR1-ANP-REGN7544 Fab in an isotropic map. Non-uniform refinement of the particles in the "good" class was followed by local refinement resulted in a 3.15 Å resolution (FSC=0.143) map that was used for model building. Into this map, we manually placed models of the NPR1 (taken from PDB code 1T34) and the two Fabs (taken from prior Regeneron antibody structures). These models were then manually rebuilt using Coot (v 0.8.2 Medical Research Council Laboratory of Molecular Biology) and real space refined against the map using Phenix (v 1.15.2 The PHENIX Industrial Consortium).

Complex Formation of NPR1+REGN7544 Fab

Human NPR1 extracellular domain with a C-terminal myc-myc-6×His tag (hNPR1-mmh; SEQ ID NO: 74) was mixed with the REGN7544 Fab in a molar ratio of 1 hNPR1-mmh+1 REGN7544 Fab. The complex was incubated overnight at 4° C., then purified over a Superdex 200 increase 10/300 GL gel filtration column equilibrated with 50 mM Tris pH 7.5, 150 mM NaCl. Peak fractions were collected and concentrated and concentrated using a 10 kDa MWCO centrifugal concentrator (Amicon).

Cryo EM Grid Preparation and Data Collection

The NPR1-REGN7544 complex was diluted to 0.8 mg/ml, and Poly (Maleic Anhydride-alt-1-Decene) substituted with 3-(Dimethylamino) Propylamine (PMAL-C8; Anatrace Cat. #P5008) was added to 0.15% final concentration. The sample was deposited onto a freshly plasma cleaned UltrAufoil grid (Quantifoil GmbH). Excess solution was blotted away with filter paper and plunge frozen into liquid ethane using a Vitrobot Mark IV (Thermo Fisher Part #1086439). The grid was loaded into a Titan Krios G3i (Thermo Fisher, Part #1137337) equipped with a Bioquantum energy filter+K3 direct electron detector (Gatan Inc, Part #1147213). Movies were collected using EPU v 2.7 (Thermo Fisher) at 105,000× magnification, corresponding to a pixel size of 0.86 Å. A dose rate of 15 electrons per pixel per second was used, and each movie was 2 seconds and 46 frames, corresponding to a total dose of ~40 electrons per Å2.

Cryo-EM Data Processing

All cryo-EM data processing was carried out using cryoSPARC v3.2.0 (Structura Biotechnology Inc.). The movies were aligned using patch motion correction and patch CTF estimation. A total of 10,378 movies were collected and then 9660 movies selected after motion correction and patch CTF. An initial set of particles picked using blob picker were subjected to 2D classification to generate templates for template picking. ~1.7 million particles picked by template picking were subjected to multiple rounds of 2D classification, resulting in 762,681 'good' complex particles. Ab initio reconstruction with 6 classes followed by heterogeneous refinement generated one "good" class containing 256,375 particles that corresponded to the full NPR1-REGN7544 Fab in an isotropic map. Non-uniform refinement of the particles in the "good" class was followed by local refinement resulted in a 3.42 Å resolution (FSC=0.143) map that was used for model building. Into this map, models of the NPR1 (taken from PDB code 1DP4) and the two Fabs (taken from prior Regeneron antibody structures) were manually Leu144, Glu384, Leu401, Val402, Ala103, Ser405, Gly406, Arg407, Lys408, Trp411, Leu413, Gly414, Tyr415, and Pro416.

Example 13: Assessment of the Ability of Vasodilators to Reverse REGN7544-Induced Changes in Blood Pressure The ability of three different vasodilatory agents (Nifedipine (Sigma-Aldrich), Enalapril (Sigma-Aldrich), and Molsidomine (Sigma-Aldrich)) with different mechanistic targets to reverse REGN7544-induced increase in blood pressure was evaluated in NPR1-humanized mice. Enalapril, Molsidomine, and Nifedipine, the three vasodilatory agents used, were administered orally. Enalapril lowers blood pressure by inhibition of angiotensin-converting enzyme (ACE), which lowers blood pressure by decreasing the production of angiotensin II, a vasoconstrictor, and increasing levels of bradykinin, a peptide that increases the diameter of blood vessels. Molsidomine, a nitric oxide donor, and nifedipine, a calcium channel blocker, also lower blood pressure.

The dosing scheme for evaluating the reversal of REGN7544-induced effects by vasodilators in telemetered NPR1-humanized mice is summarized in the following table:

TABLE 38

| Dose Groups | | | | | | | |
|---|---|---|---|---|---|---|---|
| Dosing on Day 0 | | Daily Dosing Days 7-13 | | | | | |
| | Dose | | | Dose | | Mice Used | |
| Test Article | Administered (SC) | | Test Article | Administered (Oral Gavage) | n | Age (Weeks) | Duration of Study |
| PBS | 5 mL/kg | | Water | 10 mL/kg | 6 | 13 to 15 | 13 days |
| REGN7544 | 25 mg/kg | | Water | 10 mL/kg | 6 | | |
| | | | Nifedipine | 20 mg/kg | 6 | | |
| | | | Enalapril | 25 mg/kg | 7 | | |
| | | | Molsidomine | 10 mg/kg | 7 | | |

PBS, phosphate-buffered saline;
SC, subcutaneous placed. These models were then manually rebuilt using Coot (v 0.8.2 Medical Research Council Laboratory of Molecular Biology) and real space refined against the map using Phenix (v 1.15.2 The PHENIX Industrial Consortium).

Results

The structures of hNPR1+ANP+REGN7544 Fab and hNPR1+REGN7544 Fab showed that each NPR1 monomer binds one REGN7544 Fab. The Fab binds to residues in the lower (C-terminal, closer to the cell membrane) lobe of the extracellular domain. With REGN7544 bound, the NPR1 dimer adopts an inactive conformation in the absence of ANP, and an active conformation in the presence of ANP. These conformations are very similar to the observed states of NPR1 with no antibody bound in the presence or absence of ANP; however, these studies were done with soluble extracellular domains, not the full membrane-bound form of NPR1. Both heavy and light chain of REGN7544 interact with the NPR1 extracellular domain. Contact residues in the NPR1 extracellular domain remain the same either in the presence or absence of ANP. There are 15 contact residues through the heavy chain and 7 contact residues through the light chain. The residues in the NPR1 extracellular domain directly interacting with the REGN7544 Fab are Arg143, Male telemetered NPR1-humanized mice ages 13 to 15 weeks were administered a single dose of 25 mg/kg REGN7544 (n=28) or vehicle control (i.e., PBS) (n=7) via subcutaneous (SC) injection on Day 0. Beginning on Day 7 (169 hours post SC dosing), mice pretreated with REGN7544 began receiving daily doses of nifedipine (20 mg/kg), enalapril (25 mg/kg), molsidomine (10 mg/kg), or water (n=7/group) via oral gavage (PO), while all mice pretreated with vehicle control received water. Diastolic and systolic blood pressure was recorded for all animals continuously 72 hours prior to administration of REGN7544 or vehicle control through the end of the experiment, and these measurements were used to calculate pulse pressure. Mean change in pulse pressure normalized to baseline for each treatment group was measured i) between 149 and 221 hours after administration of REGN7544 or vehicle control and ii) between 3 days prior to administration of REGN7544 or vehicle control through the end of the experiment.

Figure 11:
FIG. 11 shows the mean change in pulse pressure normalized to baseline for each treatment group between 3 days prior to administration of REGN7544 or vehicle control through the end of the experiment. Data are expressed as the group mean±standard error of the mean.

Each vasodilator tested lowered pulse pressure (PP) in NPR1-humanized mice pretreated with REGN7544 (FIG. 11). Indeed, the administration of vasodilators was shown to reverse pulse pressure-increasing effects of REGN7544.

Male telemetered NPR1-humanized mice ages 13 to 15 weeks were administered a single dose of 25 mg/kg REGN7544 (n=28) or vehicle control (i.e., PBS) (n=7) via subcutaneous (SC) injection on Day 0. Beginning on Day 7, mice pretreated with REGN7544 began receiving daily doses of nifedipine (20 mg/kg), enalapril (25 mg/kg), molsidomine (10 mg/kg), or water (n=7/group) via oral gavage (PO), while all mice pretreated with vehicle control received water. Pulse pressure was recorded for all animals continuously 72 hours prior to administration of REGN7544 or vehicle control through the end of the experiment. Mean change in systolic blood pressure normalized to baseline for each treatment group was measured between 3 days prior to administration of REGN7544 or vehicle control through the end of the experiment.

Figure 12:
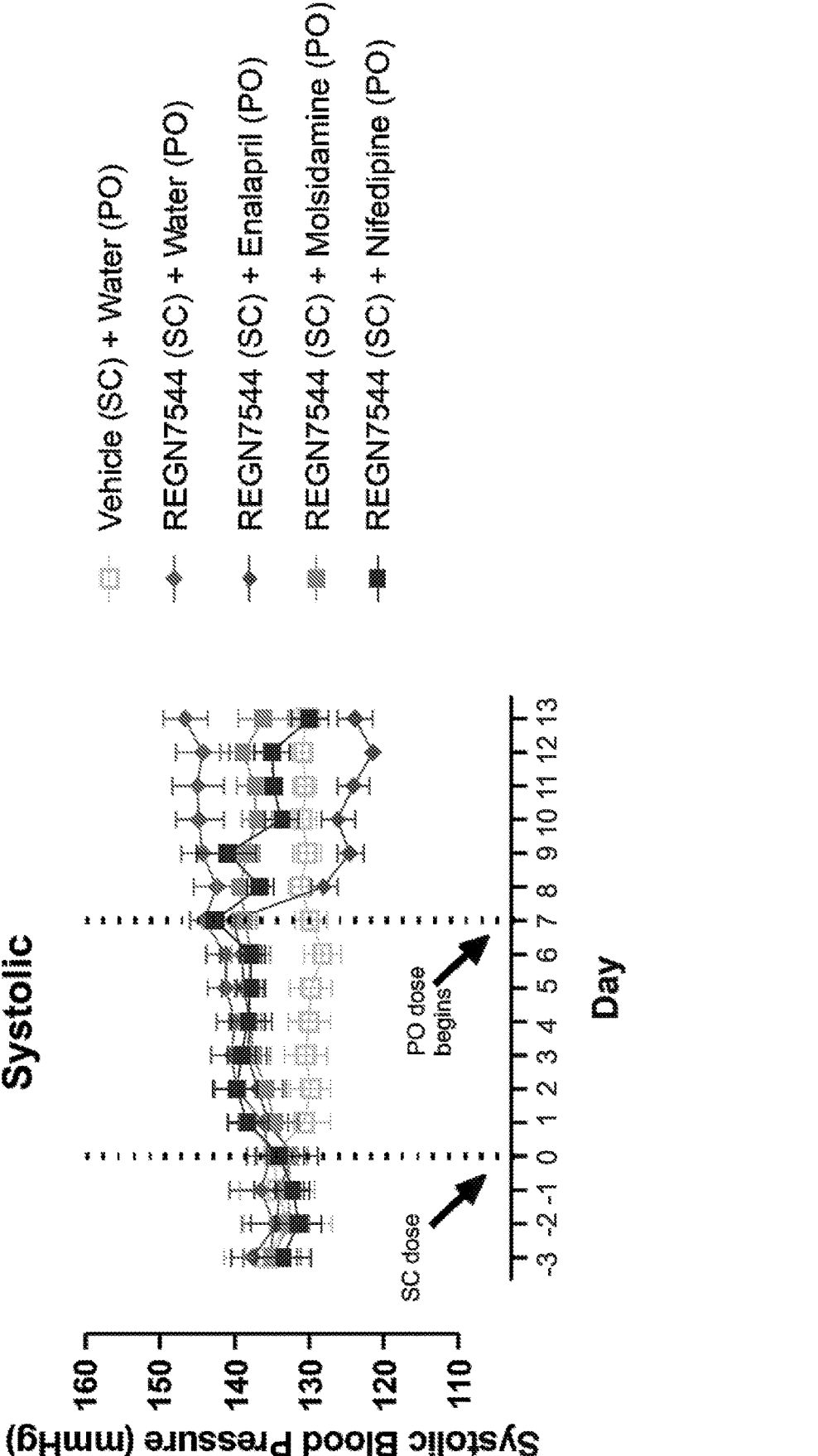
FIG. 12 shows the mean change in systolic blood pressure normalized to baseline for each treatment group between 3 days prior to administration of REGN7544 or vehicle control through the end of the experiment. Data are expressed as the group mean±standard error of the mean. Vertical stippled lines indicate administration of drug indicated by route of administration (i.e., SC or PO).

The vasodilators decreased systolic blood pressure (SBP) in NPR1-humanized mice pretreated with REGN7544 (FIG. 12). Indeed, the administration of vasodilators was found to reverse REGN7544-induced increase in systolic blood pressure.

Male telemetered NPR1-humanized mice ages 13 to 15 weeks were administered a single dose of 25 mg/kg REGN7544 (n=28) or vehicle control (i.e., PBS) (n=7) via subcutaneous (SC) injection on Day 0. Beginning on Day 7, mice pretreated with REGN7544 began receiving daily doses of nifedipine (20 mg/kg), enalapril (25 mg/kg), molsidomine (10 mg/kg), or water (n=7/group) via oral gavage (PO), while all mice pretreated with vehicle control received water. Pulse pressure was recorded for all animals continuously 72 hours prior to administration of REGN7544 or vehicle control through the end of the experiment. Mean change in heart rate normalized to baseline for each treatment group was measured between 3 days prior to administration of REGN7544 or vehicle control through the end of the experiment.

No observable effect on heart rate following administration of enalapril, molsidomine, and nifedipine was recorded (data not shown). Indeed, the administration of vasodilators in the presence of REGN7544 was shown to have no effect on heart rate.

Male telemetered NPR1-humanized mice ages 13 to 15 weeks were administered a single dose of 25 mg/kg REGN7544 (n=28) or vehicle control (i.e., PBS) (n=7) via subcutaneous (SC) injection on Day 0. Beginning on Day 7, mice pretreated with REGN7544 began receiving daily doses of nifedipine (20 mg/kg), enalapril (25 mg/kg), molsidomine (10 mg/kg), or water (n=7/group) via oral gavage (PO), while all mice pretreated with vehicle control received water. Systolic and diastolic blood pressure was recorded for all animals continuously 72 hours prior to administration of REGN7544 or vehicle control through the end of the experiment, and these measurements were used to calculate pulse pressure. Mean pulse pressure for each treatment group was measured between 3 days prior to administration of REGN7544 or vehicle control through the end of the experiment. The administration of vasodilators reversed pulse pressure-increasing effects of a single SC dose of REGN7544 (data not shown).

Male telemetered NPR1-humanized mice ages 13 to 15 weeks were administered a single dose of 25 mg/kg REGN7544 (n=28) or vehicle control (i.e., PBS) (n=7) via subcutaneous (SC) injection on Day 0. Beginning on Day 7, mice pretreated with REGN7544 began receiving daily doses of nifedipine (20 mg/kg), enalapril (25 mg/kg), molsidomine (10 mg/kg), or water (n=7/group) via oral gavage (PO), while all mice pretreated with vehicle control received water. Systolic blood pressure was recorded for all animals continuously 72 hours prior to administration of REGN7544 or vehicle control through the end of the experiment. Mean systolic blood pressure for each treatment group was measured between 3 days prior to administration of REGN7544 or vehicle control through the end of the experiment. The administration of vasodilators reverses systolic blood pressure-increasing effects of a single SC dose of REGN7544 (data not shown).

Male telemetered NPR1-humanized mice ages 13 to 15 weeks were administered a single dose of 25 mg/kg REGN7544 (n=28) or vehicle control (i.e., PBS) (n=7) via subcutaneous (SC) injection on Day 0. Beginning on Day 7, mice pretreated with REGN7544 began receiving daily doses of nifedipine (20 mg/kg), enalapril (25 mg/kg), molsidomine (10 mg/kg), or water (n=7/group) via oral gavage (PO), while all mice pretreated with vehicle control received water. Heart rate was recorded for all animals continuously 72 hours prior to administration of REGN7544 or vehicle control through the end of the experiment. Mean heart rate for each treatment group was measured between 3 days prior to administration of REGN7544 or vehicle control through the end of the experiment. The administration of vasodilators following a single dose of REGN7544 had no compensatory effect on heart rate (data not shown).

Male telemetered NPR1-humanized mice ages 13 to 15 weeks were administered a single dose of 25 mg/kg REGN7544 (n=28) or vehicle control (i.e., PBS) (n=7) via subcutaneous (SC) injection on Day 0. Beginning on Day 7, mice pretreated with REGN7544 began receiving daily doses of nifedipine (20 mg/kg), enalapril (25 mg/kg), molsidomine (10 mg/kg), or water (n=7/group) via oral gavage (PO), while all mice pretreated with vehicle control received water. Diastolic blood pressure was recorded for all animals continuously 72 hours prior to administration of REGN7544 or vehicle control through the end of the experiment. Mean diastolic blood pressure (i) normalized to baseline and (ii) non-normalized for each treatment group was measured between 3 days prior to administration of REGN7544 or vehicle control through the end of the experiment. The administration of enalapril reversed diastolic blood pressure-increasing effects of a single SC dose of REGN7544 (data not shown).

Thus, the reversibility of hemodynamic effects following SC dosing of 25 mg/kg REGN7544 was tested by oral gavage of 3 clinical vasodilators. The three different vasodilatory agents, nifedipine, enalapril, and molsidomine, each reversed the REGN7544-induced increase in PP while having no observable significant effect on heart rate. REGN7544-mediated increases in PP were separately reversed by any one of three clinical vasodilators (nifedipine, enalapril, and molsidomine) administered by oral gavage.

The present disclosure is not to be limited in scope by the specific embodiments described herein. Indeed, various modifications of the disclosure in addition to those described herein will become apparent to those skilled in the art from the foregoing description and the accompanying figures. Such modifications are intended to fall within the scope of the appended claims.

What is claimed is:

1. An isolated antibody or antigen-binding fragment thereof that binds specifically to natriuretic peptide receptor 1 (NPR1) protein, wherein the antibody or antigen-binding fragment thereof binds to NPR1 and blocks NPR1, wherein the antibody or antigen-binding fragment thereof comprises three heavy chain complementarity determining regions (CDRs), HCDR1, HCDR2, and HCDR3, contained within a heavy chain variable region (HCVR); and three light chain CDRs, LCDR1, LCDR2, and LCDR3, contained within a light chain variable region (LCVR), wherein the HCVR and LCVR pair comprises amino acid sequences, the amino acid sequences selected from the group consisting of SEQ ID NOs: 2 and 10, SEQ ID NOs: 22 and 30, SEQ ID NOs: 38 and 46, and SEQ ID NOs: 55 and 63, wherein the heavy chain region CDRs and light chain region CDRs are identified by Kabat, Chothia, or AbM.

2. The antibody or antigen-binding fragment thereof of claim 1, wherein the antibody is a fully human monoclonal antibody.

3. The antibody or antigen-binding fragment thereof of claim 1, wherein the antibody has one or more properties selected from the group consisting of: (a) is a fully human monoclonal antibody; (b) binds to human NPR1 at 25° C. and at 37° C. with a dissociation constant ($K_D$) of less than 1.7 nM, as measured in a surface plasmon resonance assay; (c) binds to monkey NPR1 at 25° C. and 37° C. with a $K_D$ of less than 1.99 nM, as measured in a surface plasmon resonance assay; (d) binds to human NPR1 in the presence of ANP at 25° C. and at 37° C. with a $K_D$ of less than 1.52 nM, as measured in a surface plasmon resonance assay; (e) inhibits ligand-induced NPR1 activation, as measured by cGMP accumulation assay; (f) binds to human NPR1 in the presence or absence of ANP or BNP with an $EC_{50}$ of less than 2.9 nM, as measured by electrochemiluminescence-based immunoassay; (g) binds to monkey NPR1 in the presence or absence of ANP or BNP with an $EC_{50}$ of less than 4.2 nM, as measured by electrochemiluminescence-based immunoassay; (h) increases the systemic blood pressures when administered to normotensive and hypotensive mice, wherein the increase in systemic blood pressures lasts for up to about 28 days upon administration of a single dose; (i) increases the systemic blood pressures when administered to ANP overexpression-induced hypotensive mice, wherein the increase in systemic blood pressures lasts for up to about 28 days upon administration of a single dose; and (j) increases systemic blood pressures in LPS-induced hypotensive mice.

4. The antibody or antigen-binding fragment thereof of claim 1, wherein the HCVR and LCVR amino acid sequence pair comprises: the amino acid sequences selected from the group consisting of SEQ ID NOs: 2 and 10, SEQ ID NOs: 22 and 30, SEQ ID NOs: 38 and 46, and SEQ ID NOs: 55 and 63.

5. The antibody or antigen-binding fragment of claim 1 comprising a heavy chain variable region (HCVR) and light chain variable region (LCVR) amino acid sequence pair selected from the group consisting of SEQ ID NOs: 2 and 10, SEQ ID NOs: 22 and 30, SEQ ID NOs: 38 and 46, and SEQ ID NOs: 55 and 63.

6. The antibody or antigen-binding fragment thereof of claim 1, wherein (a) the HCDR1, HCDR2, HCDR3, LCDR1, LCDR2, and LCDR3 domains comprise amino acid sequences of SEQ ID NOs: 4, 6, 8, 12, AAS, and SEQ ID NO: 16, respectively, wherein the HCVR and LCVR amino acid sequence comprises SEQ ID NOs: 2 and 10;

(b) the HCDR1, HCDR2, HCDR3, LCDR1, LCDR2, and LCDR3 domains comprise amino acid sequences of SEQ ID NOs: 24, 26, 28, 12, AAS, and SEQ ID NO: 32, respectively, wherein the HCVR and LCVR amino acid sequence comprises SEQ ID Nos: 22 and 30;

(c) the HCDR1, HCDR2, HCDR3, LCDR1, LCDR2, and LCDR3 domains comprise amino acid sequences of SEQ ID NOs: 40, 42, 44, 48, AAS, and SEQ ID NO: 16, respectively, wherein the HCVR and LCVR amino acid sequence comprises SEQ ID Nos: 38 and 46;

(d) the HCDR1, HCDR2, HCDR3, LCDR1, LCDR2, and LCDR3 domains comprise amino acid sequences of SEQ ID NOs: 57, 59, 61, 65, GAS, and SEQ ID NO: 69, respectively, wherein the HCVR and LCVR amino acid sequence comprises SEQ ID Nos: 55 and 63.

7. The antibody or antigen-binding fragment thereof of claim 1 comprising complementarity determining regions (CDRs) selected from the group consisting of: (a) SEQ ID NO: 4, SEQ ID NO: 6, SEQ ID NO: 8, SEQ ID NO: 12, AAS, and SEQ ID NO: 16; (b) SEQ ID NO: 24, SEQ ID NO: 26, SEQ ID NO: 28, SEQ ID NO: 12, AAS, and SEQ ID NO: 32; (c) SEQ ID NO: 40, SEQ ID NO: 42, SEQ ID NO: 44, SEQ ID NO: 48, AAS and SEQ ID NO: 16; and (d) SEQ ID NO: 57, SEQ ID NO: 59, SEQ ID NO: 61, SEQ ID NO: 65, GAS, and SEQ ID NO: 69.

8. The antibody or antigen-binding fragment thereof of claim 1, wherein the antibody or antigen-binding fragment thereof interacts with at least one of the NPR1 residues selected from the group consisting of Arg143, Leu144, Glu384, Leu401, Val402, Ala103, Ser405, Gly406, Arg407, Lys408, Trp411, Leu413, Gly414, Tyr415, and Pro416.

9. The antibody or antigen-binding fragment thereof of claim 1 comprising a heavy chain and a light chain, wherein the heavy chain comprises an amino acid sequence of SEQ ID NO: 18; and the light chain comprises an amino acid sequence of SEQ ID NO: 20.

10. The antibody or antigen-binding fragment thereof of claim 1 comprising a heavy chain and a light chain, wherein the heavy chain comprises an amino acid sequence of SEQ ID NO: 34; and the light chain comprises an amino acid sequence of SEQ ID NO: 36.

11. The antibody or antigen-binding fragment thereof of claim 1 comprising a heavy chain and a light chain, wherein the heavy chain comprises an amino acid sequence of SEQ ID NO: 51; and the light chain comprises an amino acid sequence of SEQ ID NO: 53.

12. The antibody or antigen-binding fragment thereof of claim 1 comprising a heavy chain and a light chain, wherein the heavy chain comprises an amino acid sequence of SEQ ID NO: 71; and the light chain comprises an amino acid sequence of SEQ ID NO: 73.

13. An antibody or antigen-binding fragment thereof that competes for binding to natriuretic peptide receptor 1 (NPR1) protein with the antibody or antigen-binding fragment thereof of claim 1.

14. An antibody or antigen-binding fragment thereof that binds to the same epitope as the antibody or antigen-binding fragment thereof of claim 1.

15. A pharmaceutical composition comprising the antibody or antigen-binding fragment thereof of claim 1 and a pharmaceutically acceptable carrier or diluent.

16. An isolated polynucleotide molecule comprising a polynucleotide sequence that encodes a heavy chain variable region (HCVR) and a light chain variable region (LCVR) of an antibody or antigen-binding fragment thereof as set forth in claim 1.

17. A vector comprising the polynucleotide molecule of claim 16.

18. A host cell expressing the vector of claim 17.

19. A method of producing an anti-NPR1 antibody or antigen-binding fragment thereof, comprising growing the host cell of claim 18 under conditions permitting production of the antibody or fragment, and recovering the antibody or fragment so produced.

20. The method of claim 19, further comprising formulating the antibody or antigen-binding fragment thereof as a pharmaceutical composition comprising an acceptable carrier.

21. A method of treating, preventing, or ameliorating at least one symptom or indication of a NPR1-associated disease or disorder, the method comprising administering a pharmaceutical composition comprising a therapeutically effective amount of the antibody or antigen-binding fragment thereof of claim 1 to a subject in need thereof.

22. The method of claim 21, wherein the NPR1-associated disease or disorder is selected from the group consisting of hypotension, circulatory shock, septic shock, neurogenic orthostatic hypotension, postural orthostatic tachycardia syndrome (POTS), heart failure, cardiogenic shock, obesity, renal failure, chronic kidney disease, macular edema, glaucoma, stroke, lung disorders, pulmonary fibrosis, inflammation, asthma, skeletal growth disorders, bone fractures, diabetes, hypoglycemia, and cancer.

23. The method of claim 21, wherein the pharmaceutical composition is administered prophylactically or therapeutically to the subject in need thereof.

24. The method of claim 21, wherein the pharmaceutical composition is administered in combination with a second therapeutic agent or therapy.

25. The method of claim 24, wherein the second therapeutic agent or therapy is selected from the group consisting of an angiogenesis inhibitor, a vasoconstrictor/vasopressor, an immunosuppressant, ascorbic acid, a calcineurin inhibitor, a corticosteroid, a VEGF inhibitor, a decongestant, an antidepressant, hormonal birth control, a stimulant, caffeine, extracorporeal membrane oxygenation, ventricular assist device, intra-aortic balloon pump, a lifestyle modification, a dietary supplement, an anti-microbial drug, insulin, and an anti-inflammatory drug.

26. The method of claim 21, wherein the pharmaceutical composition is administered subcutaneously, intravenously, intradermally, intraperitoneally, or intramuscularly.

27. An isolated antibody or antigen-binding fragment thereof that binds specifically to natriuretic peptide receptor 1 (NPR1) protein, wherein the antibody or antigen-binding fragment thereof binds to NPR1 and blocks NPR1, wherein the antibody or antigen-binding fragment thereof comprises three heavy chain complementarity determining regions (CDRs), HCDR1, HCDR2, and HCDR3 contained within a heavy chain variable region (HCVR); and three light chain CDRs, LCDR1, LCDR2, and LCDR3 contained within a light chain variable region (LCVR), wherein, (a) the HCDR1, HCDR2, HCDR3, LCDR1, LCDR2, and LCDR3 domains contained within a HCVR and LCVR pair comprise SEQ ID NOs: 4, 6, 8, 12, AAS, and SEQ ID NO: 16, respectively, wherein the HCVR and LCVR pair comprises SEQ ID NOs: 2 and 10;

(b) the HCDR1, HCDR2, HCDR3, LCDR1, LCDR2, and LCDR3 domains contained within a HCVR and LCVR pair comprise SEQ ID NOs: 24, 26, 28, 12, AAS, and SEQ ID NO: 32, respectively, wherein the HCVR and LCVR pair comprises SEQ ID Nos: 22 and 30;

(c) the HCDR1, HCDR2, HCDR3, LCDR1, LCDR2, and LCDR3 domains contained within a HCVR and LCVR pair comprise SEQ ID NOs: 40, 42, 44, 48, AAS, and SEQ ID NO: 16, respectively, wherein the HCVR and LCVR pair comprises SEQ ID Nos: 38 and 46; and (d) the HCDR1, HCDR2, HCDR3, LCDR1, LCDR2, and LCDR3 domains contained within a HCVR and LCVR pair comprise SEQ ID NOs: 57, 59, 61, 65, GAS, and SEQ ID NO: 69, respectively, wherein the HCVR and LCVR pair comprises SEQ ID Nos: 55 and 63.

28. The isolated antibody or antigen-binding fragment thereof claim 27, further comprising a heavy chain variable region (HCVR) and light chain variable region (LCVR) amino acid sequence pair selected from the group consisting of SEQ ID NOs: 2 and 10 if the HCDR1, HCDR2, HCDR3, LCDR1, LCDR2, and LCDR3 domains contained within a HCVR and LCVR pair comprise SEQ ID NOs: 4, 6, 8, 12, AAS, and SEQ ID NO:16; SEQ ID NOs: 22 and 30 if the HCDR1, HCDR2, HCDR3, LCDR1, LCDR2, and LCDR3 domains contained within a HCVR and LCVR pair comprise SEQ ID NOs: 24, 26, 28, 12, AAS, and SEQ ID NO: 32; SEQ ID NOs: 38 and 46 if the HCDR1, HCDR2, HCDR3, LCDR1, LCDR2, and LCDR3 domains contained within a HCVR and LCVR pair comprise SEQ ID NOs: 40, 42, 44, 48, AAS, and SEQ ID NO: 16; and SEQ ID NOs: 55 and 63 if the HCDR1, HCDR2, HCDR3, LCDR1, LCDR2, and LCDR3 domains contained within a HCVR and LCVR pair comprise SEQ ID NOs: 57, 59, 61, 65, GAS, and SEQ ID NO: 69.

29. The antibody or antigen-binding fragment thereof of claim 27 comprising a heavy chain and a light chain, wherein the heavy chain is selected from the group consisting of SEQ ID NO: 18 if the HCDR1, HCDR2, and HCDR3 domains contained within a HCVR comprise SEQ ID NOs: 4, 6 and 8; SEQ ID NO: 34 if the HCDR1, HCDR2, and HCDR3 domains contained within a HCVR comprise SEQ ID NOs: 24, 26, and 28; SEQ ID NO: 51 if the HCDR1, HCDR2, and HCDR3 domains contained within a HCVR comprise SEQ ID NOs: 40, 42, and 44; and SEQ ID NO: 71 if the HCDR1, HCDR2, and HCDR3 domains contained within a HCVR comprise SEQ ID NOs: 57, 59, and 61.

30. The antibody or antigen-binding fragment thereof of claim 27 comprising a heavy chain and light chain, wherein the light chain is selected from the group consisting of SEQ ID NO: 20 if the LCDR1, LCDR2, and LCDR3 domains contained within a LCVR comprise SEQ ID NOs: 12, AAS, and 16; SEQ ID NO: 36 if the LCDR1, LCDR2, and LCDR3 domains contained within a LCVR comprise SEQ ID NOs: 12, AAS, and 32; SEQ ID NO: 53 if the LCDR1, LCDR2, and LCDR3 domains contained within a LCVR comprise SEQ ID NOs: 48, AAS, and 16; and SEQ ID NO: 73 if the LCDR1, LCDR2, and LCDR3 domains contained within a LCVR comprise SEQ ID NOs: 65, GAS, and 69.

31. The antibody or antigen-binding fragment thereof of claim 27 comprising a heavy chain and a light chain, wherein the heavy chain and light chain pair is selected from the group consisting of SEQ ID NOs: 18 and 20, SEQ ID NOs: 34 and 36, SEQ ID NOs: 51 and 53, and SEQ ID NOs: 71 and 73.

* * * * *

SEQUENCE LISTING

Sequence total quantity: 78
SEQ ID NO: 1              moltype = DNA   length = 360
FEATURE                   Location/Qualifiers
source                    1..360
                          mol_type = other DNA
                          organism = synthetic construct
SEQUENCE: 1
gaggtgcagc tggtggagtc tggggggaggc ttggtacagc cggggggggtc cctgagactc   60
tcctgtgcag cctctggatt caccttttagc agctatgcca tgagctgggt ccgccaggct  120
ccagggaagg ggctggagtg ggtctcaact attagtggta gtggtactaa tacatactac  180
gcagactccg tgaagggccg gttcaccatc tccaacgaca attccaagaa cacgttgtat  240
ctgcaaatga acagcctgag agccgaggac acggccgtat attactgtgc gaattacgat  300
attttgactg gtcattcctt tgaatactgg ggccagggaa ccctggtcac cgtctcctca  360

SEQ ID NO: 2              moltype = AA   length = 120
FEATURE                   Location/Qualifiers
source                    1..120
                          mol_type = protein
                          organism = synthetic construct
SEQUENCE: 2
EVQLVESGGG LVQPGGSLRL SCAASGFTFS SYAMSWVRQA PGKGLEWVST ISGSGTNTYY   60
ADSVKGRFTI SNDNSKNTLY LQMNSLRAED TAVYYCANYD ILTGHSFEYW GQGTLVTVSS  120

SEQ ID NO: 3              moltype = DNA   length = 24
FEATURE                   Location/Qualifiers
source                    1..24
                          mol_type = other DNA
                          organism = synthetic construct
SEQUENCE: 3
ggattcacct ttagcagcta tgcc                                          24

SEQ ID NO: 4              moltype = AA   length = 8
FEATURE                   Location/Qualifiers
source                    1..8
                          mol_type = protein
                          organism = synthetic construct
SEQUENCE: 4
GFTFSSYA                                                             8

SEQ ID NO: 5              moltype = DNA   length = 24
FEATURE                   Location/Qualifiers
source                    1..24
                          mol_type = other DNA
                          organism = synthetic construct
SEQUENCE: 5
attagtggta gtggtactaa taca                                          24

SEQ ID NO: 6              moltype = AA   length = 8
FEATURE                   Location/Qualifiers
source                    1..8
                          mol_type = protein
                          organism = synthetic construct
SEQUENCE: 6
ISGSGTNT                                                             8

SEQ ID NO: 7              moltype = DNA   length = 39
FEATURE                   Location/Qualifiers
source                    1..39
                          mol_type = other DNA
                          organism = synthetic construct
SEQUENCE: 7
gcgaattacg atattttgac tggtcattcc tttgaatac                          39

SEQ ID NO: 8              moltype = AA   length = 13
FEATURE                   Location/Qualifiers
source                    1..13
                          mol_type = protein
                          organism = synthetic construct
SEQUENCE: 8
ANYDILTGHS FEY                                                       13

SEQ ID NO: 9              moltype = DNA   length = 321
FEATURE                   Location/Qualifiers
source                    1..321
                          mol_type = other DNA
                          organism = synthetic construct
SEQUENCE: 9
gccatccaga tgacccagtc tccatcctcc ctgtctgcat ctgtaggaga cagagtcacc   60

-continued

```
atcacttgcc gggcaagtca gggcattaga aatgatttag gctggtatca gcagaaacca  120
gggaaagccc ctgaactcct aatctatgct gcatccaggt taccaagtgg ggtcccatta  180
aggttcagcg gcagtggatc tggcacagat ttcactctca ccatcagcag cctgcagcct  240
gaagatgttg caacttatta ctgtctacaa gattacaatt acccattcac tttcggccct  300
gggaccaaag tggatatcaa a                                             321

SEQ ID NO: 10           moltype = AA   length = 107
FEATURE                 Location/Qualifiers
source                  1..107
                        mol_type = protein
                        organism = synthetic construct
SEQUENCE: 10
AIQMTQSPSS LSASVGDRVT ITCRASQGIR NDLGWYQQKP GKAPELLIYA ASRLPSGVPL   60
RFSGSGSGTD FTLTISSLQP EDVATYYCLQ DYNYPFTFGP GTKVDIK               107

SEQ ID NO: 11           moltype = DNA   length = 18
FEATURE                 Location/Qualifiers
source                  1..18
                        mol_type = other DNA
                        organism = synthetic construct
SEQUENCE: 11
cagggcatta gaaatgat                                                 18

SEQ ID NO: 12           moltype = AA   length = 6
FEATURE                 Location/Qualifiers
source                  1..6
                        mol_type = protein
                        organism = synthetic construct
SEQUENCE: 12
QGIRND                                                              6

SEQ ID NO: 13           moltype =    length =
SEQUENCE: 13
000

SEQ ID NO: 14           moltype =    length =
SEQUENCE: 14
000

SEQ ID NO: 15           moltype = DNA   length = 27
FEATURE                 Location/Qualifiers
source                  1..27
                        mol_type = other DNA
                        organism = synthetic construct
SEQUENCE: 15
ctacaagatt acaattaccc attcact                                       27

SEQ ID NO: 16           moltype = AA   length = 9
FEATURE                 Location/Qualifiers
source                  1..9
                        mol_type = protein
                        organism = synthetic construct
SEQUENCE: 16
LQDYNYPFT                                                           9

SEQ ID NO: 17           moltype = DNA   length = 1344
FEATURE                 Location/Qualifiers
source                  1..1344
                        mol_type = other DNA
                        organism = synthetic construct
SEQUENCE: 17
gaggtgcagc tggtggagtc tgggggaggc ttggtacagc cgggggggtc cctgagactc   60
tcctgtgcag cctctggatt cacctttagc agctatgcca tgagctgggt ccgccaggct  120
ccagggaagg ggctggagtg ggtctcaact attagtggta gtggtactaa tacatactac  180
gcagactccg tgaagggccg gttcaccatc tccaacgaca attccaagaa cacgttgtat  240
ctgcaaatga acagcctgag agccgaggac acggccgtat attactgtgc gaattacgat  300
attttgactg tcattccttt gaatactggg gccagggaa ccctggtcac cgtctcctca  360
gcctccacca agggcccatc ggtcttcccc ctggcgcctc gctccaggag cacctccgag  420
agcacagccg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacgaagacc  600
tacacctgca acgtagatca caagcccagc aacaccaagg tggacaagag agttgagtcc  660
aaatatggtc ccccatgccc accctgccca gcacctgagt tcctgggggg accatcagtc  720
ttcctgttcc ccccaaaacc caaggacact ctcatgatct cccggacccc tgaggtcacg  780
tgcgtggtgg tggacgtgag ccaggaagac cccgaggtcc agttcaactg gtacgtggat  840
ggcgtggagg tgcataatgc caagacaaag ccgcgggagg agcagttcaa cagcacgtac  900
cgtgtggtca gcgtcctcac cgtcctgcac caggactggc tgaacggcaa ggagtacaag  960
tgcaaggtct ccaacaaagg cctcccgtcc tccatcgaga aaaccatctc caaagccaaa  1020
gggcagcccc gagagccaca ggtgtacacc ctgcccccat cccaggagga gatgaccaag  1080
```

```
aaccaggtca gcctgacctg cctggtcaaa ggcttctacc ccagcgacat cgccgtggag  1140
tgggagagca atgggcagcc ggagaacaac tacaagacca cgcctcccgt gctggactcc  1200
gacggctcct tcttcctcta cagcaggctc accgtggaca gagcaggtg  gcaggagggg   1260
aatgtcttct catgctccgt gatgcatgag gctctgcaca accactacac acagaagtcc  1320
ctctcccctgt ctctgggtaa atga                                        1344
```

SEQ ID NO: 18             moltype = AA   length = 447
FEATURE                   Location/Qualifiers
source                    1..447
                          mol_type = protein
                          organism = synthetic construct
SEQUENCE: 18
```
EVQLVESGGG LVQPGGSLRL SCAASGFTFS SYAMSWVRQA PGKGLEWVST ISGSGTNTYY  60
ADSVKGRFTI SNDNSKNTLY LQMNSLRAED TAVYYCANYD ILTGHSFEYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                       447
```

SEQ ID NO: 19             moltype = DNA   length = 645
FEATURE                   Location/Qualifiers
source                    1..645
                          mol_type = other DNA
                          organism = synthetic construct
SEQUENCE: 19
```
gccatccaga tgacccagtc tccatcctcc ctgtctgcat ctgtaggaga cagagtcacc  60
atcacttgcc gggcaagtca gggcattaga aatgatttag ctggtatca  gcagaaacca   120
gggaaagccc ctgaactcct aatctatgct gcatccagtt taccaagtgg ggtcccatta  180
aggttcagcg gcagtggatc tggcacagat ttcactctca ccatcagcag cctgcagcct  240
gaagatgttg caacttatta ctgtctacaa gattacaatt acccattcac tttcggccct  300
gggaccaaag tggatatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag cacccctgacg  540
ctgagcaaag cagactacga gaaacacaaa gtctacgcct gcgaagtcac ccatcagggc  600
ctgagctcgc ccgtcacaaa gagcttcaac aggggagagt gttag               645
```

SEQ ID NO: 20             moltype = AA   length = 214
FEATURE                   Location/Qualifiers
source                    1..214
                          mol_type = protein
                          organism = synthetic construct
SEQUENCE: 20
```
AIQMTQSPSS LSASVGDRVT ITCRASQGIR NDLGWYQQKP GKAPELLIYA ASRLPSGVPL  60
RFSGSGSGTD FTLTISSLQP EDVATYYCLQ DYNYPFTGP GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214
```

SEQ ID NO: 21             moltype = DNA   length = 360
FEATURE                   Location/Qualifiers
source                    1..360
                          mol_type = other DNA
                          organism = synthetic construct
SEQUENCE: 21
```
gaggtgcagc tggtggagtc tggggggaggc ttggtacagc ctgggggggtc cctgagactc  60
tcctgtgcag cctctggatt ctcctttgtc agctatgtca tgggctgggt ccgccaggct  120
ccaggggaag ggctggagtg ggtctcaagt attagtggaa gtcttacgaa cacatactac  180
gcagacccccg tgaagggccg gttcaccatc tccagagaca attccaagaa cacgctgtat  240
ctgcaaatga acagcctgag agccgaggac acggccgcat attactgtgt gacctacgat  300
attttgactg gtcatctctt tgactactgg ggccagggaa ccctggtcac cgtctcctca  360
```

SEQ ID NO: 22             moltype = AA   length = 120
FEATURE                   Location/Qualifiers
source                    1..120
                          mol_type = protein
                          organism = synthetic construct
SEQUENCE: 22
```
EVQLVESGGG LVQPGGSLRL SCAASGFSFV SYVMGWVRQA PGKGLEWVSS ISGSLTNTYY  60
ADPVKGRFTI SRDNSKNTLY LQMNSLRAED TAAYYCVTYD ILTGHLFDYW GQGTLVTVSS  120
```

SEQ ID NO: 23             moltype = DNA   length = 24
FEATURE                   Location/Qualifiers
source                    1..24
                          mol_type = other DNA
                          organism = synthetic construct
SEQUENCE: 23
```
ggattctcct ttgtcagcta tgtc                                         24
```

-continued

```
SEQ ID NO: 24          moltype = AA  length = 8
FEATURE                Location/Qualifiers
source                 1..8
                       mol_type = protein
                       organism = synthetic construct
SEQUENCE: 24
GFSFVSYV                                                          8

SEQ ID NO: 25          moltype = DNA  length = 24
FEATURE                Location/Qualifiers
source                 1..24
                       mol_type = other DNA
                       organism = synthetic construct
SEQUENCE: 25
attagtggaa gtcttacgaa caca                                       24

SEQ ID NO: 26          moltype = AA  length = 8
FEATURE                Location/Qualifiers
source                 1..8
                       mol_type = protein
                       organism = synthetic construct
SEQUENCE: 26
ISGSLTNT                                                          8

SEQ ID NO: 27          moltype = DNA  length = 39
FEATURE                Location/Qualifiers
source                 1..39
                       mol_type = other DNA
                       organism = synthetic construct
SEQUENCE: 27
gtgacctacg atattttgac tggtcatctc tttgactac                       39

SEQ ID NO: 28          moltype = AA  length = 13
FEATURE                Location/Qualifiers
source                 1..13
                       mol_type = protein
                       organism = synthetic construct
SEQUENCE: 28
VTYDILTGHL FDY                                                    13

SEQ ID NO: 29          moltype = DNA  length = 321
FEATURE                Location/Qualifiers
source                 1..321
                       mol_type = other DNA
                       organism = synthetic construct
SEQUENCE: 29
gccatccaga tgacccagtc tccatcctcc ctgtctgcat ctgtaggaga cagagtcacc  60
atcacttgcc ggtcaagtca gggcattaga aatgattttg gctggtatca gcagaaacca  120
gggaaagccc ctaaactcct gatctatgct gcatccagat tacaaagtgg ggtcccatca  180
aggttcagcg gcagtggatc tggcacagat ttcactctca ccatcaacaa cctgcagcct  240
gaagattttg caacttatta ctgtctccaa gattacactt acccattcac tttcggccct  300
gggaccaaag tggatatcaa a                                           321

SEQ ID NO: 30          moltype = AA  length = 107
FEATURE                Location/Qualifiers
source                 1..107
                       mol_type = protein
                       organism = synthetic construct
SEQUENCE: 30
AIQMTQSPSS LSASVGDRVT ITCRSSQGIR NDFGWYQQKP GKAPKLLIYA ASRLQSGVPS  60
RFSGSGSGTD FTLTINNLQP EDFATYYCLQ DYTYPFTFGP GTKVDIK               107

SEQ ID NO: 31          moltype = DNA  length = 27
FEATURE                Location/Qualifiers
source                 1..27
                       mol_type = other DNA
                       organism = synthetic construct
SEQUENCE: 31
ctccaagatt acacttaccc attcact                                    27

SEQ ID NO: 32          moltype = AA  length = 9
FEATURE                Location/Qualifiers
source                 1..9
                       mol_type = protein
                       organism = synthetic construct
SEQUENCE: 32
LQDYTYPFT                                                         9
```

-continued

```
SEQ ID NO: 33          moltype = DNA   length = 1344
FEATURE                Location/Qualifiers
source                 1..1344
                       mol_type = other DNA
                       organism = synthetic construct
SEQUENCE: 33
gaggtgcagc tggtggagtc tggggggaggc ttggtacagc ctggggggtc cctgagactc    60
tcctgtgcag cctctggatt ctcctttgtc agctatgtca tgggctgggt ccgccaggct   120
ccagggaagg ggctggagtg ggtctcaagt attagtggaa gtcttacgaa cacatactac   180
gcagaccccg tgaagggccg gttcaccatc tccagagaca attccaagaa cacgctgtat   240
ctgcaaatga acagcctgag agccgaggac acggccgcat attactgtgt gacctacgat   300
attttgactg tcatctctt tgactactgg ggccagggaa ccctggtcac cgtctcctca   360
gcctccacca aagggcccat cggtcttccc ctggcgccct gctccaggag cacctccgag   420
agcacagccg ccctgggctg cctggtcaag gactacttcc ccgaaccggt gacggtgtcg   480
tggaactcag gcgccctgac cagcggcgtg cacaccttcc cggctgtcct acagtcctca   540
ggactctact ccctcagcag cgtggtgacc gtgccctcca gcagcttggg cacgaagacc   600
tacacctgca acgtagatca caagcccagc aacaccaagg tggacaagag agttgagtcc   660
aaatatggtc ccccatgccc accctgccca gcacctgaacct tcctgggggg accatcagtc   720
ttcctgttcc ccccaaaacc caaggacact ctcatgatct cccggacccc tgaggtcacg   780
tgcgtggtgg tggacgtgag ccaggaagac cccgaggtcc agttcaactg gtacgtggat   840
ggcgtggagg tgcataatgc caagacaaag ccgcgggagg agcagttcaa cagcacgtac   900
cgtgtggtca gcgtcctcac cgtcctgcac caggactggc tgaacggcaa ggagtacaag   960
tgcaaggtct ccaacaaagg cctcccgtcc tccatcgaga aaaccatctc caaagccaaa  1020
gggcagcccc gagagccaca ggtgtacacc ctgcccccat cccaggagga gatgaccaag  1080
aaccaggtca gcctgacctg cctggtcaaa ggcttctacc ccagcgacat cgccgtggag  1140
tgggagagca atgggcagcc ggagaacaac tacaagacca cgcctcccgt gctggactcc  1200
gacggctcct tcttcctcta cagcaggctc accgtggaca gagcaggtg gcaggagggg  1260
aatgtcttct catgctccgt gatgcatgag gctctgcaca accactacac acagaagtcc  1320
ctctccctgt ctctgggtaa atga                                         1344

SEQ ID NO: 34          moltype = AA   length = 447
FEATURE                Location/Qualifiers
source                 1..447
                       mol_type = protein
                       organism = synthetic construct
SEQUENCE: 34
EVQLVESGGG LVQPGGSLRL SCAASGFSFV SYVMGWVRQA PGKGLEWVSS ISGSLTNTYY    60
ADPVKGRFTI SRDNSKNTLY LQMNSLRAED TAAYYCVTYD ILTGHLFDYW GQGTLVTVSS   120
ASTKGPSVFP LAPCSRSTSE STAALGCLVK DYFPEPVTVS WNSGALTSGV HTFPAVLQSS   180
GLYSLSSVVT VPSSSLGTKT YTCNVDHKPS NTKVDKRVES KYGPPCPPCP APEFLGGPSV   240
FLFPPKPKDT LMISRTPEVT CVVVDVSQED PEVQFNWYVD GVEVHNAKTK PREEQFNSTY   300
RVVSVLTVLH QDWLNGKEYK CKVSNKGLPS SIEKTISKAK GQPREPQVYT LPPSQEEMTK   360
NQVSLTCLVK GFYPSDIAVE WESNGQPENN YKTTPPVLDS DGSFFLYSRL TVDKSRWQEG   420
NVFSCSVMHE ALHNHYTQKS LSLSLGK                                       447

SEQ ID NO: 35          moltype = DNA   length = 645
FEATURE                Location/Qualifiers
source                 1..645
                       mol_type = other DNA
                       organism = synthetic construct
SEQUENCE: 35
gccatccaga tgacccagtc tccatcctcc ctgtctgcat ctgtaggaga cagagtcacc    60
atcacttgcc ggtcaagtca gggcattaga aatgattttg ctggtatca gcagaaacca   120
gggaaagccc ctaaactcct gatctatgct gcatccagat tacaaagtgg ggtcccatca   180
aggttcagcg gcagtggatc tgggacagat ttcactctca ccatcaacaa cctgcagcct   240
gaagattttg caacttatta ctgtctccaa gattacactt acccattcac tttcggccct   300
gggaccaaag tggatatcaa acgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gttag                  645

SEQ ID NO: 36          moltype = AA   length = 214
FEATURE                Location/Qualifiers
source                 1..214
                       mol_type = protein
                       organism = synthetic construct
SEQUENCE: 36
AIQMTQSPSS LSASVGDRVT ITCRSSQGIR NDFGWYQQKP GKAPKLLIYA ASRLQSGVPS    60
RFSGSGSGTD FTLTINNLQP EDFATYYCLQ DYTYPFTFGP GTKVDIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 37          moltype = DNA   length = 360
FEATURE                Location/Qualifiers
source                 1..360
                       mol_type = other DNA
                       organism = synthetic construct
```

-continued

```
SEQUENCE: 37
caggtccagc tggtacagtc tggggctgag gtgaagaagc ctggggcctc agtgaaggtt    60
tcctgcaagg catctggata caccttcacc agctattata tacactgggt gcgacaggcc    120
cctggacaag ggcttgagtg gatgggaata atcagcccta gtgatggtta cacaagctac    180
gcacagaact tccagggcag agtcaccatg accagggaca cgtccacgaa cacagtctac    240
atggacctga gcagcctgag atctgaggac acggccatgt tttactgtgc gagaaatgat    300
cctctgacca cagtcgccct tgactactgg ggccagggaa ccctggtcac cgtctcctca    360

SEQ ID NO: 38          moltype = AA  length = 120
FEATURE                Location/Qualifiers
source                 1..120
                       mol_type = protein
                       organism = synthetic construct
SEQUENCE: 38
QVQLVQSGAE VKKPGASVKV SCKASGYTFT SYYIHWVRQA PGQGLEWMGI ISPSDGYTSY    60
AQNFQGRVTM TRDTSTNTVY MDLSSLRSED TAMFYCARND PLTTVALDYW GQGTLVTVSS    120

SEQ ID NO: 39          moltype = DNA  length = 24
FEATURE                Location/Qualifiers
source                 1..24
                       mol_type = other DNA
                       organism = synthetic construct
SEQUENCE: 39
ggatacacct tcaccagcta ttat                                           24

SEQ ID NO: 40          moltype = AA  length = 8
FEATURE                Location/Qualifiers
source                 1..8
                       mol_type = protein
                       organism = synthetic construct
SEQUENCE: 40
GYTFTSYY                                                             8

SEQ ID NO: 41          moltype = DNA  length = 24
FEATURE                Location/Qualifiers
source                 1..24
                       mol_type = other DNA
                       organism = synthetic construct
SEQUENCE: 41
atcagcccta gtgatggtta caca                                           24

SEQ ID NO: 42          moltype = AA  length = 8
FEATURE                Location/Qualifiers
source                 1..8
                       mol_type = protein
                       organism = synthetic construct
SEQUENCE: 42
ISPSDGYT                                                             8

SEQ ID NO: 43          moltype = DNA  length = 39
FEATURE                Location/Qualifiers
source                 1..39
                       mol_type = other DNA
                       organism = synthetic construct
SEQUENCE: 43
gcgagaaatg atcctctgac cacagtcgcc cttgactac                           39

SEQ ID NO: 44          moltype = AA  length = 13
FEATURE                Location/Qualifiers
source                 1..13
                       mol_type = protein
                       organism = synthetic construct
SEQUENCE: 44
ARNDPLTTVA LDY                                                       13

SEQ ID NO: 45          moltype = DNA  length = 321
FEATURE                Location/Qualifiers
source                 1..321
                       mol_type = other DNA
                       organism = synthetic construct
SEQUENCE: 45
gccatccaga tgacccagtc tccatcctcc ctgtctgcat ctgtaggaga cagagtcacc    60
atcacttgcc gggcaagtca gggcattaga tatgatttag ctggtttca gcagaaacca    120
gggaaagccc ctaaactcct gatccatgct gcatccagtt tacaaagtgg ggtcccatca    180
aggttcagcg gcagtggatc tggcacagat ttcactctca ccatcagcag cctgcagcct    240
gaagattttg caacttatta ctgtctacaa gactacaatt acccgttcac ttttggccag    300
gggaccaagc tggagatcaa a                                              321

SEQ ID NO: 46          moltype = AA  length = 107
```

-continued

```
FEATURE                 Location/Qualifiers
source                  1..107
                        mol_type = protein
                        organism = synthetic construct
SEQUENCE: 46
AIQMTQSPSS LSASVGDRVT ITCRASQGIR YDLGWFQQKP GKAPKLLIHA ASSLQSGVPS   60
RFSGSGSGTD FTLTISSLQP EDFATYYCLQ DYNYPFTFGQ GTKLEIK                 107

SEQ ID NO: 47           moltype = DNA   length = 18
FEATURE                 Location/Qualifiers
source                  1..18
                        mol_type = other DNA
                        organism = synthetic construct
SEQUENCE: 47
caggggcatta gatatgat                                                18

SEQ ID NO: 48           moltype = AA   length = 6
FEATURE                 Location/Qualifiers
source                  1..6
                        mol_type = protein
                        organism = synthetic construct
SEQUENCE: 48
QGIRYD                                                              6

SEQ ID NO: 49           moltype = DNA   length = 27
FEATURE                 Location/Qualifiers
source                  1..27
                        mol_type = other DNA
                        organism = synthetic construct
SEQUENCE: 49
ctacaagact acaattaccc gttcact                                       27

SEQ ID NO: 50           moltype = DNA   length = 1344
FEATURE                 Location/Qualifiers
source                  1..1344
                        mol_type = other DNA
                        organism = synthetic construct
SEQUENCE: 50
caggtccagc tggtacagtc tgggggctgag gtgaagaagc ctggggcctc agtgaaggtt   60
tcctgcaagg catctggata caccttcacc agctattata tacactgggt gcgacaggcc  120
cctggacaag ggcttgagtg gatgggaata atcagcccta gtgatggtta cacaagctac  180
gcacagaact tccagggcag agtcaccatg accagggaca cgtccacgaa cacagtctac  240
atggacctga gcagcctgag atctgaggac acggccatgt tttactgtgc gagaaatgat  300
cctctgacca cagtcgccct tgactactgg ggccaggggca ccctggtcac cgtctcctca  360
gcctccacca agggcccatc ggtcttcccc ctggcgccct gctccaggag cacctccgag  420
agcacagccg ccctgggctg cctggtcaag gactacttcc ccgaaccggt gacggtgtcg  480
tggaactcag gcgccctgac cagcggcgtg cacaccttct cggctgtcct acagtcctca  540
ggactctact ccctcagcag cgtggtgacc gtgccctcca gcagcttggg cacgaagacc  600
tacacctgca acgtagatca caagcccagc aacaccaagg tggacaagag agttgagtcc  660
aaatatggtc cccatgccc acctgccca gcacctgagt tcctggggg accatcagtc  720
ttcctgttcc cccaaaaccc aaggacact ctcatgatct cccggacccc tgaggtcacg  780
tgcgtggtgg tggacgtgag ccaggaagac cccgaggtcc agttcaactg gtacgtggat  840
ggcgtggagg tgcataatgc caagacaaag ccgcgggagg agcagttcaa cagcacgtac  900
cgtgtggtca gcgtcctcac cgtcctgcac caggactggc tgaacggcaa ggagtacaag  960
tgcaaggtct ccaacaaagg cctcccgtcc tccatcgaga aaaccatctc caaagccaaa 1020
gggcagcccc gagagccaca ggtgtacacc ctgcccccat cccaggagga gatgaccaag 1080
aaccaggtca gcctgacctg cctggtcaaa ggcttctacc ccagcgacat cgccgtggag 1140
tgggagagca atgggcagcc ggagaacaac tacaagacca cgcctcccgt gctggactcc 1200
gacggctcct tcttcctcta cagcaggctc accgtggaca gagcaggtg gcaggagggg 1260
aatgtcttct catgctccgt gatgcatgag gctctgcaca accactacac acagaagtcc 1320
ctctccctgt ctctgggtaa atga                                         1344

SEQ ID NO: 51           moltype = AA   length = 447
FEATURE                 Location/Qualifiers
source                  1..447
                        mol_type = protein
                        organism = synthetic construct
SEQUENCE: 51
QVQLVQSGAE VKKPGASVKV SCKASGYTFT SYYIHWVRQA PGQGLEWMGI ISPSDGYTSY   60
AQNFQGRVTM TRDTSTNTVY MDLSSLRSED TAMFYCARND PLTTVALDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                      447

SEQ ID NO: 52           moltype = DNA   length = 645
FEATURE                 Location/Qualifiers
```

```
source                  1..645
                        mol_type = other DNA
                        organism = synthetic construct
SEQUENCE: 52
gccatccaga tgacccagtc tccatcctcc ctgtctgcat ctgtaggaga cagagtcacc   60
atcacttgcc gggcaagtca gggcattaga tatgatttag gctggtttca gcagaaacca  120
gggaaagccc ctaaactcct gatccatgct gcatccagtt tacaaagtgg ggtcccatca  180
aggttcagcg gcagtggatc tggcacagat ttcactctca ccatcagcag cctgcagcct  240
gaagatttg caacttatta ctgtctacaa gactacaatt acccgttcac ttttggccag  300
gggaccaagc tggagatcaa acgaactgtg gctgcaccat ctgtcttcat cttcccgcca  360
tctgatgagc agttgaaatc tggaactgcc tctgttgtgt gcctgctgaa taacttctat  420
cccagagag ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 53              moltype = AA  length = 214
FEATURE                   Location/Qualifiers
source                    1..214
                          mol_type = protein
                          organism = synthetic construct
SEQUENCE: 53
AIQMTQSPSS LSASVGDRVT ITCRASQGIR YDLGWFQQKP GKAPKLLIHA ASSLQSGVPS   60
RFSGSGSGTD FTLTISSLQP EDFATYYCLQ DYNYPFTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 54              moltype = DNA  length = 372
FEATURE                   Location/Qualifiers
source                    1..372
                          mol_type = other DNA
                          organism = synthetic construct
SEQUENCE: 54
gaggtgcagc tattggagtc tgggggagac ttggtacagc ctggggggtc cctgagactc   60
tcctgtgcag cctctggatt caccttagc gactatgcca tgatctggt ccgccagact  120
ccagggaagg gactggaatg ggtctcaggt atcagtggtg gtggtggaag cacagactac  180
gcagactccg tgaagggccg gttcaccacc tccagagaca atgtcaagaa tgcgatgtat  240
ctgcaaatga acagcctgag aaccgaggac acggccgtat attattgtgc gagagaggac  300
caactgccat catatcacaa ttattacggt atggacgtct ggggccaggg gaccacggtc  360
accgtctcct ca                                                      372

SEQ ID NO: 55              moltype = AA  length = 124
FEATURE                   Location/Qualifiers
source                    1..124
                          mol_type = protein
                          organism = synthetic construct
SEQUENCE: 55
EVQLLESGGD LVQPGGSLRL SCAASGFTFS DYAMIWVRQT PGKGLEWVSG ISGGGGSTDY   60
ADSVKGRFTT SRDNVKNAMY LQMNSLRTED TAVYYCARED QLPSYHNYYG MDVWGQGTTV  120
TVSS                                                                124

SEQ ID NO: 56              moltype = DNA  length = 24
FEATURE                   Location/Qualifiers
source                    1..24
                          mol_type = other DNA
                          organism = synthetic construct
SEQUENCE: 56
ggattcacct ttagcgacta tgcc                                          24

SEQ ID NO: 57              moltype = AA  length = 8
FEATURE                   Location/Qualifiers
source                    1..8
                          mol_type = protein
                          organism = synthetic construct
SEQUENCE: 57
GFTFSDYA                                                            8

SEQ ID NO: 58              moltype = DNA  length = 24
FEATURE                   Location/Qualifiers
source                    1..24
                          mol_type = other DNA
                          organism = synthetic construct
SEQUENCE: 58
atcagtggtg gtggtggaag caca                                          24

SEQ ID NO: 59              moltype = AA  length = 8
FEATURE                   Location/Qualifiers
source                    1..8
                          mol_type = protein
```

```
SEQUENCE: 59
ISGGGGST                                                          8

SEQ ID NO: 60          moltype = DNA   length = 51
FEATURE                Location/Qualifiers
source                 1..51
                       mol_type = other DNA
                       organism = synthetic construct
SEQUENCE: 60
gcgagagagg accaactgcc atcatatcac aattattacg gtatggacgt c       51

SEQ ID NO: 61          moltype = AA   length = 17
FEATURE                Location/Qualifiers
source                 1..17
                       mol_type = protein
                       organism = synthetic construct
SEQUENCE: 61
AREDQLPSYH NYYGMDV                                                17

SEQ ID NO: 62          moltype = DNA   length = 321
FEATURE                Location/Qualifiers
source                 1..321
                       mol_type = other DNA
                       organism = synthetic construct
SEQUENCE: 62
gacatccaga tgacccagtc tccatcctca gtgtctgcat ctgtaggaga cagagtcacc  60
atcacttgtc gggcgagtca gggcatcaac aattatttag cctggtttca gcagaaacca  120
gggaaagccc caaagtccct gatctatggc gcatccagtt tgcaaagtgg ggtcccatca  180
aagttcagcg gcagcagatc tgggcatagat ttcactctca ccatcagcag cctgcagcct  240
gaagattttg caacttatta ctgccaacag tacaatagtt atccgtacac ttttggccag  300
gggaccaagc tggagatcaa a                                           321

SEQ ID NO: 63          moltype = AA   length = 107
FEATURE                Location/Qualifiers
source                 1..107
                       mol_type = protein
                       organism = synthetic construct
SEQUENCE: 63
DIQMTQSPSS VSASVGDRVT ITCRASQGIN NYLAWFQQKP GKAPKSLIYG ASSLQSGVPS  60
KFSGSRSGID FTLTISSLQP EDFATYYCQQ YNSYPYTFGQ GTKLEIK                107

SEQ ID NO: 64          moltype = DNA   length = 18
FEATURE                Location/Qualifiers
source                 1..18
                       mol_type = other DNA
                       organism = synthetic construct
SEQUENCE: 64
cagggcatca acaattat                                               18

SEQ ID NO: 65          moltype = AA   length = 6
FEATURE                Location/Qualifiers
source                 1..6
                       mol_type = protein
                       organism = synthetic construct
SEQUENCE: 65
QGINNY                                                            6

SEQ ID NO: 66          moltype =    length =
SEQUENCE: 66
000

SEQ ID NO: 67          moltype =    length =
SEQUENCE: 67
000

SEQ ID NO: 68          moltype = DNA   length = 27
FEATURE                Location/Qualifiers
source                 1..27
                       mol_type = other DNA
                       organism = synthetic construct
SEQUENCE: 68
caacagtaca atagttatcc gtacact                                     27

SEQ ID NO: 69          moltype = AA   length = 9
FEATURE                Location/Qualifiers
source                 1..9
                       mol_type = protein
                       organism = synthetic construct
```

-continued

```
SEQUENCE: 69
QQYNSYPYT                                                              9

SEQ ID NO: 70          moltype = DNA  length = 1356
FEATURE                Location/Qualifiers
source                 1..1356
                       mol_type = other DNA
                       organism = synthetic construct
SEQUENCE: 70
gaggtgcagc tattggagtc tggggggagac ttggtacagc ctgggggtc cctgagactc   60
tcctgtgcag cctctggatt caccttagc gactatgcca tgatctgggt ccgccagact  120
ccagggaagg gactggaatg ggtctcaggt atcagtggtg gtggtggaag cacagactac  180
gcagactccg tgaagggccg gttcaccacc tccagagaca atgtcaagaa tgcgatgtat  240
ctgcaaatga cagcctgag aaccgaggac acggccgtat attattgtgc gagagaggac  300
caactgccat catatcacaa ttattacggt atggacgtct gggccaggg gaccacggtc  360
accgtctcct cagcctccac caagggccca tcggtcttcc ccctggcgcc ctgctccagg  420
agcacctccg agagcacagc cgccctgggc tgcctggtca aggactactt ccccgaaccg  480
gtgacggtgt cgtggaactc aggcgcccctg accagcggcg tgcacacctt ccggctgtcc  540
ctacagtcct caggactcta ctccctcagc agcgtggtga ccgtgccctc cagcagcttg  600
ggcacgaaga cctacacctg caacgtagat cacaagccca gcaacaccaa ggtggacaag  660
agagttgagt ccaaatatgg tccccatgc ccaccctgcc cagcacctga gttcctgggg  720
ggaccatcag tcttcctgtt cccccaaaa cccaaggaca ctctcatgat ctcccggacc  780
cctgaggtca cgtgcgtggt ggtggacgtg agccaggaag accccgaggt ccagttcaac  840
tggtacgtgg atggcgtgga ggtgcataat gccaagacaa agccgcggga ggagcagttc  900
aacagcacgt accgtgtggt cagcgtcctc accgtcctgc accaggactg gctgaacggc  960
aaggagtaca agtgcaaggt ctccaacaaa ggcctcccgt cctccatcga gaaaaccatc 1020
tccaaagcca aagggcagcc ccgagagcca caggtgtaca ccctgccccc atcccaggag 1080
gagatgacca gaaccaggt cagcctgacc tgcctggtca aaggcttcta ccccagcgac 1140
atcgccgtgg agtgggagag caatgggcag ccggagaaca actacaagac cacgcctccc 1200
gtgctggact ccgacggctc cttcttcctc tacagcaggc tcaccgtgga caagagcagg 1260
tggcaggagg ggaatgtctt ctcatgctcc gtgatgcatg aggctctgca caaccactac 1320
acacagaagt ccctctccct gtctctgggt aaatga                            1356

SEQ ID NO: 71          moltype = AA  length = 451
FEATURE                Location/Qualifiers
source                 1..451
                       mol_type = protein
                       organism = synthetic construct
SEQUENCE: 71
EVQLLESGGD LVQPGGSLRL SCAASGFTFS DYAMIWVRQT PGKGLEWVSG ISGGGGSTDY   60
ADSVKGRFTT SRDNVKNAMY LQMNSLRTED TAVYYCARED QLPSYHNYYG MDVWGQGTTV  120
TVSSASTKGP SVFPLAPCSR STSESTAALG CLVKDYFPEP VTVSWNSGAL TSGVHTFPAV  180
LQSSGLYSLS SVVTVPSSSL GTKTYTCNVD HKPSNTKVDK RVESKYGPPC PPCPAPEFLG  240
GPSVFLFPPK PKDTLMISRT PEVTCVVVDV SQEDPEVQFN WYVDGVEVHN AKTKPREEQF  300
NSTYRVVSVL TVLHQDWLNG KEYKCKVSNK GLPSSIEKTI SKAKGQPREP QVYTLPPSQE  360
EMTKNQVSLT CLVKGFYPSD IAVEWESNGQ PENNYKTTPP VLDSDGSFFL YSRLTVDKSR  420
WQEGNVFSCS VMHEALHNHY TQKSLSLSLG K                                  451

SEQ ID NO: 72          moltype = DNA  length = 645
FEATURE                Location/Qualifiers
source                 1..645
                       mol_type = other DNA
                       organism = synthetic construct
SEQUENCE: 72
gacatccaga tgacccagtc tccatcctca gtgtctgcat ctgtaggaga cagagtcacc   60
atcacttgtc gggcgagtca gggcatcaac aattatttag cctggtttca gcagaaacca  120
gggaaagccc caaagtccct gatctatggc gcatccagtt tgcaaagtgg ggtcccatca  180
aagttcagcg gcagcagatc tgggacagat ttcactctca ccatcagcag cctgcagcct  240
gaagattttg caacttatta ctgccaacag tacaatagt atccgtacac ttttggccag  300
gggaccaagc tggagatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 73          moltype = AA  length = 214
FEATURE                Location/Qualifiers
source                 1..214
                       mol_type = protein
                       organism = synthetic construct
SEQUENCE: 73
DIQMTQSPSS VSASVGDRVT ITCRASQGIN NYLAWFQQKP GKAPKSLIYG ASSLQSGVPS   60
KFSGSRSGID FTLTISSLQP EDFATYYCQQ YNSYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 74          moltype = AA  length = 469
FEATURE                Location/Qualifiers
```

-continued

```
source                    1..469
                          mol_type = protein
                          organism = synthetic construct
SEQUENCE: 74
GNLTVAVVLP LANTSYPWSW ARVGPAVELA LAQVKARPDL LPGWTVRTVL GSSENALGVC  60
SDTAAPLAAV DLKWEHNPAV FLGPGCVYAA APVGRFTAHW RVPLLTAGAP ALGFGVKDEY  120
ALTTRAGPSY AKLGDFVAAL HRRLGWERQA LMLYAYRPGD EEHCFFLVEG LFMRVRDRLN  180
ITVDHLEFAE DDLSHYTRLL RTMPRKGRVI YICSSPDAFR TLMLLALEAG LCGEDYVFFH  240
LDIFGQSLQG GQGPAPRRPW ERGDGQDVSA RQAFQAAKII TYKDPDNPEY LEFLKQLKHL  300
AYEQFNFTME DGLVNTIPAS FHDGLLLYIQ AVTETLAHGG TVTDGENITQ RMWNRSFQGV  360
TGYLKIDSSG DRETDFSLWD MDPENGAFRV VLNYNGTSQE LVAVSGRKLN WPLGYPPPDI  420
PKCGFDNEDP ACNQDHLSTL EEQKLISEED LGGEQKLISE EDLHHHHHH             469

SEQ ID NO: 75            moltype = AA  length = 469
FEATURE                  Location/Qualifiers
source                    1..469
                          mol_type = protein
                          organism = synthetic construct
SEQUENCE: 75
GNLTVAVVLP LANTSYPWSW ARVGPAVELA LARVKARPDL LPGWTVRTVL GSSENALGVC  60
SDTAAPLAAV DLKWEHNPAA FLGPGCVYAA APVGRFTAHW RVPLLTAGAP ALGFGVKDEY  120
ALTTRAGPSY AKLGDFVAAL HRRLGWERQA LMLYAYRPGD EEHCFFLVEG LFMRVRDRLN  180
ITVDHLEFAE DDLSHYTRLL RTMPRKGRVI YICSSPDAFR TLMLLALEAG LCGEDYVFFH  240
LDIFGQSLQG GQGPAPRRPW ERGDGQDVSA RQAFQAAKII TYKEPDNPEY LEFLKQLKHL  300
AREQFNFTME DGLVNTIPAS FHDGLLLYIQ AVTETLAHGG TVTDGENITQ RMWNRSFQGV  360
TGYLKIDSSG DRETDFSLWD MDPETGAFRV VLNYNGTSQE LVAVSGRKLN WPLGYPPPDI  420
PKCGFDNEDP ACNQDHLSTL EEQKLISEED LGGEQKLISE EDLHHHHHH             469

SEQ ID NO: 76            moltype = AA  length = 469
FEATURE                  Location/Qualifiers
source                    1..469
                          mol_type = protein
                          organism = synthetic construct
SEQUENCE: 76
SDLTVAVVLP LTNTSYPWSW ARVGPAVELA LGRVKARPDL LPGWTVRMVL GSSENAAGVC  60
SDTAAPLAAV DLKWEHSPAV FLGPGCVYSA APVGRFTAHW RVPLLTAGAP ALGIGVKDEY  120
ALTTRTGPSH VKLGDFVTAL HRRLGWEHQA LVLYADRLGD DRPCFFIVEG LYMRVRERLN  180
ITVNHQEFVE GDPDHYTKLL RTVQRKGRVI YICSSPDAFR NLMLLALDAG LTGEDYVFFH  240
LDVFGQSLQG AQGPVPRKPW ERDDGQDRRA RQAFQAAKII TYKEPDNPEY LEFLKQLKLL  300
ADKKFNFTME DGLKNIIPAS FHDGLLLYVQ AVTETLAQGG TVTDGENITQ RMWNRSFQGV  360
TGYLKIDRNG DRDTDFSLWD MDPETGAFRV VLNFNGTSQE LMAVSEHRLY WPLGYPPPDI  420
PKCGFDNEDP ACNQDHFSTL EEQKLISEED LGGEQKLISE EDLHHHHHH             469

SEQ ID NO: 77            moltype = AA  length = 469
FEATURE                  Location/Qualifiers
source                    1..469
                          mol_type = protein
                          organism = synthetic construct
SEQUENCE: 77
GNLTVAVVLP LANTSYPWSW ARVGPAVELA LAAVRAQPDL LPGWTVRTVL GSSENALGVC  60
SDTAAPLAAV DLKWEHSPAV FLGPGCVYAA APVGRFTAHW RVPLLTAGAP ALGFGAKDEY  120
ALTTRAGPSH AKLGDLVAAL HRRLGWERRA LVLYAYRPGD DQPCFFVVEG LYVRVRERLN  180
ITVDHLEFAE GDLDQYALLL HTVRRQGRVI YICSSPDAFR TLMLLAMEAG LSGEDYVFFH  240
LDLFGHSLQG APGLAPHRPW ERGDGQDVSA HQAFQAAKII TYKEPENPEY LEFLQQLKHL  300
AHEQFNFTVE DGLVNTIPAS FHDGLLLYVQ AVTETLAHGG AVTDGEAITQ RMRNRSFQGV  360
TGYLKMDSNG DRETDFSLWD MHPETGTFRV VLNYNGTSQE LVAVPGRKLS WPLGYPPPDI  420
PKCGFDNEDP ACSQDHFSTL EEQKLISEED LGGEQKLISE EDLHHHHHH             469

SEQ ID NO: 78            moltype = AA  length = 469
FEATURE                  Location/Qualifiers
source                    1..469
                          mol_type = protein
                          organism = synthetic construct
SEQUENCE: 78
GNLTVAVVLP LANTSYPWSW ARVGPAVELA LAKVKARPDL LPGWTVRTVL GSSESALGVC  60
SDTAAPLTAV DLKWEHNPAV FLGPGCVYAA APVGRFTAHW RVPLLTAGAP ALGFGAKDEY  120
ALTTRAGPSH AKLGDFVAAL HRRLGWERQA LVLYAYQPGD DQPCFFVVGG LYMRVRDRLN  180
ITVDHLEFAE GDRDHYTLLL RTVRRKGRVI YICSSPDTFR TLMLLALEAG LSGEDYVFFH  240
LDLFGHSLQG AHGLVPRRPW EREDGQDVSA HQAFQAAKII TYKEPDNPEY LEFLRKLKHL  300
AREQFNFTME DGLVNTIPAA FHDGLLLYAQ AVTETLAHGG TVTDGESITQ RMWNRSFQGV  360
TGYLKMDSNG DRETDFSLWD MDPETGAFRV VLNFNGTSQE LVTVSGHTLN WPLGHPPPDV  420
PRCGFDNEDP ACNQDHFSTL EEQKLISEED LGGEQKLISE EDLHHHHHH             469
```